US010500268B2

United States Patent
Cox et al.

(10) Patent No.: US 10,500,268 B2
(45) Date of Patent: Dec. 10, 2019

(54) METHODS AND COMPOSITIONS RELATED TO INCREASING THE FIDELITY OF INFLUENZA A VIRUS FOR VACCINE DEVELOPMENT

(71) Applicants: UNIVERSITY OF ROCHESTER, Rochester, NY (US); Andrew Cox, Rochester, NY (US); Stephen Dewhurst, Rochester, NY (US)

(72) Inventors: Andrew Cox, Rochester, NY (US); Stephen Dewhurst, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 15/744,551

(22) PCT Filed: Jul. 14, 2016

(86) PCT No.: PCT/US2016/042195
§ 371 (c)(1),
(2) Date: Jan. 12, 2018

(87) PCT Pub. No.: WO2017/011620
PCT Pub. Date: Jan. 19, 2017

(65) Prior Publication Data
US 2019/0000958 A1    Jan. 3, 2019

Related U.S. Application Data

(60) Provisional application No. 62/192,163, filed on Jul. 14, 2015.

(51) Int. Cl.
| | | |
|---|---|---|
| *A61K 39/145* | (2006.01) | |
| *A61K 39/12* | (2006.01) | |
| *C07K 14/005* | (2006.01) | |
| *C12N 7/00* | (2006.01) | |
| *C12N 9/12* | (2006.01) | |
| *A61K 39/00* | (2006.01) | |

(52) U.S. Cl.
CPC .............. *A61K 39/145* (2013.01); *C12N 7/00* (2013.01); *C12N 9/1247* (2013.01); *C12Y 207/07006* (2013.01); *A61K 2039/5254* (2013.01); *C12N 2760/16122* (2013.01); *C12N 2760/16134* (2013.01)

(58) Field of Classification Search
CPC .. C12N 7/00; C12N 2760/16122; C12N 9/22; C12N 2760/16134; C12N 2760/16222; C12N 9/1247; C12N 2760/16034; C12N 2760/16234; C12N 2760/16051; C12N 2760/16121; C12N 2760/16161; C12N 2760/16061; C12N 2760/16261; C07K 14/005; A61K 2039/5254; A61K 39/145; A61K 39/12; A61K 2039/525; C12Y 207/07006
See application file for complete search history.

(56) References Cited

U.S. PATENT DOCUMENTS

| | | | | |
|---|---|---|---|---|
| 2008/0175861 A1* | 7/2008 | Cameron | .................. | C12N 7/00 424/204.1 |
| 2015/0224187 A1* | 8/2015 | Cox | ....................... | C12N 9/127 424/209.1 |
| 2015/0368621 A1* | 12/2015 | Kawaoka | ................. | C12N 7/00 424/186.1 |
| 2018/0223261 A1* | 8/2018 | Cox | ....................... | A61K 39/12 |

FOREIGN PATENT DOCUMENTS

WO     2008/140622 A2     11/2008

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10.*
Wentworth et. al. Polymerase PA [Influenza A virus (A/Philippines/219/2009)]. GenBank: AFM71818.1. Jun. 20, 2012.*
Watson SJ. polymerase PA [Influenza A virus (A/swine/Poland/15817/2011)]. Gen Bank: AKJ83250.1. Aug. 3, 2015.*
Lee HK, et. al. polymerase PA [Influenza A virus (A/Singapore/S2010.304b/2010(H3N2))]. GenBank: AIG45682.1. Aug. 30, 2014.*
Zhang H, et. al. polymerase PA [Influenza A virus (A/environrnent/Hunan/7-73/2008(H5N1))]. GenBank: ACZ05902.1. Nov. 22, 2009.*
Lee HJ, et. al. polymerase PB1, partial [Influenza A virus (A/pekin duck/Korea/LBM78/2007(H3N2))]. GenBank: ACY56567.1. Jun, 6, 2012.*
Kim LM, et. al. polymerase PB1 [Influenza A virus (A/environment/Hong Kong/258/1997(H5))]. GenBank: ACZ45841.1. Nov. 28, 2009.*
Wentworth DE, et. al. Polymerase PB1 [Influenza A virus (A/swine/Iowa/02539/2009(N1))]. GenBank: AHB23857.1. Nov. 27, 2013.*
Ghedin E, et. al. RecName: Full=RNA-directed RNA polymerase catalytic subunit; AltName: Full=Polymerase basic protein 1; Short=PB1; AltName: Full=RNA-directed RNA polymerase subunit P1. UniProtKB/Swiss-Prot: A4GCJ4.1, Dep. May 5, 2009.*
Wong KKY. The Influenza Polymerase: The Relationship Between Evolution and Replication Fidelity of Influenza Viruses. PhD Dissertation, Univ. of New South Wales. 2011.*
Recommendations for prevention and control of influenza in children, 2014-2015. Pediatrics. 2014; 134(5):e1503-19. Epub Sep. 24, 2014. doi: 10.1542/peds.2014-2413. PubMed PMID: 25246619.
Rezende LF, Prasad VR. Nucleoside-analog resistance mutations in HIV-1 reverse transcriptase and their influence on polymerase fidelity and viral mutation rates. Int J Biochem Cell Biol. 2004; 36(9):1716-34. Epub Jun. 9, 2004. doi: 10.1016/j.biocel.2004.02. 025. PubMed PMID: 15183340.
Schickli JH, Flandorfer A, Nakaya T, Martinez-Sobrido L, Garcia-Sastre A, Palese P. Plasmid-only rescue of influenza A virus vaccine candidates. Philos Trans R Soc Lond B Biol Sci. 2001; 356(1416):1965-73. Epub Jan. 10, 2002. doi: 10.1098/rstb.2001.0979. PubMed PMID: 11779399; PMCID: PMC1088576.

(Continued)

*Primary Examiner* — Rachel B Gill
(74) *Attorney, Agent, or Firm* — Meunier Carlin & Curfman LLC

(57) ABSTRACT

Disclosed are compositions and methods for related to mutant influenza viruses with increased fidelity.

Figure 1:
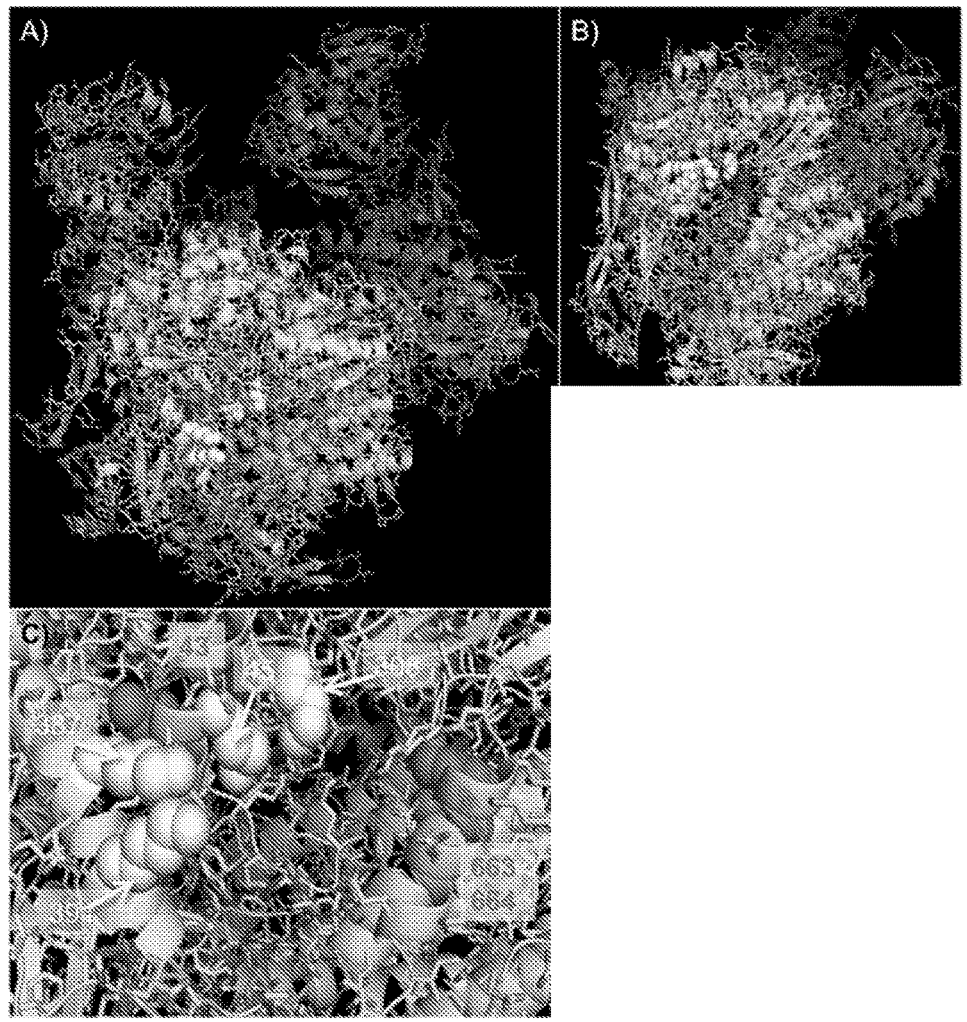

7 Claims, 6 Drawing Sheets
Specification includes a Sequence Listing.

(56) References Cited

OTHER PUBLICATIONS

Singh K, Kaushik N, Jin J, Madhusudanan M, Modak MJ. Role of Q190 of MuLV RT in ddNTP resistance and fidelity of DNA synthesis: a molecular model of interactions with substrates. Protein Eng. 2000; 13(9):635-43. Epub Oct. 31, 2000. PubMed PMID: 11054458.

Snyder MH, Betts RF, DeBorde D, Tierney EL, Clements ML, Herrington D, Sears SD, Dolin R, Maassab HF, Murphy BR. Four viral genes independently contribute to attenuation of live influenza A/Ann Arbor/6/60 (H2N2) cold-adapted reassortant virus vaccines. J Virol. 1988; 62(2):488-95. Epub Feb. 1, 1988 PubMed PMID: 3336068; PMCID: PMC250559.
Steel J, Lowen AC, Mubareka S, Palese P. Transmission of influenza virus in a mammalian host is increased by PB2 amino acids 627K or 627E/701N. PLoS Pathog. 2009; 5(1):e1000252. Epub Jan. 3, 2009. doi: 10.1371/journal.ppat.1000252. PubMed PMID: 19119420; PMCID: PMC2603332.
Treanor JJ, Kotloff K, Betts RF, Belshe R, Newman F, Iacuzio D, Wittes J, Bryant M. Evaluation of trivalent, live, cold-adapted (CAIV-T) and inactivated (TIV) influenza vaccines in prevention of virus infection and illness following challenge of adults with wild-type influenza A (H1N1), A (H3N2), and B viruses. Vaccine. 1999; 18(9-10):899-906. Epub Dec. 2, 1999. PubMed PMID: 10580204.
Tricco AC, Chit A, Soobiah C, Hallett D, Meier G, Chen MH, Tashkandi M, Bauch CT, Loeb M. Comparing influenza vaccine efficacy against mismatched and matched strains: a systematic review and meta-analysis. BMC Med. 2013; 11:153. Epub Jun. 27, 2013. doi: 10.1186/1741-7015-11-153. PubMed PMID: 23800265; PMCID: PMC3706345.
Tsfasman TM, Markushin SG, Akopova, II, Ghendon YZ. Molecular mechanisms of reversion to the ts+ (non-temperature-sensitive) phenotype of influenza A cold-adapted (ca) virus strains. J Gen Virol. 2007; 88(Pt 10):2724-9. Epub Sep. 18, 2007. doi: 10.1099/vir.0.83014-0. PubMed PMID: 17872525.
Vesikari T. Emerging data on the safety and efficacy of influenza vaccines in children. Pediatr Infect Dis J. 2008; 27(11 Suppl):S159-61. Epub Nov. 26, 2008. doi: 10.1097/INF.0b013e31818a545d. PubMed PMID: 18955892.
Vignuzzi M, Wendt E, Andino R. Engineering attenuated virus vaccines by controlling replication fidelity. Nat Med. 2008; 14(2):154-61. Epub Feb. 5, 2008. doi: 10.1038/nm1726. PubMed PMID: 18246077.
Weber M, Sediri H, Felgenhauer U, Binzen I, Banfer S, Jacob R, Brunotte L, Garcia-Sastre A, Schmid-Burgk JL, Schmidt T, Hornung V, Kochs G, Schwemmle M, Klenk HD, Weber F. Influenza virus adaptation PB2-627K modulates nucleocapsid inhibition by the pathogen sensor RIG-I. Cell Host Microbe. 2015; 17(3):309-19. Epub Feb. 24, 2015. doi: 10.1016/j.chom.2015.01.005. PubMed PMID: 25704008; PMCID: PMC4359673.
Weeks SA, Lee CA, Zhao Y, Smidansky ED, August A, Arnold JJ, Cameron CE. A Polymerase mechanism-based strategy for viral attenuation and vaccine development. J Biol Chem. 2012;287(38):31618-22. Epub Aug. 3, 2012. doi: 10.1074/jbc.C112.401471. PubMed PMID: 22854962; PMCID: PMC3442494.
Weiss KK, Bambara RA, Kim B. Mechanistic role of residue Gln151 in error prone DNA synthesis by human immunodeficiency virus type 1 (HIV-1) reverse transcriptase (RT). Pre-steady state kinetic study of the Q151N HIV-1 RT mutant with increased fidelity. J Biol Chem. 2002;277(25):22662-9. Epub Apr. 3, 2002. doi: 10.1074/jbc.M200202200. PubMed PMID: 11927582.
Yang X, Smidansky ED, Maksimchuk KR, Lum D, Welch JL, Arnold JJ, Cameron CE, Boehr DD. Motif D of viral RNA-dependent RNA polymerases determines efficiency and fidelity of nucleotide addition. Structure. 2012;20(9):1519-27. Epub Jul. 24, 2012. doi: 10.1016/j.str.2012.06.012. PubMed PMID: 22819218; PMCID: PMC3438331.
International Search Report and Written Opinion dated Jan. 24, 2017, from International Application No. PCT/US2016/042195, 18 pages.
International Preliminary Report on Patentability dated Jan. 25, 2018, from International Application No. PCT/US2016/042195, 12 pages.
Kaushik N, Singh K, Alluru I, Modak MJ. Tyrosine 222, a member of the YXDD motif of MuLV RT, is catalytically essential and is a major component of the fidelity center. Biochemistry. 1999;38(9):2617-27. Epub Mar. 1, 1999 doi: 10.1021/bi9824285. PubMed PMID: 10052931.
Aggarwal S et al. "Biochemical characterization of enzyme fidelity of influenza A virus RNA polymerase complex", PLoS One. 2010;5(4).
Aggarwal S, Dewhurst S, Takimoto T, Kim B. Biochemical impact of the host adaptation-associated PB2 E627K mutation on the temperature-dependent RNA synthesis kinetics of influenza A virus polymerase complex. J Biol Chem. 2011;286(40):34504-13. Epub Aug. 6, 2011. doi: 10.1074/jbc.M111.262048. PubMed PMID: 21816827; PMCID: PMC3186381.
Arezi B, Hogrefe HH. Escherichia coli DNA polymerase III epsilon subunit increases Moloney murine leukemia virus reverse transcriptase fidelity and accuracy of RT-PCR procedures. Anal Biochem. 2007;360(1):84-91. Epub Nov. 17, 2006. doi: 10.1016/j.ab.2006.10.009. PubMed PMID: 17107651.
Batiuk TD, Schnizlein-Bick C, Plotkin Z, Dagher PC. Guanine nucleosides and Jurkat cell death: roles of ATP depletion and accumulation of deoxyribonucleotides. Am J Physiol. Cell Physiol. 2001;281(6):C1776-84. Epub Nov. 8, 2001. PubMed PMID: 11698235.
Belshe RB, Ambrose CS, Yi T. Safety and efficacy of live attenuated influenza vaccine in children 2-7 years of age. Vaccine. 2008;26 Suppl 4:D10-6. Epub Jul. 10, 2008. doi: 10.1016/j.vaccine.2008.06.083. PubMed PMID: 18611422.
Bogs J, Kalthoff D, Veits J, Pavlova S, Schwemmle M, Manz B, Mettenleiter TC, Stech J. Reversion of PB2-627E to -627K during replication of an H5N1 Clade 2.2 virus in mammalian hosts depends on the origin of the nucleoprotein. J Virol. 2011;85(20):10691-8. Epub Aug. 19, 2011. doi: 10.1128/jvi.00786-11. PubMed PMID: 21849466; PMCID: PMC3187502.
Boyer PL, Stenbak CR, Hoberman D, Linial ML, Hughes SH. In vitro fidelity of the prototype primate foamy virus (PFV) RT compared to HIV-1 RT. Virology. 2007;367(2):253-64. Epub Jul. 17, 2007. doi: 10.1016/j.virol.2007.05.034. PubMed PMID: 17631930; PMCID: PMC2720797.
Bradel-Tretheway BG, Kelley Z, Chakraborty-Sett S, Takimoto T, Kim B, Dewhurst S. The human H5N1 influenza A virus polymerase complex is active in vitro over a broad range of temperatures, in contrast to the WSN complex, and this property can be attributed to the PB2 subunit. J Gen Virol. 2008;89(Pt 12):2923-32. Epub Nov. 15, 2008 doi: 10.1099/vir.0.2008/006254-0. PubMed PMID: 19008377; PMCID: PMC3067610.
Bumet FM, Lind PE. Reversion to virulence in an influenza virus mutant. Aust J Exp Biol Med Sci. 1957;35(3):225-39. Epub Jun. 1, 1957 PubMed PMID: 13471436.
Campagnola G, McDonald S, Beaucourt S, Vignuzzi M, Peersen OB. Structure-function relationships underlying the replication fidelity of viral RNA-dependent RNA polymerases. J Virol. 2015;89(1):275-86. Epub Oct. 17, 2014. doi: 10.1128/jvi.01574-14. PubMed PMID: 25320316; PMCID: PMC4301111.
Cheung PP, Watson SJ, Choy KT, Fun Sia S, Wong DD, Poon LL, Kellam P, Guan Y, Malik Peiris JS, Yen HL. Generation and characterization of influenza A viruses with altered polymerase fidelity. Nat Commun. 2014;5:4794. Epub Sep. 4, 2014. doi: 10.1038/ncomms5794. PubMed PMID: 25183443; PMCID: PMC4155405.
Cox A, Baker SF, Nogales A, Martinez-Sobrido L, Dewhurst S. Development of a mouse-adapted live attenuated influenza virus that permits in vivo analysis of enhancements to the safety of live attenuated influenza virus vaccine. J Virol. 2015;89(6):3421-6. Epub Jan. 2, 2015. doi: 10.1128/jvi.02636-14. PubMed PMID: 25552727; PMCID: PMC4337518.
Cox NJ, Kendal AP. Genetic stability of A/Ann Arbor/6/60 cold-mutant (temperature-sensitive) live influenza virus genes: analysis by oligonucleotide mapping of recombinant vaccine strains before and after replication in volunteers. J Infect Dis. 1984;149(2):194-200. Epub Feb. 1, 1984. PubMed PMID: 6699431. (Abstract).
Cox NJ, Kitame F, Kendal AP, Maassab HF, Naeve C. Identification of sequence changes in the cold-adapted, live attenuated influenza

(56) References Cited

OTHER PUBLICATIONS vaccine strain, A/Ann Arbor/6/60 (H2N2). Virology. 1988;167(2):554-67. Epub Dec. 1, 1988. PubMed PMID: 2974219.
Cramer J, Strerath M, Marx A, Restle T. Exploring the effects of active site constraints on HIV-1 reverse transcriptase DNA polymerase fidelity. J Biol Chem. 2002;277(46):43593-8. Epub Aug. 30, 2002. doi: 10.1074/jbc.M207854200. PubMed PMID: 12200452.
Curti E, Jaeger J. Residues Arg283, Arg285, and Ile287 in the nucleotide binding pocket of bovine viral diarrhea virus NS5B RNA polymerase affect catalysis and fidelity. J Virol. 2013;87(1):199-207. Epub Oct. 19, 2012. doi: 10.1128/vi.06968-11. PubMed PMID: 23077294; PMCID: PMC3536392.
Donabedian AM, DeBorde DC, Cook S, Smitka CW, Maassab HF. A mutation in the PA protein gene of cold-adapted B/Ann Arbor/1/66 influenza virus associated with reversion of temperature sensitivity and attenuated virulence. Virology. 1988;163(2):444-51. Epub Apr. 1, 1988. PubMed PMID: 3354203.
Eckert KA, Kunkel TA. Fidelity of DNA synthesis catalyzed by human DNA polymerase alpha and HIV-1 reverse transcriptase: effect of reaction pH. Nucleic Acids Res. 1993;21(22):5212-20. Epub Nov. 11, 1993. PubMed PMID: 7504813; PMCID: PMC310639.
Fisher TS, Prasad VR. Substitutions of Phe61 located in the vicinity of template 5'-overhang influence polymerase fidelity and nucleoside analog sensitivity of HIV-1 reverse transcriptase. J Biol Chem. 2002;277(25):22345-52. Epub Apr. 12, 2002. doi: 10.1074/jbc.M200282200. PubMed PMID: 11948182.
Garforth SJ, Domaoal RA, Lwatula C, Landau MJ, Meyer AJ, Anderson KS, Prasad VR. K65R and K65A substitutions in HIV-1 reverse transcriptase enhance polymerase fidelity by decreasing both dNTP misinsertion and mispaired primer extension efficiencies. J Mol Biol. 2010;401(1):33-44. Epub Jun. 12, 2010. doi: 10.1016/j.jmb.2010.06.001. PubMed PMID: 20538005; PMCID: PMC2925049.
Gnadig NF, Beaucourt S, Campagnola G, Borderia AV, Sanz-Ramos M, Gong P, Blanc H, Peersen OB, Vignuzzi M. Coxsackievirus B3 mutator strains are attenuated in vivo. Proc Natl Acad Sci U S A. 2012;109(34):E2294-303. Epub Aug. 3, 2012. doi: 10.1073/pnas.1204022109. PubMed PMID: 22853955; PMCID: PMC3427060.
Graham RL, Becker MM, Eckerle LD, Bolles M, Denison MR, Baric RS. A live, impaired-fidelity coronavirus vaccine protects in an aged, immunocompromised mouse model of lethal disease. Nat Med. 2012;18(12):1820-6. Epub Nov. 13, 2012. doi: 10.1038/nm.2972. PubMed PMID: 23142821; PMCID: PMC3518599.
Grohskopf LA, Olsen SJ, Sokolow LZ, Bresee JS, Cox NJ, Broder KR, Karron RA, Walter EB. Prevention and control of seasonal influenza with vaccines: recommendations of the Advisory Committee on Immunization Practices (ACIP)—United States, 2014-15 influenza season. MMWR Morb Mortal Wkly Rep. 2014;63(32):691-7. Epub Aug. 15, 2014. PubMed PMID: 25121712.
Hrabar A, Vodopija I, Andre FE, Mitchell JR, Maassab HF, Hennessy AV, Davenport FM. A placebo-controlled dose-response study of the reactogenicity and immunogenicity of a cold-adapted recombinant A/Victoria/3/75 (H3N2) live influenza virus candidate vaccine in healthy volunteers. Dev Biol Stand. 1977;39:53-60. Epub Jun. 1, 1977. PubMed PMID: 342317.
Hudjetz B, Gabriel G. Human-like PB2 627K influenza virus polymerase activity is regulated by importin-alpha1 and -alpha7. PLoS Pathog. 2012;8(1):e1002488. Epub Jan. 26, 2012. doi: 10.1371/journal.ppat.1002488. PubMed PMID: 22275867; PMCID: PMC3262014.
Keulen W, van Wijk A, Schuurman R, Berkhout B, Boucher CA. Increased polymerase fidelity of lamivudine-resistant HIV-1 variants does not limit their evolutionary potential. AIDS. 1999;13(11):1343-9. Epub Aug. 17, 1999. PubMed PMID: 10449287.
Kim B, Ayran JC, Sagar SG, Adman ET, Fuller SM, Tran NH, Horrigan J. New human immunodeficiency virus, type 1 reverse transcriptase (HIV-1 RT) mutants with increased fidelity of DNA synthesis. Accuracy, template binding, and processivity. J Biol Chem. 1999;274(39):27666-73. Epub Sep. 17, 1999. PubMed PMID: 10488107.
Kim HW, Arrobio JO, Brandt CD, Parrott RH, Murphy BR, Richman DD, Chanock RM. Temperature-sensitive mutants of influenza A virus: response of children to the influenza A/Hong Kong/68-ts-1(E) (H3N2) and influenza A/Udorn/72-ts-1(E) (H3N2) candidate vaccine viruses and significance of immunity to neuraminidase antigen. Pediatr Res. 1976;10 (4):238-42. Epub Apr. 1, 1976. doi: 10.1203/00006450-197604000-00008. PubMed PMID: 1272630.
Lauring AS, Jones JO, Andino R. Rationalizing the development of live attenuated virus vaccines. Nat Biotechnol. 2010;28(6):573-9. Epub Jun. 10, 2010. doi: 10.1038/nbt.1635. PubMed PMID: 20531338; PMCID: PMC2883798.
Li H, Durbin R. Fast and accurate short read alignment with Burrows-Wheeler transform. Bioinformatics. 2009;25 (14)1754-60. Epub May 20, 2009. doi: 10.1093/bioinformatics/btp324. PubMed PMID: 19451168; PMCID: PMC2705234.
Li H. A statistical framework for SNP calling, mutation discovery, association mapping and population genetical parameter estimation from sequencing data. Bioinformatics. 2011;27(21):2987-93. Epub Sep. 10, 2011. doi: 10.1093/bioinformatics/btr509. PubMed PMID: 21903627; PMCID: PMC3198575.
Liu X, Yang X, Lee CA, Moustafa IM, Smidansky ED, Lum D, Arnold JJ, Cameron CE, Boehr DD. Vaccine-derived mutation in motif D of poliovirus RNA-dependent RNA polymerase lowers nucleotide incorporation fidelity. J Biol Chem. 2013;288(45):32753-65. Epub Oct. 3, 2013. doi: 10.1074/jbc.M113.484428. PubMed PMID: 24085299; PMCID: PMC3820909.
Long JS, Howard WA, Nunez A, Moncorge O, Lycett S, Banks J, Barclay WS. The effect of the PB2 mutation 627K on highly pathogenic H5N1 avian influenza virus is dependent on the virus lineage. J Virol. 2013;87(18):9983-96. Epub Jul. 12, 2013. doi: 10.1128/jvi.01399-13. PubMed PMID: 23843645; PMCID: PMC3753988.
Maassab HF. Adaptation and growth characteristics of influenza virus at 25 degrees c. Nature. 1967;213(5076):612-4. Epub Feb. 11, 1967. PubMed PMID: 6040602.
Maassab HF. Biologic and immunologic characteristics of cold-adapted influenza virus. J Immunol. 1969;102 (3):728-32. Epub Mar. 1, 1969. PubMed PMID: 5773321.
Martinez-Sobrido L, Garcia-Sastre A. Generation of recombinant influenza virus from plasmid DNA. J Vis Exp. 2010 (42). Epub Aug. 24, 2010. doi: 10.3791/2057. PubMed PMID: 20729804; PMCID: PMC3156010.
Medimmune. FluMist Quadrivalent Prescribing Information 2013-2014. 2013 [cited Jun. 10, 2015].
Meng T, Kwang J. Attenuation of human enterovirus 71 high-replication-fidelity variants in AG129 mice. J Virol. 2014;88(10):5803-15. Epub Mar. 14, 2014. doi: 10.1128/jvi.00289-14. PubMed PMID: 24623423; PMCID: PMC4019108.
Murphy BR, Maassab HF, Wood FT, Jr., Chanock RM. Characterization of the temperature sensitive phenotype of the A/Ann Arbor/6/60 cold-adapted virus and its recombinants. Infect Immun. 1981;32(2):960-3. Epub May 1, 1981. PubMed PMID: 7251154; PMCID: PMC351536.
Noble E, Cox A, Deval J, Kim B. Endonuclease substrate selectivity characterized with full-length PA of influenza A virus polymerase. Virology. 2012;433(1):27-34. Epub Jul. 31, 2012. doi: 10.1016/j.virol.2012.07.008. PubMed PMID: 22841552; PMCID: PMC3647620.
Nogales A, Baker SF, Ortiz-Riano E, Dewhurst S, Topham DJ, Martinez-Sobrido L. Influenza A virus attenuation by codon deoptimization of the NS gene for vaccine development. J Virol. 2014;88(18):10525-40. Epub Jun. 27, 2014. doi: 10.1128/jvi.01565-14. PubMed PMID: 24965472; PMCID: PMC4178899.
Osterholm MT, Kelley NS, Sommer A, Belongia EA. Efficacy and effectiveness of influenza vaccines: a systematic review and meta-analysis. Lancet Infect Dis. 2012;12(1):36-44. Epub Oct. 29, 2011. doi: 10.1016/s1473-3099(11)70295-x. PubMed PMID: 22032844.
Oude Essink BB, Back NK, Berkhout B. Increased polymerase fidelity of the 3TC-resistant variants of HIV-1 reverse transcriptase. Nucleic Acids Res. 1997;25(16):3212-7. Epub Aug. 15, 1997. PubMed PMID: 9241233; PMCID: PMC146883.
Parkin NT, Chiu P, Coelingh K. Genetically engineered live attenuated influenza A virus vaccine candidates. J Virol. 1997;71(4):2772-8. Epub Apr. 1, 1997. PubMed PMID: 9060631; PMCID: PMC191400.

(56) References Cited

OTHER PUBLICATIONS

Parkin NT, Chiu P, Coelingh KL. Temperature sensitive mutants of influenza A virus generated by reverse genetics and clustered charged to alanine mutagenesis. Virus Res. 1996;46(1-2):31-44. Epub Dec. 1, 1996. PubMed PMID: 9029775.

Pflug A, Guilligay D, Reich S, Cusack S. Structure of influenza A polymerase bound to the viral RNA promoter. Nature. 2014;516(7531):355-60. Epub Nov. 20, 2014. doi: 10.1038/nature14008. PubMed PMID: 25409142.

Poland GA, Fleming DM, Treanor JJ, Maraskovsky E, Luke TC, Ball EM, Poland CM. New Wisdom to Defy an Old Enemy: Summary from a scientific symposium at the 4th Influenza Vaccines for the World (IVW) 2012 Congress, Oct. 11, Valencia, Spain. Vaccine. 2013;31 Suppl 1:A1-20. Epub Apr. 23, 2013. doi: 10.1016/j.vaccine.2013.02.033. PubMed PMID: 23587330.

Prasad VR, Drosopoulos WC, Hamburgh ME. Perspective: research highlights at the Albert Einstein College of Medicine Center for AIDS research. Approaches to control drug resistance in HIV: the role of increased polymerase fidelity. AIDS Res Hum Retroviruses. 1996;12(11):959-63. Epub Jul. 20, 1996. PubMed PMID: 8827210.

Prevention and control of influenza with vaccines: interim recommendations of the Advisory Committee on Immunization Practices (ACIP), 2013. MMWR Morb Mortal Wkly Rep. 2013;62(18):356. Epub May 10, 2013. PubMed PMID: 23657110.

Recommendations for prevention and control of influenza in children, 2013-2014. Pediatrics. 2013;132(4):e1089-104. Epub Sep. 4, 2013. doi: 10.1542/peds.2013-2377. PubMed PMID: 23999962.

* cited by examiner

| Virus | Bases sequenced | 1/Error rate | Viral titer |
|---|---|---|---|
| WT | 29,971 | 1070 | 3.58 e7 |
| 43I | 15,809 | 1440 | 4.32 e7 |
| 387D | 17,121 | 1320 | 1.46 e7 |
| 391D | 8,959 | 1790 | 1.66 e8 |
| 663K | 13,497 | 1690 | 4.28 e7 |

SEQUENCE LISTING

<160> NUMBER OF SEQ ID NOS: 13

<210> SEQ ID NO 1
<211> LENGTH: 713
<212> TYPE: PRT
<213> ORGANISM: Influenza A virus

<400> SEQUENCE: 1

Met Glu Asn Phe Val Arg Thr Asn Phe Asn Pro Met Ile Leu Glu Arg
1               5                   10                  15

Ala Glu Lys Thr Met Lys Glu Tyr Gly Glu Asn Pro Gln Asn Glu Gly
            20                  25                  30

Asn Lys Phe Ala Ala Ile Ser Thr His Met Glu Val Cys Phe Met Tyr
        35                  40                  45

Ser Asp Phe His Phe Ile Asp Leu Glu Gly Asn Thr Ile Val Lys Glu
    50                  55                  60

Asn Asp Asp Asn Ala Met Leu Lys His Arg Phe Glu Ile Ile Glu
65                  70                  75                  80

Gly Gln Glu Arg Asn Ile Ala Trp Thr Ile Val Asn Ser Ile Cys Asn
                85                  90                  95

Met Thr Glu Asn Ser Lys Pro Arg Phe Leu Pro Asp Leu Tyr Asp Tyr
            100                 105                 110

Lys Thr Asn Lys Phe Ile Glu Ile Gly Val Thr Arg Arg Lys Val Glu
        115                 120                 125

Asp Tyr Tyr Tyr Glu Lys Ala Ser Lys Leu Lys Gly Glu Asn Val Tyr
    130                 135                 140

Ile His Ile Phe Ser Phe Asp Gly Glu Glu Met Ala Thr Asp Asp Glu
145                 150                 155                 160

Tyr Ile Leu Asp Glu Glu Ser Arg Ala Arg Ile Lys Thr Arg Leu Phe
                165                 170                 175

Val Leu Arg Gln Glu Leu Ala Thr Ala Gly Leu Trp Asp Ser Phe Arg
            180                 185                 190

Gln Ser Glu Lys Gly Glu Glu Thr Leu Glu Glu Phe Ser Tyr Pro
        195                 200                 205

Pro Thr Phe Gln Arg Leu Ala Asn Gln Ser Leu Pro Pro Ser Phe Lys
    210                 215                 220

Asp Tyr His Gln Phe Lys Ala Tyr Val Ser Ser Phe Lys Ala Asn Gly
225                 230                 235                 240

Asn Ile Glu Ala Lys Leu Gly Ala Met Ser Lys Val Asn Ala Gln
                245                 250                 255

Ile Glu Ser Phe Asp Pro Arg Thr Ile Arg Glu Leu Glu Leu Pro Glu
            260                 265                 270

Gly Lys Phe Cys Thr Gln Arg Ser Lys Phe Leu Leu Met Asp Ala Met
        275                 280                 285

Lys Leu Ser Val Leu Asn Pro Ala His Glu Gly Glu Gly Ile Pro Met
    290                 295                 300

Lys Asp Ala Lys Ala Cys Leu Asp Thr Phe Trp Gly Trp Lys Lys Ala
305                 310                 315                 320

Thr Ile Ile Lys Lys His Glu Lys Gly Val Asn Thr Asn Tyr Leu Met
                325                 330                 335

Ile Trp Glu Gln Leu Leu Glu Ser Ile Lys Glu Met Glu Gly Lys Phe
            340                 345                 350

Leu Asn Leu Lys Lys Thr Asn His Leu Lys Trp Gly Leu Gly Glu Gly
        355                 360                 365

```
Gln Ala Pro Glu Lys Met Asp Phe Glu Asp Cys Lys Val Pro Asp
    370             375             380

Leu Phe Gln Tyr Lys Ser Glu Pro Pro Glu Lys Arg Lys Leu Ala Ser
385             390             395             400

Trp Ile Gln Ser Glu Phe Asn Lys Ala Ser Glu Leu Thr Asn Ser Asn
            405             410             415

Trp Ile Glu Phe Asp Glu Leu Gly Asn Asp Val Ala Pro Ile Glu His
            420             425             430

Ile Ala Ser Arg Arg Asn Phe Phe Thr Ala Glu Val Ser Gln Cys
        435             440             445

Arg Ala Ser Glu Tyr Ile Met Lys Ala Val Tyr Ile Asn Thr Ala Leu
    450             455             460

Leu Asn Ser Ser Cys Thr Ala Met Glu Glu Tyr Gln Val Ile Pro Ile
465             470             475             480

Ile Thr Lys Cys Arg Asp Thr Ser Gly Gln Arg Arg Thr Asn Leu Tyr
            485             490             495

Gly Phe Ile Ile Lys Gly Arg Ser His Leu Arg Asn Asp Thr Asp Val
            500             505             510

Val Asn Phe Ile Ser Leu Glu Phe Ser Leu Thr Asp Pro Arg Asn Glu
    515             520             525

Ile His Lys Trp Glu Lys Tyr Cys Val Leu Glu Ile Gly Asp Met Glu
    530             535             540

Ile Arg Thr Ser Ile Ser Thr Ile Met Lys Pro Val Tyr Leu Tyr Val
545             550             555             560

Arg Thr Asn Gly Thr Ser Lys Ile Lys Met Lys Trp Gly Met Glu Met
            565             570             575

Arg Arg Cys Leu Leu Gln Ser Leu Gln Gln Val Glu Ser Met Ile Glu
        580             585             590

Ala Glu Ser Ala Val Lys Glu Lys Asp Met Thr Glu Pro Phe Phe Arg
        595             600             605

Asn Arg Glu Asn Asp Trp Pro Ile Gly Glu Ser Pro Gln Gly Ile Glu
    610             615             620

Lys Gly Thr Ile Gly Lys Val Cys Arg Val Leu Leu Ala Lys Ser Val
625             630             635             640

Phe Asn Ser Ile Tyr Ala Ser Ala Gln Leu Glu Gly Phe Ser Ala Glu
            645             650             655

Ser Arg Lys Leu Leu Leu Ile Gln Ala Phe Arg Asp Asn Leu Asp
        660             665             670

Pro Gly Thr Phe Asp Leu Lys Gly Leu Tyr Glu Ala Ile Glu Glu Cys
    675             680             685

Ile Ile Asn Asp Pro Trp Val Leu Leu Asn Ala Ser Trp Phe Asn Ser
    690             695             700

Phe Leu Lys Ala Val Gln Leu Ser Met
705             710
```

<210> SEQ ID NO 2  
<211> LENGTH: 756  
<212> TYPE: PRT  
<213> ORGANISM: Influenza A virus
<400> SEQUENCE: 2

```
Met Asp Val Asn Pro Met Leu Ile Phe Leu Lys Val Pro Val Gln Asn
1               5               10              15

Ala Ile Ser Thr Thr Phe Pro Tyr Thr Gly Asp Pro Pro Tyr Ser His
            20              25              30
```

```
Gly Thr Gly Thr Gly Tyr Thr Met Asp Thr Val Ile Arg Thr His Asp
         35                  40                  45

Tyr Ser Ser Arg Gly Ile Trp Lys Thr Asn Ser Glu Thr Gly Ala Gln
 50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Leu Ile Glu Gly Leu Asp
                 85                  90                  95

Arg Ser His Pro Gly Leu Phe Glu Thr Ala Cys Gln Glu Thr Ile Asp
                100                 105                 110

Ala Ile Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
130                 135                 140

Asn Thr Ile Glu Val Phe Arg Lys Asn Gly Tyr Lys Leu Asn Glu Ser
145                 150                 155                 160

Gly Arg Leu Ile Asp Phe Leu Lys Asp Val Leu Leu Ser Phe Glu Asn
                165                 170                 175

Asp Ser Met Glu Val Thr Thr His Phe Gln Lys Lys Arg Ile Arg
                180                 185                 190

Asp Asn His Ser Lys Lys Met Ile Thr Gln Arg Thr Ile Gly Lys Lys
            195                 200                 205

Arg Val Lys Leu Thr Lys Lys Asn Tyr Leu Ile Arg Ala Leu Thr Leu
            210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Leu Leu Ala Arg Asn Ile Cys Glu Arg Leu Glu Gln Ser Gly Leu Pro
            260                 265                 270

Val Gly Gly Asn Glu Lys Lys Ala Lys Leu Ala Asn Val Ile Lys Lys
            275                 280                 285

Met Met Ala Lys Ser Thr Asp Glu Glu Leu Ser Tyr Thr Ile Thr Gly
290                 295                 300

Asp Asn Thr Lys Trp Asn Glu Asn Gln Asn Pro Arg Ile Phe Leu Ala
305                 310                 315                 320

Met Val Leu Arg Ile Thr Ala Gly Gln Pro Glu Trp Phe Arg Asp Leu
                325                 330                 335

Leu Ala Val Ala Pro Ile Met Phe Ser Asn Lys Val Ala Arg Leu Gly
            340                 345                 350

Arg Gly Tyr Met Phe Glu Ser Lys Ser Met His Leu Arg Thr Gln Ile
            355                 360                 365

Ser Ala Glu Asn Leu Ser Asp Ile Asn Leu Arg Tyr Phe Asn Glu Asp
370                 375                 380

Thr Lys Lys Lys Ile Glu Lys Ile Arg His Leu Met Val Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Val Leu Asn Leu Gly Gln Arg Glu Ile Leu
            420                 425                 430

Lys Arg Thr Tyr Trp Trp Asp Gly Leu Gln Ser Ser Asp Asp Phe Ala
            435                 440                 445
```

```
Leu Ile Ile Asn Gly His Phe Lys Glu Asp Ile Gln Gln Gly Val Asn
            450                 455                 460

His Phe Tyr Arg Thr Cys Lys Leu Val Gly Ile Asn Met Ser Gln Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ala Gly Asn Asn Glu Ser Ala Asp Met Ser Ile Gly Thr Thr
            515                 520                 525

Val Ile Lys Thr Asn Met Ile Asn Asn Asp Leu Gly Pro Ala Thr Ala
530                 535                 540

Gln Met Ala Ile Gln Leu Phe Ile Lys Asp Tyr Arg Tyr Thr Tyr Arg
545                 550                 555                 560

Cys His Arg Gly Asp Thr Asn Leu Glu Thr Arg Arg Thr Lys Ser Ile
                565                 570                 575

Lys Arg Leu Trp Thr Glu Thr Ile Ser Lys Ala Gly Leu Leu Val Ala
            580                 585                 590

Asp Gly Gly Pro Asn Pro Tyr Asn Leu Arg Asn Leu His Ile Pro Glu
            595                 600                 605

Val Cys Leu Lys Trp Ser Leu Met Asp Pro Asp Tyr Arg Gly Arg Leu
610                 615                 620

Cys Asn Pro Asn Asn Pro Phe Val His His Met Glu Val Glu Ser Thr
625                 630                 635                 640

Asn Leu Ala Val Val Met Pro Ala His Gly Pro Ala Lys Ser Leu Glu
                645                 650                 655

Tyr Asp Ala Val Ala Thr Thr His Ser Trp Thr Pro Lys Arg Asn Arg
            660                 665                 670

Ser Ile Leu Asn Thr Asn Gln Arg Gly Ile Leu Glu Asp Glu Arg Ile
            675                 680                 685

Tyr Gln Lys Cys Cys Gln Val Phe Glu Lys Phe Phe Pro Ser Ser Thr
690                 695                 700

Tyr Arg Arg Pro Ile Gly Met Ala Ser Met Leu Asp Ala Met Leu Ser
705                 710                 715                 720

Arg Ala Arg Ile Asp Ala Arg Ile Asp Leu Glu Ser Gly Arg Ile Ser
                725                 730                 735

Ser Gln Asp Phe Ser Glu Ile Thr Asn Thr Cys Lys Ala Ile Glu Ala
            740                 745                 750

Leu Lys Arg Gln
        755

<210> SEQ ID NO 3
<211> LENGTH: 716
<212> TYPE: PRT
<213> ORGANISM: Influenza A virus

<400> SEQUENCE: 3

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60
```

-continued

```
Leu Gly Asp Pro Asn Ala Leu Leu Lys His Arg Phe Glu Ile Ile Glu
 65                  70                  75                  80

Gly Arg Asp Arg Thr Met Ala Trp Thr Val Val Asn Ser Ile Cys Asn
                 85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Thr Ile Glu Glu Arg Phe Glu Ile Thr
        195                 200                 205

Gly Thr Met Arg Lys Leu Ala Asp Gln Ser Leu Pro Pro Asn Phe Ser
210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
450                 455                 460

Ile Asn Thr Ala Leu Leu Asn Ala Ser Cys Ala Ala Met Asp Asp Phe
465                 470                 475                 480
```

```
Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
            530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
                595                 600                 605

Lys Glu Phe Phe Glu Asn Lys Ser Glu Thr Trp Pro Ile Gly Glu Ser
            610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
                660                 665                 670

Arg Asp Asn Leu Glu Pro Gly Thr Phe Asp Leu Gly Gly Leu Tyr Glu
            675                 680                 685

Ala Ile Glu Glu Cys Leu Ile Asn Asp Pro Trp Val Leu Leu Asn Ala
690                 695                 700

Ser Trp Phe Asn Ser Phe Leu Thr His Ala Leu Ser
705                 710                 715

<210> SEQ ID NO 4
<211> LENGTH: 757
<212> TYPE: PRT
<213> ORGANISM: Influenza A virus

<400> SEQUENCE: 4

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140
```

```
Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Met Gly Lys Lys
            195                 200                 205

Lys Gln Arg Leu Asn Lys Arg Ser Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
                275                 280                 285

Met Met Thr Asn Ser Gln Asp Thr Glu Leu Ser Phe Thr Ile Thr Gly
            290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
        370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
                420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
        450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560
```

```
Cys His Arg Gly Asp Thr Gln Ile Gln Thr Arg Arg Ser Phe Glu Ile
                565                 570                 575
Lys Lys Leu Trp Glu Gln Thr Arg Ser Lys Val Gly Leu Leu Val Ser
            580                 585                 590
Asp Gly Gly Pro Asn Leu Tyr Asn Ile Arg Asn Leu His Ile Pro Glu
        595                 600                 605
Val Cys Leu Lys Trp Glu Leu Met Asp Glu Asp Tyr Gln Gly Arg Leu
    610                 615                 620
Cys Asn Pro Leu Asn Pro Phe Val Ser His Lys Glu Ile Glu Ser Met
625                 630                 635                 640
Asn Asn Ala Val Met Met Pro Ala His Gly Pro Ala Lys Asn Met Glu
                645                 650                 655
Tyr Asp Ala Val Ala Thr Thr His Ser Trp Ile Pro Lys Arg Asn Arg
            660                 665                 670
Ser Ile Leu Asn Thr Ser Gln Arg Gly Val Leu Glu Asp Glu Gln Met
        675                 680                 685
Tyr Gln Arg Cys Cys Asn Leu Phe Glu Lys Phe Phe Pro Ser Ser Ser
    690                 695                 700
Tyr Arg Arg Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
Lys Glu Glu Phe Thr Glu Ile Met Lys Ile Cys Ser Thr Ile Glu Glu
            740                 745                 750
Leu Arg Arg Gln Lys
        755

<210> SEQ ID NO 5
<211> LENGTH: 2233
<212> TYPE: PRT
<213> ORGANISM: Influenza A virus

<400> SEQUENCE: 5

Ala Gly Cys Gly Ala Ala Ala Gly Cys Ala Gly Gly Thr Ala Cys Thr
1               5                   10                  15
Gly Ala Thr Cys Cys Ala Ala Ala Thr Gly Gly Ala Ala Gly Ala Ala
                20                  25                  30
Thr Thr Thr Thr Gly Thr Gly Cys Gly Ala Cys Ala Ala Thr Gly Cys
            35                  40                  45
Thr Thr Cys Ala Ala Thr Cys Cys Gly Ala Thr Gly Ala Thr Thr Gly
        50                  55                  60
Thr Cys Gly Ala Gly Cys Thr Thr Gly Cys Gly Gly Ala Ala Ala Ala
65                  70                  75                  80
Ala Ala Cys Ala Ala Thr Gly Ala Ala Ala Gly Ala Gly Thr Ala Thr
                85                  90                  95
Gly Gly Gly Gly Ala Gly Ala Cys Cys Thr Gly Ala Ala Ala Ala Ala
            100                 105                 110
Thr Cys Gly Ala Ala Cys Ala Ala Cys Ala Ala Thr Thr
        115                 120                 125
Thr Gly Cys Ala Gly Cys Ala Thr Ala Thr Gly Cys Ala Cys Thr
    130                 135                 140
Cys Ala Cys Thr Thr Gly Gly Ala Ala Gly Thr Ala Thr Gly Cys Thr
145                 150                 155                 160
Thr Cys Ala Thr Gly Thr Ala Thr Thr Cys Ala Gly Ala Thr Thr Thr
                165                 170                 175
```

-continued

```
Thr Cys Ala Cys Thr Thr Cys Ala Thr Cys Ala Ala Thr Gly Ala Gly
            180                 185                 190

Cys Ala Ala Gly Gly Cys Gly Ala Gly Thr Cys Ala Ala Thr Ala Ala
        195                 200                 205

Thr Cys Gly Thr Ala Gly Ala Ala Cys Thr Thr Gly Gly Thr Gly Ala
    210                 215                 220

Thr Cys Cys Ala Ala Ala Thr Gly Cys Ala Cys Thr Thr Thr Thr Gly
225                 230                 235                 240

Ala Ala Gly Cys Ala Cys Ala Gly Ala Thr Thr Thr Gly Ala Ala Ala
                245                 250                 255

Thr Ala Ala Thr Cys Gly Ala Gly Gly Gly Ala Ala Gly Ala Gly Ala
            260                 265                 270

Thr Cys Gly Cys Ala Cys Ala Ala Thr Gly Gly Cys Cys Thr Gly Gly
        275                 280                 285

Ala Cys Ala Gly Thr Ala Gly Thr Ala Ala Ala Cys Ala Gly Thr Ala
    290                 295                 300

Thr Thr Thr Gly Cys Ala Ala Cys Ala Cys Thr Ala Cys Ala Gly Gly
305                 310                 315                 320

Gly Gly Cys Thr Gly Ala Gly Ala Ala Ala Cys Cys Ala Ala Ala Gly
                325                 330                 335

Thr Thr Thr Cys Thr Ala Cys Cys Ala Gly Ala Thr Thr Thr Gly Thr
            340                 345                 350

Ala Thr Gly Ala Thr Thr Ala Cys Ala Ala Gly Gly Ala Gly Ala Ala
        355                 360                 365

Thr Ala Gly Ala Thr Thr Cys Ala Thr Cys Gly Ala Ala Ala Thr Thr
    370                 375                 380

Gly Gly Ala Gly Thr Ala Ala Cys Ala Ala Gly Gly Ala Gly Ala Gly
385                 390                 395                 400

Ala Ala Gly Thr Thr Cys Ala Cys Ala Thr Ala Thr Ala Cys Thr Ala
                405                 410                 415

Thr Cys Thr Gly Gly Ala Ala Ala Ala Gly Gly Cys Cys Ala Ala Thr
            420                 425                 430

Ala Ala Ala Ala Thr Thr Ala Ala Ala Thr Cys Thr Gly Ala Gly Ala
        435                 440                 445

Ala Ala Ala Cys Ala Cys Ala Cys Ala Thr Cys Cys Ala Cys Ala Thr
    450                 455                 460

Thr Thr Thr Cys Thr Cys Gly Thr Thr Cys Ala Cys Thr Gly Gly Gly
465                 470                 475                 480

Gly Ala Ala Gly Ala Ala Ala Thr Gly Gly Cys Cys Ala Cys Ala Ala
                485                 490                 495

Ala Gly Gly Cys Ala Gly Ala Cys Thr Ala Cys Ala Cys Thr Cys Thr
            500                 505                 510

Cys Gly Ala Thr Gly Ala Ala Gly Ala Ala Ala Gly Cys Ala Gly Gly
        515                 520                 525

Gly Cys Thr Ala Gly Gly Ala Thr Cys Ala Ala Ala Ala Cys Cys Ala
    530                 535                 540

Gly Ala Cys Thr Ala Thr Thr Cys Ala Cys Cys Ala Thr Ala Ala Gly
545                 550                 555                 560

Ala Cys Ala Ala Gly Ala Ala Ala Thr Gly Gly Cys Cys Ala Gly Cys
                565                 570                 575

Ala Gly Ala Gly Gly Cys Cys Thr Cys Thr Gly Gly Gly Ala Thr Thr
            580                 585                 590
```

-continued

Cys Cys Thr Thr Thr Cys Gly Thr Cys Ala Gly Thr Cys Gly Ala
        595                 600                 605

Gly Ala Gly Ala Gly Gly Ala Gly Ala Ala Gly Ala Gly Ala Cys Ala
    610                 615                 620

Ala Thr Thr Gly Ala Ala Gly Ala Ala Ala Gly Gly Thr Thr Thr Gly
625                 630                 635                 640

Ala Ala Ala Thr Cys Ala Cys Ala Gly Gly Ala Ala Cys Ala Ala Thr
            645                 650                 655

Gly Cys Gly Cys Ala Ala Gly Cys Thr Thr Gly Cys Cys Gly Ala Cys
        660                 665                 670

Cys Ala Ala Ala Gly Thr Cys Thr Cys Cys Gly Cys Cys Gly Ala
    675                 680                 685

Ala Cys Thr Thr Cys Thr Cys Cys Ala Gly Cys Cys Thr Thr Gly Ala
    690                 695                 700

Ala Ala Ala Thr Thr Thr Thr Ala Gly Ala Gly Cys Cys Thr Ala Thr
705                 710                 715                 720

Gly Thr Gly Gly Ala Thr Gly Gly Ala Thr Thr Cys Gly Ala Ala Cys
            725                 730                 735

Cys Gly Ala Ala Cys Gly Gly Cys Thr Ala Cys Ala Thr Thr Gly Ala
        740                 745                 750

Gly Gly Gly Cys Ala Ala Gly Cys Thr Gly Thr Cys Thr Cys Ala Ala
    755                 760                 765

Ala Thr Gly Thr Cys Cys Ala Ala Gly Ala Ala Gly Thr Ala Ala
    770                 775                 780

Ala Thr Gly Cys Thr Ala Gly Ala Ala Thr Thr Gly Ala Ala Cys Cys
785                 790                 795                 800

Thr Thr Thr Thr Thr Thr Gly Ala Ala Ala Cys Ala Ala Cys Ala
            805                 810                 815

Cys Cys Ala Cys Gly Ala Cys Cys Ala Cys Thr Thr Ala Gly Ala Cys
        820                 825                 830

Thr Thr Cys Cys Gly Ala Ala Thr Gly Gly Gly Cys Cys Thr Cys Cys
    835                 840                 845

Cys Thr Gly Thr Thr Cys Thr Cys Ala Gly Cys Gly Gly Thr Cys Cys
    850                 855                 860

Ala Ala Ala Thr Thr Cys Cys Thr Gly Cys Thr Gly Ala Thr Gly Gly
865                 870                 875                 880

Ala Thr Gly Cys Cys Thr Thr Ala Ala Ala Thr Ala Ala Gly
        885                 890                 895

Cys Ala Thr Thr Gly Ala Gly Gly Ala Cys Cys Ala Ala Gly Thr
    900                 905                 910

Cys Ala Thr Gly Ala Ala Gly Gly Ala Gly Ala Gly Gly Gly Ala Ala
    915                 920                 925

Thr Ala Cys Cys Gly Cys Thr Ala Thr Ala Thr Gly Ala Thr Gly Cys
930                 935                 940

Ala Ala Thr Cys Ala Ala Ala Thr Gly Cys Ala Thr Gly Ala Gly Ala
945                 950                 955                 960

Ala Cys Ala Thr Thr Cys Thr Thr Thr Gly Gly Ala Thr Gly Gly Ala
            965                 970                 975

Ala Gly Gly Ala Ala Cys Cys Cys Ala Ala Thr Gly Thr Thr Gly Thr
        980                 985                 990

Thr Ala Ala Ala Cys Cys Ala Cys Ala Cys Gly Ala Ala Ala Ala Gly
    995                 1000                1005

Gly Gly Ala Ala Thr Ala Ala Ala Thr Cys Cys Ala Ala Ala Thr

-continued

|   |   |   |   | 1010 |   |   |   |   | 1015 |   |   |   |   | 1020 |

Thr Ala Thr Cys Thr Thr Cys Thr Gly Thr Cys Ala Thr Gly Gly
         1025                1030                1035

Ala Ala Gly Cys Ala Ala Gly Thr Ala Cys Thr Gly Gly Cys Ala
         1040                1045                1050

Gly Ala Ala Cys Thr Gly Cys Ala Gly Gly Ala Cys Ala Thr Thr
         1055                1060                1065

Gly Ala Gly Ala Ala Thr Gly Ala Gly Gly Ala Gly Ala Ala Ala
         1070                1075                1080

Ala Thr Thr Cys Cys Ala Ala Ala Gly Ala Cys Thr Ala Ala Ala
         1085                1090                1095

Ala Ala Thr Ala Thr Gly Ala Ala Gly Ala Ala Ala Ala Cys Ala
         1100                1105                1110

Ala Gly Thr Cys Ala Gly Cys Thr Ala Ala Ala Gly Thr Gly Gly
         1115                1120                1125

Gly Cys Ala Cys Thr Thr Gly Gly Thr Gly Ala Gly Ala Ala Cys
         1130                1135                1140

Ala Thr Gly Gly Cys Ala Cys Cys Ala Gly Ala Ala Ala Ala Gly
         1145                1150                1155

Gly Thr Ala Gly Ala Cys Thr Thr Thr Gly Ala Cys Gly Ala Cys
         1160                1165                1170

Thr Gly Thr Ala Ala Ala Gly Ala Thr Gly Thr Ala Gly Gly Thr
         1175                1180                1185

Gly Ala Thr Thr Thr Gly Ala Ala Gly Cys Ala Ala Thr Ala Thr
         1190                1195                1200

Gly Ala Thr Ala Gly Thr Gly Ala Thr Gly Ala Ala Cys Cys Ala
         1205                1210                1215

Gly Ala Ala Thr Thr Gly Ala Gly Gly Thr Cys Gly Cys Thr Thr
         1220                1225                1230

Gly Cys Ala Ala Gly Thr Thr Gly Gly Ala Thr Thr Cys Ala Gly
         1235                1240                1245

Ala Ala Thr Gly Ala Gly Thr Thr Thr Ala Ala Cys Ala Ala Gly
         1250                1255                1260

Gly Cys Ala Thr Gly Cys Gly Ala Ala Cys Thr Gly Ala Cys Ala
         1265                1270                1275

Gly Ala Thr Thr Cys Ala Ala Gly Cys Thr Gly Gly Ala Thr Ala
         1280                1285                1290

Gly Ala Gly Cys Thr Cys Gly Ala Thr Gly Ala Gly Ala Thr Thr
         1295                1300                1305

Gly Gly Ala Gly Ala Ala Gly Ala Thr Gly Thr Gly Gly Cys Thr
         1310                1315                1320

Cys Cys Ala Ala Thr Thr Gly Ala Ala Cys Ala Cys Ala Thr Thr
         1325                1330                1335

Gly Cys Ala Ala Gly Cys Ala Thr Gly Ala Gly Ala Ala Gly Gly
         1340                1345                1350

Ala Ala Thr Thr Ala Thr Thr Thr Cys Ala Cys Ala Thr Cys Ala
         1355                1360                1365

Gly Ala Gly Gly Thr Gly Thr Cys Thr Cys Ala Cys Thr Gly Cys
         1370                1375                1380

Ala Gly Ala Gly Cys Cys Cys Ala Gly Ala Ala Thr Ala Cys
         1385                1390                1395

Ala Thr Ala Ala Thr Gly Ala Ala Gly Gly Gly Gly Thr Gly
         1400                1405                1410

```
Thr Ala  Cys Ala Thr Cys Ala  Ala Thr Ala Cys Thr  Gly Cys Cys
    1415                 1420                 1425

Thr Thr  Gly Cys Thr Thr Ala  Ala Thr Gly Cys Ala  Thr Cys Thr
    1430                 1435                 1440

Thr Gly  Thr Gly Cys Ala Gly  Cys Ala Ala Thr Gly  Gly Ala Thr
    1445                 1450                 1455

Gly Ala  Thr Thr Thr Cys Cys  Ala Ala Thr Thr Ala  Ala Thr Thr
    1460                 1465                 1470

Cys Cys  Ala Ala Thr Gly Ala  Thr Ala Ala Gly Cys  Ala Ala Gly
    1475                 1480                 1485

Thr Gly  Thr Ala Gly Ala Ala  Cys Thr Ala Ala Gly  Gly Ala Gly
    1490                 1495                 1500

Gly Gly  Ala Ala Gly Gly Cys  Gly Ala Ala Ala Gly  Ala Cys Cys
    1505                 1510                 1515

Ala Ala  Cys Thr Thr Gly Thr  Ala Thr Gly Gly Thr  Thr Thr Cys
    1520                 1525                 1530

Ala Thr  Cys Ala Thr Ala Ala  Ala Ala Gly Gly Ala  Ala Gly Ala
    1535                 1540                 1545

Thr Cys  Cys Cys Ala Cys Thr  Thr Ala Ala Gly Gly  Ala Ala Thr
    1550                 1555                 1560

Gly Ala  Cys Ala Cys Cys Gly  Ala Cys Gly Thr Gly  Gly Thr Ala
    1565                 1570                 1575

Ala Ala  Cys Thr Thr Thr Gly  Thr Gly Ala Gly Cys  Ala Thr Gly
    1580                 1585                 1590

Gly Ala  Gly Thr Thr Thr Thr  Cys Thr Cys Thr Cys  Ala Cys Thr
    1595                 1600                 1605

Gly Ala  Cys Cys Cys Ala Ala  Gly Ala Cys Thr Thr  Gly Ala Ala
    1610                 1615                 1620

Cys Cys  Ala Cys Ala Thr Ala  Ala Ala Thr Gly Gly  Gly Ala Gly
    1625                 1630                 1635

Ala Ala  Gly Thr Ala Cys Thr  Gly Thr Gly Thr Thr  Cys Thr Thr
    1640                 1645                 1650

Gly Ala  Gly Ala Thr Ala Gly  Gly Ala Gly Ala Thr  Ala Thr Gly
    1655                 1660                 1665

Cys Thr  Thr Ala Thr Ala Ala  Gly Ala Ala Gly Thr  Gly Cys Cys
    1670                 1675                 1680

Ala Thr  Ala Gly Gly Cys Cys  Ala Gly Gly Thr Thr  Thr Cys Ala
    1685                 1690                 1695

Ala Gly  Gly Cys Cys Cys Ala  Thr Gly Thr Thr Cys  Thr Thr Gly
    1700                 1705                 1710

Thr Ala  Thr Gly Thr Gly Ala  Gly Ala Ala Cys Ala  Ala Ala Thr
    1715                 1720                 1725

Gly Gly  Ala Ala Cys Cys Thr  Cys Ala Ala Ala Ala  Ala Thr Thr
    1730                 1735                 1740

Ala Ala  Ala Ala Thr Gly Ala  Ala Ala Thr Gly Gly  Gly Gly Ala
    1745                 1750                 1755

Ala Thr  Gly Gly Ala Gly Ala  Thr Gly Ala Gly Gly  Cys Gly Thr
    1760                 1765                 1770

Thr Gly  Cys Cys Thr Cys Cys  Thr Cys Cys Ala Gly  Thr Cys Ala
    1775                 1780                 1785

Cys Thr  Thr Cys Ala Ala Cys  Ala Ala Ala Thr Thr  Gly Ala Gly
    1790                 1795                 1800
```

-continued

```
Ala Gly  Thr Ala Thr Gly Ala  Thr Thr Gly Ala Ala  Gly Cys Thr
    1805                 1810                 1815

Gly Ala  Gly Thr Cys Cys Thr  Cys Thr Gly Thr Cys  Ala Ala Ala
    1820                 1825                 1830

Gly Ala  Gly Ala Ala Ala Gly  Ala Cys Ala Thr Gly  Ala Cys Cys
    1835                 1840                 1845

Ala Ala  Ala Gly Ala Gly Thr  Thr Cys Thr Thr Thr  Gly Ala Gly
    1850                 1855                 1860

Ala Ala  Cys Ala Ala Ala Thr  Cys Ala Gly Ala Ala  Ala Cys Ala
    1865                 1870                 1875

Thr Gly  Gly Cys Cys Cys Ala  Thr Thr Gly Gly Ala  Gly Ala Gly
    1880                 1885                 1890

Thr Cys  Cys Cys Cys Cys Ala  Ala Ala Gly Gly Ala  Gly Thr Gly
    1895                 1900                 1905

Gly Ala  Gly Gly Ala Ala Ala  Gly Thr Thr Cys Cys  Ala Thr Thr
    1910                 1915                 1920

Gly Gly  Gly Ala Ala Gly Gly  Thr Cys Thr Gly Cys  Ala Gly Gly
    1925                 1930                 1935

Ala Cys  Thr Thr Thr Ala Thr  Thr Ala Gly Cys Ala  Ala Ala Gly
    1940                 1945                 1950

Thr Cys  Gly Gly Thr Ala Thr  Thr Cys Ala Ala Cys  Ala Gly Cys
    1955                 1960                 1965

Thr Thr  Gly Thr Ala Thr Gly  Cys Ala Thr Cys Thr  Cys Cys Ala
    1970                 1975                 1980

Cys Ala  Ala Cys Thr Ala Gly  Ala Ala Gly Gly Ala  Thr Thr Thr
    1985                 1990                 1995

Thr Cys  Ala Gly Cys Thr Gly  Ala Ala Thr Cys Ala  Ala Gly Ala
    2000                 2005                 2010

Ala Ala  Ala Cys Thr Gly Cys  Thr Thr Cys Thr Thr  Ala Thr Cys
    2015                 2020                 2025

Gly Thr  Thr Cys Ala Gly Gly  Cys Thr Cys Thr Thr  Ala Gly Gly
    2030                 2035                 2040

Gly Ala  Cys Ala Ala Cys Cys  Thr Thr Gly Ala Ala  Cys Cys Thr
    2045                 2050                 2055

Gly Gly  Gly Ala Cys Cys Thr  Thr Thr Gly Ala Thr  Cys Thr Thr
    2060                 2065                 2070

Gly Gly  Gly Gly Gly Gly Cys  Thr Ala Thr Ala Thr  Gly Ala Ala
    2075                 2080                 2085

Gly Cys  Ala Ala Thr Thr Gly  Ala Gly Gly Ala Gly  Thr Gly Cys
    2090                 2095                 2100

Cys Thr  Gly Ala Thr Thr Ala  Ala Thr Gly Ala Thr  Cys Cys Cys
    2105                 2110                 2115

Thr Gly  Gly Gly Thr Thr Thr  Thr Gly Cys Thr Thr  Ala Ala Thr
    2120                 2125                 2130

Gly Cys  Thr Thr Cys Thr Thr  Gly Gly Thr Thr Cys  Ala Ala Cys
    2135                 2140                 2145

Thr Cys  Cys Thr Thr Cys Cys  Thr Thr Ala Cys Ala  Cys Ala Thr
    2150                 2155                 2160

Gly Cys  Ala Thr Thr Gly Ala  Gly Thr Thr Ala Gly  Thr Thr Gly
    2165                 2170                 2175

Thr Gly  Gly Cys Ala Gly Thr  Gly Cys Thr Ala Cys  Thr Ala Thr
    2180                 2185                 2190

Thr Thr  Gly Cys Thr Ala Thr  Cys Cys Ala Thr Ala  Cys Thr Gly
```

```
            2195                2200                2205

Thr Cys Cys Ala Ala Ala  Ala Ala Gly Thr Ala  Cys Cys Thr
            2210                2215                2220

Thr Gly Thr Thr Thr Cys  Thr Ala Cys Thr
            2225                2230

<210> SEQ ID NO 6
<211> LENGTH: 2341
<212> TYPE: PRT
<213> ORGANISM: Influenza A virus

<400> SEQUENCE: 6

Ala Gly Cys Gly Ala Ala Gly Cys Ala Gly Gly Cys Ala Ala Ala
1               5                   10                  15

Cys Cys Ala Thr Thr Thr Gly Ala Ala Thr Gly Gly Ala Thr Gly Thr
                20                  25                  30

Cys Ala Ala Thr Cys Cys Gly Ala Cys Cys Thr Thr Ala Cys Thr Thr
            35                  40                  45

Thr Thr Cys Thr Thr Ala Ala Ala Ala Gly Thr Gly Cys Cys Ala Gly
        50                  55                  60

Cys Ala Cys Ala Ala Ala Ala Thr Gly Cys Thr Ala Thr Ala Ala Gly
65                  70                  75                  80

Cys Ala Cys Ala Ala Cys Thr Thr Thr Cys Cys Cys Thr Thr Ala Thr
                85                  90                  95

Ala Cys Thr Gly Gly Ala Gly Ala Cys Cys Cys Thr Cys Cys Thr Thr
                100                 105                 110

Ala Cys Ala Gly Cys Cys Ala Thr Gly Gly Gly Ala Cys Ala Gly Gly
            115                 120                 125

Ala Ala Cys Ala Gly Gly Ala Thr Ala Cys Ala Cys Cys Ala Thr Gly
        130                 135                 140

Gly Ala Thr Ala Cys Thr Gly Thr Cys Ala Ala Cys Ala Gly Gly Ala
145                 150                 155                 160

Cys Ala Cys Ala Thr Cys Ala Gly Thr Ala Cys Thr Cys Ala Gly Ala
                165                 170                 175

Ala Ala Ala Gly Gly Gly Ala Ala Gly Ala Thr Gly Gly Ala Cys Ala
                180                 185                 190

Ala Cys Ala Ala Ala Cys Ala Cys Cys Gly Ala Ala Ala Cys Thr Gly
            195                 200                 205

Gly Ala Gly Cys Ala Cys Cys Gly Cys Ala Ala Cys Thr Cys Ala Ala
        210                 215                 220

Cys Cys Cys Gly Ala Thr Thr Gly Ala Thr Gly Gly Gly Cys Cys Ala
225                 230                 235                 240

Cys Thr Gly Cys Cys Ala Gly Ala Ala Gly Ala Cys Ala Ala Thr Gly
                245                 250                 255

Ala Ala Cys Cys Ala Ala Gly Thr Gly Gly Thr Thr Ala Thr Gly Cys
                260                 265                 270

Cys Cys Ala Ala Ala Cys Ala Gly Thr Thr Gly Thr Gly Thr Gly Ala
            275                 280                 285

Thr Thr Gly Gly Ala Gly Gly Cys Gly Ala Thr Gly Gly Cys Thr Thr
        290                 295                 300

Thr Cys Cys Thr Thr Gly Ala Gly Gly Ala Ala Thr Cys Cys Cys Ala
305                 310                 315                 320

Thr Cys Cys Thr Gly Gly Thr Ala Thr Thr Thr Thr Gly Ala Ala Ala
                325                 330                 335
```

-continued

```
Ala Ala Cys Thr Cys Gly Thr Gly Thr Ala Thr Thr Gly Ala Ala Ala
            340                 345                 350
Cys Gly Ala Thr Gly Gly Ala Gly Gly Thr Thr Gly Thr Thr Cys Ala
        355                 360                 365

Gly Cys Ala Ala Ala Cys Ala Cys Gly Ala Gly Thr Ala Gly Ala Cys
    370                 375                 380

Ala Ala Gly Cys Thr Gly Ala Cys Ala Cys Ala Ala Gly Gly Cys Cys
385                 390                 395                 400
Gly Ala Cys Ala Gly Ala Cys Cys Thr Ala Thr Gly Ala Cys Thr Gly
                405                 410                 415

Gly Ala Cys Thr Cys Thr Ala Ala Ala Thr Ala Gly Ala Ala Ala Cys
            420                 425                 430
Cys Ala Ala Cys Cys Thr Gly Cys Thr Gly Cys Ala Ala Cys Ala Gly
        435                 440                 445

Cys Ala Thr Thr Gly Gly Cys Cys Ala Ala Cys Ala Cys Ala Ala Thr
    450                 455                 460

Ala Gly Ala Ala Gly Thr Gly Thr Thr Cys Ala Gly Ala Thr Cys Ala
465                 470                 475                 480
Ala Ala Thr Gly Gly Cys Cys Thr Cys Ala Cys Gly Gly Cys Cys Ala
                485                 490                 495

Ala Thr Gly Ala Gly Thr Cys Thr Gly Gly Ala Ala Gly Gly Cys Thr
            500                 505                 510
Cys Ala Thr Ala Gly Ala Cys Thr Thr Cys Cys Thr Thr Ala Ala Gly
        515                 520                 525

Gly Ala Thr Gly Thr Ala Ala Thr Gly Gly Ala Gly Thr Cys Ala Ala
    530                 535                 540

Thr Gly Ala Ala Cys Ala Ala Ala Gly Ala Ala Gly Ala Ala Ala Thr
545                 550                 555                 560
Gly Gly Gly Gly Ala Thr Cys Ala Cys Ala Ala Cys Thr Cys Ala Thr
                565                 570                 575

Thr Thr Thr Cys Ala Gly Ala Gly Ala Ala Ala Gly Ala Gly Ala Cys
            580                 585                 590
Gly Gly Gly Thr Gly Ala Gly Ala Gly Ala Cys Ala Ala Thr Ala Thr
        595                 600                 605

Gly Ala Cys Thr Ala Ala Gly Ala Ala Ala Ala Thr Gly Ala Thr Ala
    610                 615                 620

Ala Cys Ala Cys Ala Gly Ala Gly Ala Ala Cys Ala Ala Thr Gly Gly
625                 630                 635                 640
Gly Thr Ala Ala Ala Ala Ala Gly Ala Ala Gly Cys Ala Gly Ala Gly
                645                 650                 655

Ala Thr Thr Gly Ala Ala Cys Ala Ala Ala Ala Gly Gly Ala Gly Thr
            660                 665                 670
Thr Ala Thr Cys Thr Ala Ala Thr Thr Ala Gly Ala Gly Cys Ala Thr
        675                 680                 685

Thr Gly Ala Cys Cys Cys Thr Gly Ala Ala Cys Ala Cys Ala Ala Thr
    690                 695                 700

Gly Ala Cys Cys Ala Ala Ala Gly Ala Thr Gly Cys Thr Gly Ala Gly
705                 710                 715                 720
Ala Gly Ala Gly Gly Gly Ala Ala Gly Cys Thr Ala Ala Ala Ala Cys
                725                 730                 735

Gly Gly Ala Gly Ala Gly Cys Ala Ala Thr Thr Gly Cys Ala Ala Cys
            740                 745                 750

Cys Cys Cys Ala Gly Gly Gly Ala Thr Gly Cys Ala Ala Ala Thr Ala
```

-continued

```
                755                 760                 765
Ala Gly Gly Gly Gly Thr Thr Thr Gly Thr Ala Thr Ala Cys Thr
    770                 775                 780

Thr Thr Gly Thr Thr Gly Ala Gly Ala Cys Ala Cys Thr Gly Gly Cys
785                 790                 795                 800

Ala Ala Gly Gly Ala Gly Thr Ala Thr Ala Thr Gly Thr Gly Ala Gly
                805                 810                 815

Ala Ala Ala Cys Thr Thr Gly Ala Ala Cys Ala Ala Thr Cys Ala Gly
                820                 825                 830

Gly Gly Thr Thr Gly Cys Cys Ala Gly Thr Gly Gly Ala Gly Gly
                835                 840                 845

Cys Ala Ala Thr Gly Ala Gly Ala Ala Gly Ala Ala Ala Gly Cys Ala
                850                 855                 860

Ala Ala Gly Thr Thr Gly Gly Cys Ala Ala Ala Thr Gly Thr Thr Gly
865                 870                 875                 880

Thr Ala Ala Gly Gly Ala Ala Gly Ala Thr Gly Ala Thr Gly Ala Cys
                885                 890                 895

Cys Ala Ala Thr Thr Cys Thr Cys Ala Gly Gly Ala Cys Ala Cys Cys
                900                 905                 910

Gly Ala Ala Cys Thr Thr Thr Cys Thr Thr Thr Cys Ala Cys Cys Ala
                915                 920                 925

Thr Cys Ala Cys Thr Gly Gly Ala Gly Ala Thr Ala Ala Cys Ala Cys
                930                 935                 940

Cys Ala Ala Ala Thr Gly Gly Ala Ala Cys Gly Ala Ala Ala Ala Thr
945                 950                 955                 960

Cys Ala Gly Ala Ala Thr Cys Cys Thr Cys Gly Gly Ala Thr Gly Thr
                965                 970                 975

Thr Thr Thr Thr Gly Gly Cys Cys Ala Thr Gly Ala Thr Cys Ala Cys
                980                 985                 990

Ala Thr Ala Thr Ala Thr Gly Ala Cys Cys Ala Gly Ala Ala Ala Thr
                995                1000                1005

Cys Ala Gly Cys Cys Cys Gly Ala Ala Thr Gly Gly Thr Thr Cys
               1010                1015                1020

Ala Gly Ala Ala Ala Thr Gly Thr Thr Cys Thr Ala Ala Gly Thr
               1025                1030                1035

Ala Thr Thr Gly Cys Thr Cys Cys Ala Ala Thr Ala Ala Thr Gly
               1040                1045                1050

Thr Thr Cys Thr Cys Ala Ala Ala Cys Ala Ala Ala Ala Thr Gly
               1055                1060                1065

Gly Cys Gly Ala Gly Ala Cys Thr Gly Gly Gly Ala Ala Ala Ala
               1070                1075                1080

Gly Gly Gly Thr Ala Thr Ala Thr Gly Thr Thr Thr Gly Ala Gly
               1085                1090                1095

Ala Gly Cys Ala Ala Gly Ala Gly Thr Ala Thr Gly Ala Ala Ala
               1100                1105                1110

Cys Thr Thr Ala Gly Ala Ala Cys Thr Cys Ala Ala Ala Thr Ala
               1115                1120                1125

Cys Cys Thr Gly Cys Ala Gly Ala Ala Ala Thr Gly Cys Thr Ala
               1130                1135                1140

Gly Cys Ala Ala Gly Cys Ala Thr Cys Gly Ala Thr Thr Thr Gly
               1145                1150                1155

Ala Ala Ala Thr Ala Thr Thr Thr Cys Ala Ala Thr Gly Ala Thr
               1160                1165                1170
```

Thr Cys Ala Ala Cys Ala Ala Gly Ala Ala Ala Gly Ala Ala Gly
1175 1180 1185

Ala Thr Thr Gly Ala Ala Ala Ala Ala Ala Thr Cys Cys Gly Ala
1190 1195 1200

Cys Cys Gly Cys Thr Cys Thr Thr Ala Ala Thr Ala Gly Ala Gly
1205 1210 1215

Gly Gly Gly Ala Cys Thr Gly Cys Ala Thr Cys Ala Thr Thr Gly
1220 1225 1230

Ala Gly Cys Cys Cys Thr Gly Gly Ala Ala Thr Gly Ala Thr Gly
1235 1240 1245

Ala Thr Gly Gly Gly Cys Ala Thr Gly Thr Thr Cys Ala Ala Thr
1250 1255 1260

Ala Thr Gly Thr Thr Ala Ala Gly Cys Ala Cys Thr Gly Thr Ala
1265 1270 1275

Thr Thr Ala Gly Gly Cys Gly Thr Cys Thr Cys Cys Ala Thr Cys
1280 1285 1290

Cys Thr Gly Ala Ala Thr Cys Thr Thr Gly Gly Ala Cys Ala Ala
1295 1300 1305

Ala Ala Gly Ala Gly Ala Thr Ala Cys Ala Cys Cys Ala Ala Gly
1310 1315 1320

Ala Cys Thr Ala Cys Thr Thr Ala Cys Thr Gly Gly Thr Gly Gly
1325 1330 1335

Gly Ala Thr Gly Gly Thr Cys Thr Thr Cys Ala Ala Thr Cys Cys
1340 1345 1350

Thr Cys Thr Gly Ala Cys Gly Ala Thr Thr Thr Gly Cys Thr
1355 1360 1365

Cys Thr Gly Ala Thr Thr Gly Thr Gly Ala Ala Thr Gly Cys Ala
1370 1375 1380

Cys Cys Cys Ala Ala Thr Cys Ala Thr Gly Ala Ala Gly Gly Gly
1385 1390 1395

Ala Thr Thr Cys Ala Ala Gly Cys Cys Gly Gly Ala Gly Thr Cys
1400 1405 1410

Gly Ala Cys Ala Gly Gly Thr Thr Thr Thr Ala Thr Cys Gly Ala
1415 1420 1425

Ala Cys Cys Thr Gly Thr Ala Ala Gly Cys Thr Ala Cys Thr Thr
1430 1435 1440

Gly Gly Ala Ala Thr Cys Ala Ala Thr Ala Thr Gly Ala Gly Cys
1445 1450 1455

Ala Ala Gly Ala Ala Ala Ala Ala Gly Thr Cys Thr Thr Ala Cys
1460 1465 1470

Ala Thr Ala Ala Ala Cys Ala Gly Ala Ala Cys Ala Gly Gly Thr
1475 1480 1485

Ala Cys Ala Thr Thr Thr Gly Ala Ala Thr Thr Cys Ala Cys Ala
1490 1495 1500

Ala Gly Thr Thr Thr Thr Thr Thr Cys Thr Ala Thr Cys Gly Thr
1505 1510 1515

Thr Ala Thr Gly Gly Gly Thr Thr Thr Gly Thr Thr Gly Cys Cys
1520 1525 1530

Ala Ala Thr Thr Thr Cys Ala Gly Cys Ala Thr Gly Gly Ala Gly
1535 1540 1545

Cys Thr Thr Cys Cys Cys Ala Gly Thr Thr Thr Thr Gly Gly Gly
1550 1555 1560

-continued

```
Gly Thr  Gly Thr Cys Thr Gly  Gly Gly Ala Thr Cys  Ala Ala Cys
    1565                 1570                 1575

Gly Ala  Gly Thr Cys Ala Gly  Cys Gly Gly Ala Cys  Ala Thr Gly
    1580                 1585                 1590

Ala Gly  Thr Ala Thr Thr Gly  Gly Ala Gly Thr Thr  Ala Cys Thr
    1595                 1600                 1605

Gly Thr  Cys Ala Thr Cys Ala  Ala Ala Ala Ala Cys  Ala Ala Thr
    1610                 1615                 1620

Ala Thr  Gly Ala Thr Ala Ala  Ala Cys Ala Ala Thr  Gly Ala Thr
    1625                 1630                 1635

Cys Thr  Thr Gly Gly Thr Cys  Cys Ala Gly Cys Ala  Ala Cys Ala
    1640                 1645                 1650

Gly Cys  Thr Cys Ala Ala Ala  Thr Gly Gly Cys Cys  Cys Thr Thr
    1655                 1660                 1665

Cys Ala  Gly Thr Thr Gly Thr  Thr Cys Ala Thr Cys  Ala Ala Ala
    1670                 1675                 1680

Gly Ala  Thr Thr Ala Cys Ala  Gly Gly Thr Ala Cys  Ala Cys Gly
    1685                 1690                 1695

Thr Ala  Cys Cys Gly Ala Thr  Gly Cys Cys Ala Thr  Ala Gly Ala
    1700                 1705                 1710

Gly Gly  Thr Gly Ala Cys Ala  Cys Ala Cys Ala Ala  Ala Thr Ala
    1715                 1720                 1725

Cys Ala  Ala Ala Cys Cys Cys  Gly Ala Ala Gly Ala  Thr Cys Ala
    1730                 1735                 1740

Thr Thr  Thr Gly Ala Ala Ala  Thr Ala Ala Ala Gly  Ala Ala Ala
    1745                 1750                 1755

Cys Thr  Gly Thr Gly Gly Gly  Ala Gly Cys Ala Ala  Ala Cys Cys
    1760                 1765                 1770

Cys Gly  Thr Thr Cys Cys Ala  Ala Ala Gly Thr Thr  Gly Gly Ala
    1775                 1780                 1785

Cys Thr  Gly Cys Thr Gly Gly  Thr Cys Thr Cys Cys  Gly Ala Cys
    1790                 1795                 1800

Gly Gly  Ala Gly Gly Cys Cys  Cys Ala Ala Ala Thr  Thr Thr Ala
    1805                 1810                 1815

Thr Ala  Cys Ala Ala Cys Ala  Thr Thr Ala Gly Ala  Ala Ala Thr
    1820                 1825                 1830

Cys Thr  Cys Cys Ala Cys Ala  Thr Thr Cys Cys Thr  Gly Ala Ala
    1835                 1840                 1845

Gly Thr  Cys Thr Gly Cys Cys  Thr Ala Ala Ala Ala  Thr Gly Gly
    1850                 1855                 1860

Gly Ala  Ala Thr Thr Gly Ala  Thr Gly Gly Ala Thr  Gly Ala Gly
    1865                 1870                 1875

Gly Ala  Thr Thr Ala Cys Cys  Ala Gly Gly Gly Gly  Cys Gly Thr
    1880                 1885                 1890

Thr Thr  Ala Thr Gly Cys Ala  Ala Cys Cys Cys Ala  Cys Thr Gly
    1895                 1900                 1905

Ala Ala  Cys Cys Cys Ala Thr  Thr Thr Gly Thr Cys  Ala Gly Cys
    1910                 1915                 1920

Cys Ala  Thr Ala Ala Ala Gly  Ala Ala Ala Thr Thr  Gly Ala Ala
    1925                 1930                 1935

Thr Cys  Ala Ala Thr Gly Ala  Ala Cys Ala Ala Thr  Gly Cys Ala
    1940                 1945                 1950

Gly Thr  Gly Ala Thr Gly Ala  Thr Gly Cys Cys Ala  Gly Cys Ala
```

|   |   |   |   |   |   |   |   |   |   |   |
|---|---|---|---|---|---|---|---|---|---|---|
| | | | | 1955 | | | 1960 | | 1965 | |
| Cys | Ala | Thr | Gly | Gly | Thr | Cys | Cys | Ala | Gly | Cys | Thr | Ala | Ala | Ala |
| | 1970 | | | | 1975 | | | | 1980 | |
| Ala | Ala | Cys | Ala | Thr | Gly | Gly | Ala | Gly | Thr | Ala | Thr | Gly | Ala | Thr |
| | 1985 | | | | 1990 | | | | 1995 | |
| Gly | Cys | Thr | Gly | Thr | Thr | Gly | Cys | Ala | Ala | Cys | Ala | Ala | Cys | Ala |
| | 2000 | | | | 2005 | | | | 2010 | |
| Cys | Ala | Cys | Thr | Cys | Cys | Thr | Gly | Gly | Ala | Thr | Cys | Cys | Cys | Cys |
| | 2015 | | | | 2020 | | | | 2025 | |
| Ala | Ala | Ala | Ala | Gly | Ala | Ala | Ala | Thr | Cys | Gly | Ala | Thr | Cys | Cys |
| | 2030 | | | | 2035 | | | | 2040 | |
| Ala | Thr | Cys | Thr | Thr | Gly | Ala | Ala | Thr | Ala | Cys | Ala | Ala | Gly | Thr |
| | 2045 | | | | 2050 | | | | 2055 | |
| Cys | Ala | Ala | Ala | Gly | Ala | Gly | Gly | Ala | Gly | Thr | Ala | Cys | Thr | Thr |
| | 2060 | | | | 2065 | | | | 2070 | |
| Gly | Ala | Gly | Gly | Ala | Thr | Gly | Ala | Ala | Cys | Ala | Ala | Ala | Thr | Gly |
| | 2075 | | | | 2080 | | | | 2085 | |
| Thr | Ala | Cys | Cys | Ala | Ala | Gly | Gly | Thr | Gly | Cys | Thr | Gly | Cys | Cys |
| | 2090 | | | | 2095 | | | | 2100 | |
| Ala | Ala | Thr | Thr | Thr | Ala | Thr | Thr | Thr | Gly | Ala | Ala | Ala | Ala | Ala |
| | 2105 | | | | 2110 | | | | 2115 | |
| Thr | Thr | Cys | Thr | Thr | Cys | Cys | Cys | Cys | Ala | Gly | Cys | Ala | Gly | Thr |
| | 2120 | | | | 2125 | | | | 2130 | |
| Thr | Cys | Ala | Thr | Ala | Cys | Ala | Gly | Ala | Ala | Gly | Ala | Cys | Cys | Ala |
| | 2135 | | | | 2140 | | | | 2145 | |
| Gly | Thr | Cys | Gly | Gly | Gly | Ala | Thr | Ala | Thr | Cys | Cys | Ala | Gly | Thr |
| | 2150 | | | | 2155 | | | | 2160 | |
| Ala | Thr | Gly | Gly | Thr | Gly | Gly | Ala | Gly | Gly | Cys | Thr | Ala | Thr | Gly |
| | 2165 | | | | 2170 | | | | 2175 | |
| Gly | Thr | Thr | Thr | Cys | Cys | Ala | Gly | Ala | Gly | Cys | Cys | Cys | Gly | Ala |
| | 2180 | | | | 2185 | | | | 2190 | |
| Ala | Thr | Thr | Gly | Ala | Thr | Gly | Cys | Ala | Cys | Gly | Gly | Ala | Thr | Thr |
| | 2195 | | | | 2200 | | | | 2205 | |
| Gly | Ala | Thr | Thr | Thr | Cys | Gly | Ala | Ala | Thr | Cys | Thr | Gly | Gly | Ala |
| | 2210 | | | | 2215 | | | | 2220 | |
| Ala | Gly | Gly | Ala | Thr | Ala | Ala | Ala | Gly | Ala | Ala | Ala | Gly | Ala | Ala |
| | 2225 | | | | 2230 | | | | 2235 | |
| Gly | Ala | Gly | Thr | Thr | Cys | Ala | Cys | Thr | Gly | Ala | Gly | Ala | Thr | Cys |
| | 2240 | | | | 2245 | | | | 2250 | |
| Ala | Thr | Gly | Ala | Ala | Gly | Ala | Thr | Cys | Thr | Gly | Thr | Thr | Cys | Cys |
| | 2255 | | | | 2260 | | | | 2265 | |
| Ala | Cys | Cys | Ala | Thr | Thr | Gly | Ala | Ala | Gly | Ala | Gly | Cys | Thr | Cys |
| | 2270 | | | | 2275 | | | | 2280 | |
| Ala | Gly | Ala | Cys | Gly | Gly | Cys | Ala | Ala | Ala | Ala | Thr | Ala | Gly | Gly |
| | 2285 | | | | 2290 | | | | 2295 | |
| Thr | Gly | Ala | Ala | Thr | Thr | Thr | Ala | Gly | Cys | Thr | Thr | Gly | Thr | Cys |
| | 2300 | | | | 2305 | | | | 2310 | |
| Cys | Thr | Thr | Cys | Ala | Thr | Gly | Ala | Ala | Ala | Ala | Ala | Thr | Ala | Gly |
| | 2315 | | | | 2320 | | | | 2325 | |
| Cys | Cys | Thr | Thr | Gly | Thr | Thr | Thr | Cys | Thr | Ala | Cys | Thr | | |
| | 2330 | | | | 2335 | | | | 2340 | |

<210> SEQ ID NO 7

```
<211> LENGTH: 16
<212> TYPE: PRT
<213> ORGANISM: Influenza A virus

<400> SEQUENCE: 7

Thr Gly Tyr Thr Met Asp Thr Val Asn Arg Thr His Gln Tyr Ser Glu
1               5                   10                  15

<210> SEQ ID NO 8
<211> LENGTH: 13
<212> TYPE: PRT
<213> ORGANISM: Influenza A virus

<400> SEQUENCE: 8

Asp Ser Thr Arg Lys Lys Ile Glu Lys Ile Arg Pro Leu
1               5                   10

<210> SEQ ID NO 9
<211> LENGTH: 4
<212> TYPE: PRT
<213> ORGANISM: Influenza A virus

<400> SEQUENCE: 9

Asn Glu Pro Ser
1

<210> SEQ ID NO 10
<211> LENGTH: 13
<212> TYPE: PRT
<213> ORGANISM: Influenza A virus

<400> SEQUENCE: 10

Thr Lys Asp Ala Glu Arg Gly Lys Leu Lys Arg Arg Ala
1               5                   10

<210> SEQ ID NO 11
<211> LENGTH: 6
<212> TYPE: PRT
<213> ORGANISM: Influenza A virus

<400> SEQUENCE: 11

Asn Thr Lys Trp Asn Glu
1               5

<210> SEQ ID NO 12
<211> LENGTH: 21
<212> TYPE: PRT
<213> ORGANISM: Influenza A virus

<400> SEQUENCE: 12

Gln Leu Glu Gly Phe Ser Ala Glu Ser Arg Lys Leu Leu Leu Ile Val
1               5                   10                  15

Gln Ala Leu Arg Asp
            20

<210> SEQ ID NO 13
<211> LENGTH: 12
<212> TYPE: PRT
<213> ORGANISM: Influenza A virus

<400> SEQUENCE: 13

Asp Leu Gly Gly Leu Tyr Glu Ala Ile Glu Glu Cys
1               5                   10
```

METHODS AND COMPOSITIONS RELATED TO INCREASING THE FIDELITY OF INFLUENZA A VIRUS FOR VACCINE DEVELOPMENT

This invention was made with government support under NIH/NIAID R21 AI112717-01 awarded by the National Institutes of Health. The Government has certain rights in the invention.

I. BACKGROUND

Yearly vaccination against influenza has been recently recommended by the CDC for all persons. Two different types of vaccination are currently available, the Live Attenuated Influenza Vaccine (LAIV) and the Trivalent Inactivated Vaccine (TIV). Both are multivalent and cover both Influenza A and B viruses believed to circulate in the population the following year. The comparative efficacy of LAIV and TIV has recently been examined in two meta-analyses—and LAIV has been shown to possess efficacy of 83% in children, while the efficacy of TIV was between 59-65%. LAIV has the added benefit of being administered through nasal spray in contrast to the injection based TIV. The combination of greater efficacy and nasal administration rather than intramuscular injection has led LAIV to be the preferred vaccine for children 2-8 years in Canada, Germany and the UK. Nevertheless, current live attenuated influenza vaccines (LAIV) are not sufficiently attenuated or stable for administration to children under the age of 2, pregnant women, persons with compromised immunity, persons with asthma, or persons at high risk for complications from influenza. However, these same groups of people are at high risk for complications from influenza. What are needed are new stable attenuated influenza viral strains for use in vaccines.

II. SUMMARY

Disclosed are methods and compositions related to mutant influenza viruses with increased fidelity. In one aspect, the disclosed mutant influenza viruses can increase the stability of existing Influenza virus vaccines.

In one aspect, disclosed herein are modified influenza A viruses comprising one or more mutations in the influenza RNA polymerase, wherein the one or more mutations causes an increased fidelity of the polymerase.

Also disclosed, in one aspect, are the modified influenza A virus of any preceding aspect, wherein the one or more mutations of the influenza RNA polymerase comprises at least one mutation in the PB1 and/or PA subunit of the RNA polymerase.

Also disclosed, in one aspect, are pharmaceutical composition comprising the modified influenza virus of any preceding aspect and methods of immunizing a subject against influenza virus; inducing an immune response to influenza virus in a subject; and/or inhibiting an influenza virus infection in a subject comprising administering to the subject the influenza virus and/or composition of any preceding aspect.

Also disclosed are recombinant nucleic acids encoding an influenza RNA polymerase with increased transcriptional fidelity wherein the RNA polymerase comprises at least one mutation selected from the PB1 and/or PA subunits of the RNA polymerase as well as vectors comprising the recombinant nucleic acid.

In one aspect, also disclosed are methods of increasing the immunogenicity of an attenuated influenza vaccine comprising obtaining an attenuated influenza vaccine viral strain and generating a mutation in the PB1 and/or PA subunit of the RNA polymerase of the influenza virus, wherein the mutation increases the fidelity of the RNA polymerase; and wherein an increase in fidelity of the polymerase increases the stability of the virus strain in a subject and reduces the amount mutant viruses formed during transcription of the virus thereby increasing the abundance of a single strain and as a result increases the immune response to the immunizing strain.

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A and 1B show the selected residues for initial mutation. The crystal structure of 4WSB was analyzed using PyMol and the desired mutations are visualized with respect to the nucleotide channel. Charge altering entrance mutants (PB1 -45R, 308K, 387K, and 391K) are highlighted in yellow and internal helix displacing mutations (PB1 -43V; PA-663R and 664K)(nonmutated residue indicated) are highlighted in red. PA is depicted in green, PB1 in can, and PB2 in pink. FIG. 1A shows the full crystal structure. FIG. 1B shows a view up through the nucleotide channel. FIG. 1C shows a closer view of the mutations in respect to the channel entrance.

Figure 2:
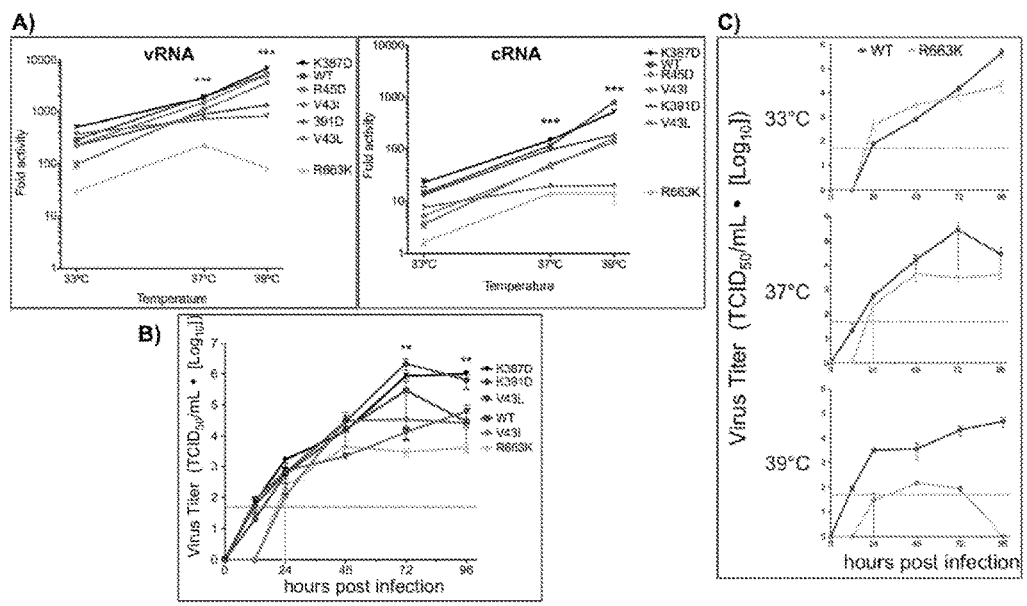

FIGS. 2A, 2B, and 2C show the temperature sensitivity of mutant viruses. FIG. 2A shows PA R663K is temperature sensitive by both transcription and replication based minigenomes. Confluent monolayers of 293T cells were co-transfected with pDZ plasmids encoding the control (guassia luciferase driven by CMV IE promoter). After 24hrs at 33, 37, or 39° C., cells were lysed with Passive Lysis Buffer (Promega) and luciferase levels were measured according to the manufacurer's instructions (Promega). Experiments were performed in triplicate and were independently repeated twice. Statistics were performed on GraphPad Prism (one-way ANOVA followed by Tukey's posttest). FIG. 2B shows K387D and K391D have increased titers at 96 and 72 hours respectively. Confluent monolayers of A549cells were infected at an MOI of 0.001 at 37° C. with the indicated viruses. 10% of the supernatant was harvested and replaced at the indicated time points. Samples were clarified by centrifugation and stored at −80° C. Viruses were tittered by $TCID_{50}$ on A549 cells and read by hemagglutination assay 5 days post infection. Statistics were performed on GraphPad Prism (two-way ANOVA followed by Bonferroni's post test). FIG. 2C shows that R663K is temperature sensitive. Assay was performed as in B with the following exception: after 1hr infection samples were placed at either 33, 37, or 39° C. Statistics were performed on GraphPad Prism (two-way ANOVA followed by Bonferroni's post test).

Figure 3:
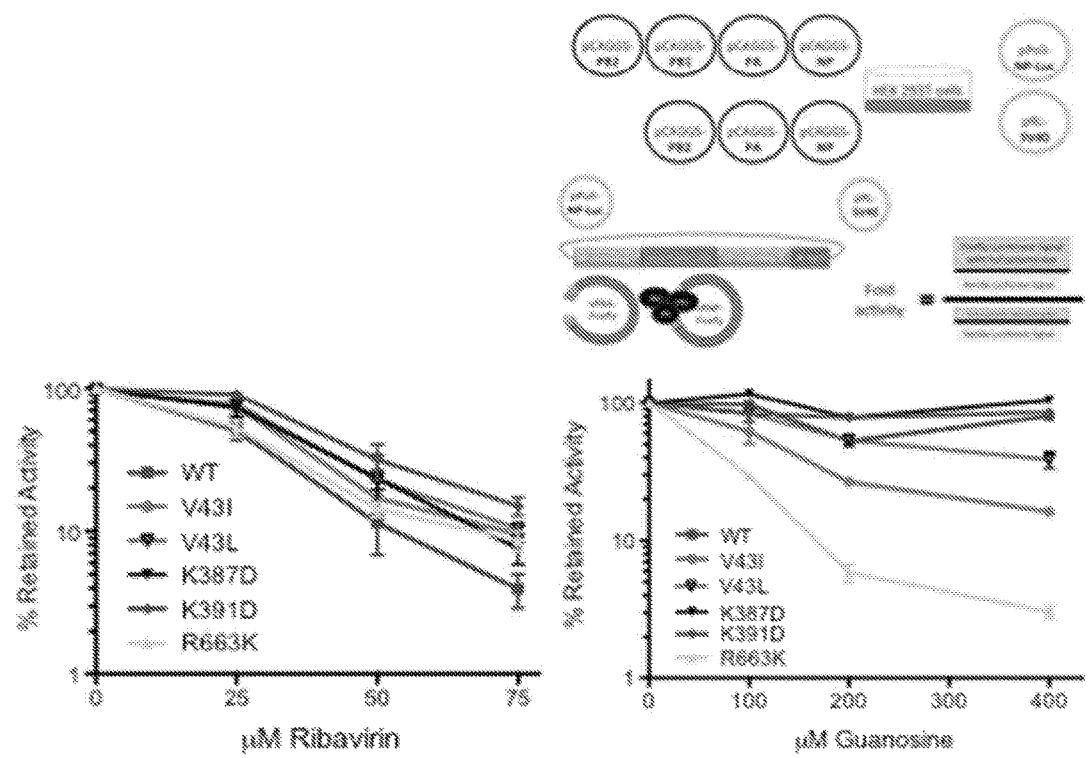

FIG. 3 shows the results of minigenome assays. Briefly, 293T cells were grown on poly D-lysine coated plates and transfected via PEI with 200 ng of each polymerase component. A luciferase reporter gene expressing the RNA of the coding region of firefly luciferase flanked by the non coding 3' and 5' sequence of influenza NP was used. The production of *Renilla* from a constituivitely active promoter was used as a control for cell density and transfection efficiency. Guanosine and Ribavirin were each added 3 hrs pretransfection and maintained for the course of the experiment. All activities were initially assayed as fold induction or the increase in activity over a -PB1 control. Activities were then then normalized to the 100% in the presence of no drug and the % retained titer was then calculated.

FIG. 4 shows virus drug resistance. A549 and MDCK cells were infected at a multiplicity of infection (MOI) of 0.1 for 1 h, washed once with PBS, and then cultured at 37° C. in DMEM containing 0.3% BSA and TPCK treated-trypsin at 1 μg/ml. The indicated drugs were added 3 hour pre-infection and maintained. Supernatant was harvested at 48 hours post infection and viral titers were determined via TCID-50 measurements as described by Reed and Muench. (1) Data is displayed as the decrease in titer from no drug.

FIG. 5 shows that nucleotide imbalance drives the increased activity of the mutant polymerase. Cells were incubated as in FIG. 2 with the following alterations. 293T cells were pretreated with 40 μM guanosine (A) or 40 μM guanosine and increasing concentrations of ribavirin (B). Fold induction was then normalized to activity at 0 μM guanosine (A) or 0 μM ribavirin/40 μM guanosine (B). Statistics were performed on GraphPad Prism (one-way ANOVA followed by Tukey's post test). ** $p<0.001$.

FIG. 6 shows the sequencing of viruses. MDCK cells were infected at an MOI of 0.05 with the indicated viruses and incubated at 37° C. 48 hours later supernatant was harvested a stock aliquotted for titering and RNA purified. Segment 8 was amplified and inserted in to a vector for clonal sanger sequencing. Only unique mutations detected in both the F and R reverse reads were counted.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular influenza virus, influenza virus polymerase, influenza virus polymerase PB1 subunit, or influenza virus polymerase PA subunit is disclosed and discussed and a number of modifications that can be made to a number of molecules including the influenza virus, influenza virus polymerase, influenza virus polymerase PB1 subunit, or influenza virus polymerase PA subunit are discussed, specifically contemplated is each and every combination and permutation of influenza virus, influenza virus polymerase, influenza virus polymerase PB1 subunit, or influenza virus polymerase PA subunit and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The influenza viral polymerase is a RNA-dependent RNA polymerase (RdRP) consisting of three subunits PB1, PB2, and PA and is responsible for the transcription and replication of the viral genome. RNA viruses have long been assumed to have polymerases high error rate as epitomized by HIV-1. The large number of errors of the RNA polymerase results in inaccurate replication of the RNA transcript. This high error rate of the polymerase is referred to as low fidelity; where fidelity is a relative measure of the ability of a polymerase to accurately copy the nucleic acid template. A polymerase with low fidelity has a high error rate and a polymerase with high fidelity has a small error rate. This compounded with a poor to nonexistent proofreading ability of the polymerase can lead to mutations in immunogenic epitopes and ultimately viral escape. Hence, the majority of newly manufactured influenza viruses are mutants; which causes antigenic drift, that is, a slow change in the antigens on the viral surface over time.

As noted above, the low fidelity of the influenza virus polymerase is largely responsible for antigenic drift of an influenza virus. The antigenic drift makes preventing, inhibiting, or treating influenza particularly troublesome as mutants which have changes at antigenic epitopes can escape host immune responses. Also, due to the low fidelity of the polymerase, live attenuated influenza vaccine (LAIV) can be unstable. Fidelity altering mutations are normally associated with effects on the binding of either viral template nucleic acids or incoming nucleotides, and several high fidelity virus mutants are shown herein to be attenuated in vivo, likely due to their inability to respond to selective pressures in the host. As a result, alterations to fidelity have been used to create novel vaccine candidate described herein. In one aspect, disclosed herein are modified influenza A viruses comprising one or more mutations in the influenza RNA polymerase, wherein the one or more mutations causes an increased fidelity of the polymerase.

As used throughout, any influenza A virus can be modified to comprise a PB1 or PA subunit with one or more mutations disclosed herein. For example, the influenza A virus can be selected from the group consisting of an H2N2 virus, an H3N2 virus, an H1N1 virus, an H9N2 virus and an H5N1 virus. Optionally, the influenza A virus can be selected from the group consisting of A/Puerto Rico/9/1934 (H1N1), A/Ann Arbor/6/60, A/California/04/2009, A/bat/Guatemala/060/2010(H17N10), A/Wisconsin/22/201 1 and A/Quail/Hong Kong/Gl/97. The influenza A virus can also be an avian influenza A virus. These include, but are not limited to, A/Chi cken/Nanchang/3-120/01 H3N2, A/Hong Kong/485/1997(H5N1), A/Anhui/1/2013 (H7N9) and A/Shanghai/1/2013 (H7N9). It is understood and herein contemplated that the PB1 and PA polymerase subunits have strain variants. Accordingly, all mutation locations disclosed herein are based on the position of a reference PB1 or PA sequence from A/Puerto Rico/9/1934 (H1N1) referred to herein as PR8 strain. It is understood and herein contemplated that the skilled artisan can easily identify the corresponding residue from any other influenza viral strain.

In addition to the disclosed mutations to PB1 and PA, resassortant influenza A viruses comprising one or more genomic segments from one or more influenza A viruses are also contemplated. More specifically, the virus includes genetic and/or polypeptide components derived from more than one parental viral strain or source. For example, a 7:1 reassortant includes 7 viral genomic segments (or gene segments) derived from a first parental virus and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus. Optionally, reassortant viruses are produced by introducing vectors including the six internal genes of a viral strain selected for its favorable properties regarding vaccine production, in combination with the genome segments encoding the surface antigens (HA and NA) of a selected, e.g., pathogenic strain. For example, the HA segment can be selected from an HI, H3 or B strain, as is routinely performed for vaccine production. Similarly, the HA segment can be selected from other pathogenic strains such as an H2 strain (e.g., H2N2), an H5 strain (e.g., H5N1), an H7 strain (e.g., H7N7) or an H9 strain (H9N2). In certain modified viruses, the internal gene segments are derived from the influenza PR8 strain.

Herein a "mutation" refers to a non-naturally occurring change in the nucleic acid or amino acid sequence and is produced by human intervention (e.g., by mutagenesis of cloned DNA, RNA, cDNA, or amino acid sequences), such as induced point mutation, deletion, insertion and substitution mutants. Amino acid sequence mutations typically fall into one or more of three classes: substitutional, insertional or deletional mutations.

Not every mutation in PB1, PB2, or PA will affect the polymerase activity in a manner that will increase fidelity. Specifically contemplated are mutations of the RNA polymerase subunits that increase fidelity. The increase in fidelity can be due to a difference in the side chain in the mutated residue which constricts the entry to the nucleotide channel or constricts the channel itself or alters the charge at the entry of or within the channel. The increase in fidelity can also occur due to conformational change in the binding pocket which alters which amino acid side chains are exposed and changes contact residues thus constricting the channel or changing charges. It is understood and herein contemplated that mutations that result in a change in the size of a side chain can also negatively affect fidelity by preventing or significantly effecting the rate of transcription or replication if too large (low to no fidelity because little to no transcription or replication), or increases access to the template binding pocket such that transcription and replication have lower fidelity. It is also that a mutation that results in a change in charge, hydrophobicity, or polarity can reduce binding of the template strand significantly enough to stop transcription or replication or decrease fidelity. Moreover, mutations that are located in regions of the subunit spatially removed from the template groove may not have an effect on fidelity.

The mutation(s) of the modified viruses disclosed herein can be in any subunit of the influenza viral polymerase, for example, the PB1, PB2, and/or PA subunit. Thus, in one aspect, disclosed herein are herein are modified influenza A viruses comprising one or more mutations in the influenza RNA polymerase, wherein the one or more mutations of the influenza RNA polymerase comprises at least one mutation in the PB1 and/or PA subunit of the RNA polymerase, and wherein the one or more mutations causes an increased fidelity of the polymerase.

In one aspect, the one or more mutations of the influenza RNA polymerase can comprise a mutation in the PB1 subunit. In one aspect, the one or more mutations can be located at a residue corresponding to residues 36, 37, 38, 39, 40, 41, 42, 43, 44, 45, 46, 47, 48, 49, 50, 77, 78, 79, 80, 228, 229, 230, 231, 232, 233, 234, 235, 236, 237, 238, 239, 240, 306, 307, 308, 309, 310, 311, 383, 384, 385, 386, 387, 388, 389, 390, 391, 392, 393, 394, 395, 480, and/or 481 of SEQ ID NO: 4. For example, disclosed herein are modified influenza viruses comprising at least one mutation at one or more residues of the PB1 subunit, wherein the mutated residue corresponds to residues 43, 45, 235, 237, 239, 308, 387, 391, 480, and/or 481 of SEQ ID NO: 4, and wherein the mutation increases fidelity of the influenza RNA polymerase.

PB1 is a 757 amino acid enzyme and is the minimum structural component of the influenza viral RNA polymerase and is necessary for functionality. The secondary structure of the PB1 subunit is comprised of alpha helices, loops, beta sheets, and a beta stem loop. In one aspect, disclosed herein are modified influenza viruses comprising at least one mutation at one or more residues of an alpha helix of the PB1 subunit of the influenza RNA polymerase. It is understood and herein contemplated that PB1 has a number of alpha helices in its secondary structure. For example, there is an alpha helix located at the residues of the PB1 subunit corresponding to residues 36 to 50 of SEQ ID NO: 4, as well as, an alpha helix located at the residues of the PB1 subunit corresponding to residues 383 to 395 of SEQ ID NO: 4. Thus, the modified influenza virus can comprise a RNA polymerase with one or more mutations corresponding to residues 36, 37, 38, 39, 40, 41, 42, 43, 44, 45, 46, 47, 48, 49, 50, 383, 384, 385, 386, 387, 388, 389, 390, 391, 392, 393, 394, and/or 395 of the PB1 subunit of the influenza virus RNA polymerase as set forth in SEQ ID NO: 4. However, the mutation is not a Valine to Isoleucine substitution at a residue corresponding to residue 43 of SEQ ID NO: 4 when only one fidelity increasing mutation is present. For example, disclosed herein are modified influenza viruses comprising one or more mutations in the influenza RNA polymerase, wherein the one or more mutations of the influenza RNA polymerase comprises at least one mutation in the PB1 or PA subunit of the RNA polymerase, wherein the influenza RNA polymerase comprises a mutation at one or more residues of an alpha helix of the PB1 subunit of the influenza RNA polymerase as set forth in SEQ ID NO: 4, wherein the influenza RNA polymerase comprises a mutation at one or more residues of the alpha helix corresponding to residues 36 to 50 of the alpha helix of the PB1 subunit as set forth in SEQ ID NO: 4, wherein the one or more mutations causes an increased fidelity of the polymerase, wherein when one or more mutations is a single substitution at a residue corresponding to residue 43 of SEQ ID NO: 4, the substitution at residue 43 is not a Valine to Isoleucine substitution.

Also disclosed are modified influenza viruses comprising at least one mutation at one or more residues of a loop of the PB1 subunit of the influenza RNA polymerase as set forth in SEQ ID NO: 4, wherein the one or more mutations causes an increased fidelity of the polymerase. It is understood and herein contemplated that PB1 has a number of loops in its secondary structure. For example, there is are loops located at the residues of the PB1 subunit corresponding to residues 77 to 80, 228 to 240, and 306 to 311 as set forth in SEQ ID NO: 4. Thus, the modified influenza virus can comprise a RNA polymerase with one or more mutations in one or more loops located at a residue corresponding to residues 77, 78, 79, 80, 228, 229, 230, 231, 232, 233, 234, 235, 236, 237, 238, 239, 240, 306, 307, 308, 309, 310, and/or 311 of the PB1 subunit of the influenza virus RNA polymerase as set forth in SEQ ID NO: 4. In one aspect, disclosed herein are modified influenza viruses comprising at least one mutation at one or more residues of a loop of the PB1 subunit of the influenza RNA polymerase as set forth in SEQ ID NO: 4, wherein the mutation is at one or more residues corresponding to residues 235, 237, 239, and/or 308 as set forth in SEQ ID NO: 4.

It is also contemplated herein that the particular mutation of the modified influenza virus polymerase may not be associated with any known secondary structure of PB1. For example, the mutation can be at a residue corresponding to residues 480 and/or 481 of the PB1 subunit of the influenza virus RNA polymerase as set forth in SEQ ID NO: 4. Thus, in one aspect, disclosed herein are modified influenza viruses comprising at least one mutation at one or more residues of PB1, wherein the mutation is at a residue corresponding to residues 480 and/or 481 of PB1.

It is contemplated herein that any of the PB1 mutations disclosed herein can be used in combination with any of the other PB1 mutations disclosed herein as well as any of the PA mutations disclosed. For example, the modified influenza viruses can comprise an RNA polymerase comprising one or more mutations of the PB1 subunit wherein the mutations comprise a mutation in an alpha helix corresponding to residues 36 to 50 as set forth in SEQ ID NO: 4 and a mutation in an alpha helix corresponding to residues 383 to 395 as set forth in SEQ ID NO: 4; a mutation in an alpha helix corresponding to residues 36 to 50 as set forth in SEQ ID NO: 4 and a mutation in a loop corresponding to residues 77 to 80 as set forth in SEQ ID NO: 4; a mutation in an alpha helix corresponding to residues 36 to 50 as set forth in SEQ ID NO: 4 and a mutation in a loop corresponding to residues 228 to 240 as set forth in SEQ ID NO: 4; a mutation in an alpha helix corresponding to residues 36 to 50 as set forth in SEQ ID NO: 4 and a mutation in a loop corresponding to residues 306 to 311 as set forth in SEQ ID NO: 4; a mutation in an alpha helix corresponding to residues 36 to 50 as set forth in SEQ ID NO: 4 and a mutation corresponding to residues 480 and/or 481 as set forth in SEQ ID NO: 4; a mutation in an alpha helix corresponding to residues 383 to 395 as set forth in SEQ ID NO: 4 and a mutation in a loop corresponding to residues 77 to 80 as set forth in SEQ ID NO: 4; a mutation in an alpha helix corresponding to residues 383 to 395 as set forth in SEQ ID NO: 4 and a mutation in a loop corresponding to residues 228 to 240 as set forth in SEQ ID NO: 4; a mutation in an alpha helix corresponding to residues 383 to 395 as set forth in SEQ ID NO: 4 and a mutation in a loop corresponding to residues 306 to 311 as set forth in SEQ ID NO: 4; a mutation in an alpha helix corresponding to residues 383 to 395 as set forth in SEQ ID NO: 4 and a mutation corresponding to residues 480 and/or 481 as set forth in SEQ ID NO: 4; a mutation in a loop corresponding to residues 77 to 80 as set forth in SEQ ID NO: 4 and a mutation in a loop corresponding to residues 228 to 240 as set forth in SEQ ID NO: 4; a mutation in a loop corresponding to residues 77 to 80 as set forth in SEQ ID NO: 4 and a mutation in a loop corresponding to residues 306 to 311 as set forth in SEQ ID NO: 4; a mutation in a loop corresponding to residues 77 to 80 as set forth in SEQ ID NO: 4 and a mutation corresponding to residues 480 and/or 481 as set forth in SEQ ID NO: 4; a mutation in a loop corresponding to residues 228 to 240 as set forth in SEQ ID NO: 4 and a mutation in a loop corresponding to residues 306 to 311 as set forth in SEQ ID NO: 4; a mutation in a loop corresponding to residues 228 to 240 as set forth in SEQ ID NO: 4 and a mutation corresponding to residues 480 and/or 481 as set forth in SEQ ID NO: 4; and a mutation in a loop corresponding to residues 306 to 311 as set forth in SEQ ID NO: 4 and a mutation corresponding to residues 480 and/or 481 as set forth in SEQ ID NO: 4.

It is further contemplated herein that the multiple mutations can occur within the same secondary structure. For example, disclosed herein are modified influenza viruses comprising an RNA polymerase comprising one or more mutations in the alpha helix corresponding to residues 36 to 50 of the PB1 subunit as set forth in SEQ ID NO: 4, one or more mutations in the alpha helix corresponding to residues 383 to 395 of the PB1 subunit as set forth in SEQ ID NO: 4; one or more mutations in the loop corresponding to residues 77 to 80 of the PB1 subunit as set forth in SEQ ID NO: 4, one or more mutations in the loop corresponding to residues 228 to 240 of the PB1 subunit as set forth in SEQ ID NO: 4, and/or one or more mutations in the loop corresponding to residues 306 to 311 of the PB1 subunit as set forth in SEQ ID NO: 4.

In one aspect, the one or more mutations of the influenza RNA polymerase can comprise a mutation in the PA subunit. In one aspect, the one or more mutations can be located at a residue corresponding to residues 654, 655, 656, 657, 658, 659, 660, 661, 662, 663, 664, 665, 666, 667, 668, 669, 670, 671, 672, 673, 674, 682, 683, 684, 685, 686, 687, 688, 689, 690, 691, 692, and/or 693 of the PA subunit of the influenza virus RNA polymerase as set forth in SEQ ID NO: 3. For example, disclosed herein are modified influenza viruses comprising at least one mutation at one or more residues of the PA subunit, wherein the mutated residue corresponds to residues 661, 663, 664, and/or 691 of SEQ ID NO: 3, and wherein the mutation increases fidelity of the influenza RNA polymerase.

PA is a 716 amino acid enzyme. PA comprises the endonuclease activity of the RNA polymerase and is promotes the formation of the trimeric polymerase complex. The secondary structure of the PA subunit is comprised of alpha helices, loops, and beta sheets. In one aspect, disclosed herein are modified influenza viruses comprising at least one mutation at one or more residues of an alpha helix of the PA subunit of the influenza RNA polymerase as set forth in SEQ ID NO: 3. It is understood and herein contemplated that PA has a number of alpha helices in its secondary structure. For example, there is an alpha helix located at the residues of the PA subunit corresponding to residues 654 to 674 of SEQ ID NO: 3, as well as, an alpha helix located at the residues of the PA subunit corresponding to residues 682 to 693 of SEQ ID NO: 3. Thus, the modified influenza virus can comprise a RNA polymerase with one or more mutations corresponding to residues 654, 655, 656, 657, 658, 659, 660, 661, 662, 663, 664, 665, 666, 667, 668, 669, 670, 671, 672, 673, 674, 682, 683, 684, 685, 686, 687, 688, 689, 690, 691, 692, and/or 693 of the PA subunit as set forth in SEQ ID NO: 3, wherein the one or more mutations causes an increase in the fidelity of the RNA polymerase.

It is contemplated herein that any of the PA mutations disclosed herein can be used in combination with any of the other PA mutations disclosed herein as well as any of the PB1 mutations disclosed. For example, the modified influenza viruses can comprise an RNA polymerase comprising one or more mutations of the PA subunit wherein the mutations comprise one or more mutations in an alpha helix corresponding to residues 654 to 674 as set forth in SEQ ID NO: 3 and/or one or more mutations in an alpha helix corresponding to residues 682 to 693 as set forth in SEQ ID NO: 3. For example, the one or more mutations can comprise a mutation at any combination of two or more residues two or more corresponding to residues 661, 663, 664, and/or 691 of SEQ ID NO: 3, wherein the one or more mutations causes an increase in the fidelity of the RNA polymerase.

As stated throughout this disclosure, the disclosed modified influenza virus can comprise any combination mutation in the PB1 and PA subunits disclosed herein. Thus, in one aspect, disclosed herein are modified influenza viruses comprising one or more mutations in the PB1 subunit of the RNA polymerase further comprising one or more mutations at one or more residues of the PA subunit of the RNA polymerase, wherein the mutations of the RNA polymerase causes an increase in fidelity of the polymerase. For example, disclosed herein are modified influenza viruses comprising one or more mutations of the PB1 subunit of the RNA polymerase including but not limited to a mutation in the alpha helix corresponding to residues 36 to 50 of SEQ ID NO: 4, a mutation in the alpha helix corresponding to residues 383 to 395 of SEQ ID NO: 4, a mutation in the loop corresponding to residues 77 to 80 of SEQ ID NO: 4, a mutation in the loop corresponding to residues 228 to 240 of SEQ ID NO: 4, a mutation in the loop corresponding to residues 306 to 311 of SEQ ID NO: 4, and/or a mutation in the residues corresponding to residues 480 and/or 481 as set forth in SEQ ID NO: 4, further comprising one or more mutations in the alpha helix corresponding to residues 654 to 674 of SEQ ID NO: 3, and/or a mutation in the alpha helix corresponding to residues 682 to 693 of SEQ ID NO: 3, wherein the mutations of the RNA polymerase causes an increase in fidelity of the polymerase. Also disclosed are modified influenza viruses comprising one or more mutations of the PB1 subunit of the influenza virus RNA polymerase including, but not limited to, a mutation at a residue corresponding to 36, 37, 38, 39, 40, 41, 42, 43, 44, 45, 46, 47, 48, 49, 50, 77, 78, 79, 80, 228, 229, 230, 231, 232, 233, 234, 235, 236, 237, 238, 239, 240, 306, 307, 308, 309, 310, 311, 383, 384, 385, 386, 387, 388, 389, 390, 391, 392, 393, 394, 395, 480, and/or 481 as set forth in SEQ ID NO: 4 further comprising one or more mutations of the PA subunit of the influenza virus RNA polymerase including but not limited to a mutation at a residue corresponding to 654, 655, 656, 657, 658, 659, 660, 661, 662, 663, 664, 665, 666, 667, 668, 669, 670, 671, 672, 673, 674, 682, 683, 684, 685, 686, 687, 688, 689, 690, 691, 692, and/or 693 as set forth in SEQ ID NO: 3.

As discussed herein there are numerous variants of the PB1 protein and PA protein that are known and herein contemplated. In addition, to the known functional PB1 and PA strain variants there are derivatives of the PB1 and PA proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA, RAN, or cDNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA, RNA, or cDNA encoding the protein, thereby producing DNA, RNA, or cDNA encoding the variant, and thereafter expressing the DNA, RNA, or cDNA in recombinant cell culture. Techniques for making substitution mutations at predetermined sites in DNA having a known sequence are well known, for example M13 primer mutagenesis and PCR mutagenesis.

Amino acid substitutions are typically of single residues, but can occur at a number of different locations at once for example in one, two, three, four, five, six, seven or more amino acids of the polypeptide sequence set forth as SEQ ID NOs: 1, 2, 3, or 4; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative Substitutions, others are known in the art.

| | |
|---|---|
| Ala | Ser, Gly, Cys |
| Arg | Lys; Gln, Met, Ile |
| Asn | Gln; His, Glu, Asp |
| Asp | Glu, Asn, Gln |
| Cys | Ser, Net, Thr |
| Gln | Asn, Lys, Glu, Asp |
| Glu | Asp, Asn, Gln |
| Gly | Pro, Ala |
| His | Asn; Gln |
| Ile | Leu; Val, Met |
| Leu | Ile; Val, Met |
| Lys | Arg; Gln, Met, Ile |
| Met | Leu; Ile, Val |
| Phe | Met; Leu; Tyr, Trp, His |
| Ser | Thr, Met, Cys |
| Thr | Ser, Met, Val |
| Trp | Tyr, Phe |
| Tyr | Trp; Phe, His |
| Val | Ile; Leu, Met |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

In one aspect contemplated herein are modified influenza viruses comprising one or more mutations at one or more residues of the alpha helix of the PB1 subunit of the influenza virus RNA polymerase corresponding to residues 36 to 50 as set forth in SEQ ID NO: 4 (TGYTMDTVN-RTHQYSE SEQ ID NO: 7), wherein the one or more mutations causes an increase in the fidelity of the RNA polymerase, wherein the mutation is a substitution corresponding to residue 43, and wherein the substitution is a Valine to another hydrophobic non-polar amino acid residue including, but not limited to Glycine (V43G), Alanine (V43A), Leucine (V43L), Methionine (V43M), Isoleucine (V43I), Proline (V43P), Phenylalanine (V43F), and Tryptophan (V43W), wherein the substitution is not Valine to Isoleucine when the modified influenza virus comprises only one fidelity increasing substitution. For example, disclosed herein are modified influenza viruses comprising a Valine to Leucine substation at the residue corresponding to residue 43 (V43L) as set forth in SEQ ID NO: 4.

Also disclosed herein are modified influenza viruses comprising one or more mutations at one or more residues of the alpha helix of the PB1 subunit of the influenza virus RNA polymerase corresponding to residues 36 to 50 of SEQ ID NO: 4 (TGYTMDTVNRTHQYSE SEQ ID NO: 7), wherein the one or more mutations causes an increase in the fidelity of the RNA polymerase, wherein the mutation is a substitution corresponding to residue 45, and wherein the substitution is a Arginine to another charged amino acid including, but not limited to Lysine (R45K), Histidine (R45H), Aspartic Acid (R45D), and Glutamic acid (R45E). Alternatively, the substitution can be a Arginine to Glutamine (R45Q) substitution. For example, disclosed herein are modified influenza virus comprising a Arginine to Lysine or Arginine to Aspartic Acid substitution at the PB1 residue corresponding to residue 45 as set forth in SEQ ID NO: 4.

Also disclosed herein are modified influenza viruses comprising one or more mutations at one or more residues of the alpha helix of the PB1 subunit of the influenza virus RNA polymerase corresponding to residues 383 to 395 of SEQ ID NO: 4 (DSTRKKIEKIRPL SEQ ID NO: 8), wherein the one or more mutations causes an increase in the fidelity of the RNA polymerase, wherein the mutation is a substitution corresponding to residue 387 or 391, and wherein the substitution is a Lysine to another charged amino acid including, but not limited to Arginine (K387R and K391R), Histidine (K387H and K391H), Aspartic Acid (K387D and K391D), and Glutamic acid (K387E).

Also disclosed herein are modified influenza viruses comprising one or more mutations at one or more residues of the loop of the PB1 subunit of the influenza virus RNA polymerase corresponding to residues 77 to 80 of SEQ ID NO: 4 (NEPS SEQ ID NO: 9), wherein the one or more mutations causes an increase in the fidelity of the RNA polymerase.

Also disclosed herein are modified influenza viruses comprising one or more mutations at one or more residues of the loop of the PB1 subunit of the influenza virus RNA polymerase corresponding to residues 228 to 240 of SEQ ID NO: 4 (TKDAERGKLKRRA SEQ ID NO: 10), wherein the one or more mutations causes an increase in the fidelity of the RNA polymerase, wherein the mutation is a substitution corresponding to residue 235 or 237, and wherein the substitution is a Lysine to another charged amino acid including, but not limited to Arginine (K235R and K237R), Histidine (K235H and K237H), Aspartic Acid (K235D and K237D), and Glutamic acid (K235E and K237E).

Also disclosed herein are modified influenza viruses comprising one or more mutations at one or more residues of the alpha helix of the PB1 subunit of the influenza virus RNA polymerase corresponding to residues 228 to 240 of SEQ ID NO: 4 (TKDAERGKLKRRA SEQ ID NO: 10), wherein the one or more mutations causes an increase in the fidelity of the RNA polymerase, wherein the mutation is a substitution corresponding to residue 239, and wherein the substitution is a Arginine to another charged amino acid including, but not limited to Lysine (R239K), Histidine (R239H), Aspartic Acid (R239D), and Glutamic acid (R239E). Alternatively, the substitution can be an Arginine to Glutamine (R239Q) substitution.

Also disclosed herein are modified influenza viruses comprising one or more mutations at one or more residues of the loop of the PB1 subunit of the influenza virus RNA polymerase corresponding to residues 306 to 311 of SEQ ID NO: 4 (NTKWNE SEQ ID NO: 11), wherein the one or more mutations causes an increase in the fidelity of the RNA polymerase, wherein the mutation is a substitution corresponding to residue 308, and wherein the substitution is a Lysine to another charged amino acid including, but not limited to Arginine (K308R), Histidine (K308H), Aspartic Acid (K308D), and Glutamic acid (K308E).

Also disclosed herein are modified influenza viruses comprising one or more mutations at one or more residues of the PB1 subunit of the influenza virus RNA polymerase corresponding to residues 480 or 481 of SEQ ID NO: 4, wherein the one or more mutations causes an increase in the fidelity of the RNA polymerase, wherein the mutation is a substitution corresponding to residue 480 or 481, and wherein the substitution is a Lysine to another charged amino acid including, but not limited to Arginine (K480R and K481R), Histidine (K480H and K481H), Aspartic Acid (K480D and K481D), and Glutamic acid (K480E and K481E).

Also disclosed herein are modified influenza viruses comprising one or more mutations at one or more residues of the alpha helix of the PA subunit of the influenza virus RNA polymerase corresponding to residues 654-674 of SEQ ID NO: 3 (QLEGFSAESRKLLLIVQALRD SEQ ID NO: 12), wherein the one or more mutations causes an increase in the fidelity of the RNA polymerase, wherein the mutation is a substitution corresponding to residue 661, and wherein the substitution is a Glutamic Acid to another charged amino acid including, but not limited to Arginine (E661R), Histidine (E661H), Aspartic Acid (E661D), and Lysine (E661K) or is a Glutamic Acid to Glutamine (E661Q) substitution.

Also disclosed herein are modified influenza viruses comprising one or more mutations at one or more residues of the alpha helix of the PA subunit of the influenza virus RNA polymerase corresponding to residues 654-674 of SEQ ID NO: 3 (QLEGFSAESRKLLLIVQALRD SEQ ID NO: 12), wherein the one or more mutations causes an increase in the fidelity of the RNA polymerase, wherein the mutation is a substitution corresponding to residue 663, and wherein the substitution is a Arginine to another charged amino acid including, but not limited to Lysine (R663K), Histidine (R663H), Aspartic Acid (R663D), and Glutamic acid (R663E). Alternatively, the substitution can be an Arginine to Glutamine (R663Q) substitution. For example, disclosed herein are modified influenza virus comprising a Arginine to Lysine (R663K) or Arginine to Glutamic Acid (R663E) substitution at the PA residue corresponding to residue 663 of SEQ ID NO: 3.

Also disclosed herein are modified influenza viruses comprising one or more mutations at one or more residues of the alpha helix of the PA subunit of the influenza virus RNA polymerase corresponding to residues 654-674 of SEQ ID NO: 3 (QLEGFSAESRKLLLIVQALRD SEQ ID NO: 12), wherein the one or more mutations causes an increase in the fidelity of the RNA polymerase, wherein the mutation is a substitution corresponding to residue 664, and wherein the substitution is a Lysine to another charged amino acid including, but not limited to Arginine (K664R), Histidine (K664H), Aspartic Acid (K664D), and Glutamic acid (K664E). For example, disclosed herein are modified influenza virus comprising a Lysine to Glutamic Acid (K665E) substitution at the PA residue corresponding to residue 664 of SEQ ID NO: 3.

Also disclosed herein are modified influenza viruses comprising one or more mutations at one or more residues of the alpha helix of the PA subunit of the influenza virus RNA polymerase corresponding to residues 682 to 693 of SEQ ID NO: 3 (DLGGLYEAIEEC SEQ ID NO: 13), wherein the one or more mutations causes an increase in the fidelity of the RNA polymerase, wherein the mutation is a substitution corresponding to residue 691, and wherein the substitution is a Glutamic Acid to another charged amino acid including, but not limited to Arginine (E661R), Histidine (E661H), Aspartic Acid (E661D), and Lysine (E661K) or is a Glutamic Acid to Glutamine (E661Q) substitution.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T.E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 6 sets forth a particular nucleic acid sequence of PB1 and SEQ ID NO: 4 sets forth a particular sequence of a PB1 protein. Specifically disclosed are variants of PB1 and PA and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO: 4 is set forth in SEQ ID NO:6 and one of the many nucleic acid sequences that can encode the protein sequence set forth in SEQ ID NO: 3 is set forth in SEQ ID NO: 5. In addition, for example, a disclosed conservative derivative of SEQ ID NO: 4 where the valine (V) at position 43 is changed to a leucine (L). It is understood that for this mutation all of the nucleic acid sequences that encode this particular derivative of the PB1 or PA are also disclosed including for example degenerate nucleic acid sequences that encode the particular polypeptide set forth in SEQ ID NOs: 1, 2, 3, and 4. It is also understood that while no amino acid sequence indicates what particular DNA, cDNA, or RNA sequence encodes that protein within a vector, cell, or organism, where particular variants of a disclosed protein are disclosed herein, the known nucleic acid sequence that encodes that protein in the particular PB1 and PA are also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH—$, $—CH_2S—$, $—CH_2—CH_2—CH=CH—$ (cis and trans), $—COCH_2—CH(OH)CH_2—$, and $—CHH_2SO—$ (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., *Int J Pept Prot Res* 14:177-185 (1979) ($—CH_2NH—$, $CH_2CH_2—$); Spatola et al. *Life Sci* 38:1243-1249 (1986) ($—CHH_2—S$); Hann, *J. Chem. Soc Perkin Trans.* I 307-314 (1982) ($—CH—CH—$, cis and trans); Almquist et al. *J. Med. Chem.* 23:1392-1398 (1980) ($—COCH_2—$); Jennings-White et al. *Tetrahedron Lett* 23:2533 (1982) ($—COCH_2—$); Szelke et al. *European Appln*, EP 45665 CA (1982): 97:39405 (1982) ($—CH(OH)CH_2—$); Holladay et al. *Tetrahedron. Lett* 24:4401-4404 (1983) ($—C(OH)CH_2—$); and Hruby *Life Sci* 31:189-199 (1982) ($—CH_2—S—$); each of which is incorporated herein by reference. A particularly preferred non-peptide linkage is $—CH_2NH—$. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

In one aspect, also disclosed herein are recombinant nucleic acids encoding an influenza RNA polymerase with increased transcriptional fidelity wherein the RNA polymerase comprises at least one mutation selected from the PB1 or PA subunits of the RNA polymerase. It is understood that the disclosed recombinant nucleic acids can encode any of the PB1 or PA mutant polymerase subunits disclosed herein. As used throughout, the term recombinant means that the material (e.g., a nucleic acid or protein) has been artificially or synthetically (non-naturally) altered by human intervention. It is understood that, when referring to a virus, e.g., an influenza A virus, the virus is recombinant when it is produced by the expression of a recombinant nucleic acid.

For example, disclosed herein are recombinant nucleic acids wherein the mutation of the PB1 or PA subunit of the influenza RNA polymerase comprises a mutation of at least one residue selected from one or more residues of the alpha helix corresponding to residues 36 to 50 or residues 383 to 395 of the PB1 subunit of the influenza RNA polymerase as set forth in SEQ ID NO: 4; one or more residues of the loop formed by the amino acids corresponding to residues 77-80 of the PB1 subunit of the influenza RNA polymerase as set forth in SEQ ID NO: 4; one or more residues of the loop formed by the amino acids corresponding to residues 228-240 of the PB1 subunit of the influenza RNA polymerase as set forth in SEQ ID NO: 4; one or more residues of the loop formed by the amino acids corresponding to residues 306-311 of the PB1 subunit of the influenza RNA polymerase as set forth in SEQ ID NO: 4; residues 480 or 481 of the PB1 subunit of the influenza RNA polymerase as set forth in SEQ ID NO: 4; and one or more residues of the alpha helix corresponding to residues 654 to 674 or residues 682 to 693 of the PA subunit of the influenza virus RNA polymerasse as set forth in SEQ ID NO: 3. For example, also disclosed are recombinant nucleic acids encoding one or more mutations of the PB1 subunit of the RNA polymerase including but not limited to a mutation at a residue corresponding to 36, 37, 38, 39, 40, 41, 42, 43, 44, 45, 46, 47, 48, 49, 50, 77, 78, 79, 80, 228, 229, 230, 231, 232, 233, 234, 235, 236, 237, 238, 239, 240, 306, 307, 308, 309, 310, 311, 383, 384, 385, 386, 387, 388, 389, 390, 391, 392, 393, 394, 395, 480, and/or 481 of SEQ ID NO: 4 and/or comprising one or more mutations of the PA subunit of the RNA polymerase including but not limited to a mutation at a residue corresponding to 654, 655, 656, 657, 658, 659, 660, 661, 662, 663, 664, 665, 666, 667, 668, 669, 670, 671, 672, 673, 674, 682, 683, 684, 685, 686, 687, 688, 689, 690, 691, 692, and/or 693 of SEQ ID NO: 3.

In one aspect contemplated herein recombinant nucleic acids encoding one or more mutations at one or more residues of the alpha helix of the PB1 subunit of the influenza virus RNA polymerase corresponding to residues 36 to 50 of SEQ ID NO: 4 (TGYTMDTVNRTHQYSE SEQ ID NO: 7), wherein the one or more mutations causes an increase in the fidelity of the RNA polymerase, wherein the mutation is a substitution corresponding to residue 43, and wherein the substitution is a Valine to another hydrophobic non-polar amino acid residue including, but not limited to Glycine (V43G), Alanine (V43A), Leucine (V43L), Methionine (V43M), Isoleucine (V43I), Proline (V43P), Phenylalanine (V43F), and Tryptophan (V43W), wherein the substitution is not Valine to Isoleucine when the modified influenza virus comprises only one fidelity increasing substitution. For example, disclosed herein are recombinant nucleic acids encoding a Valine to Leucine substitution at the residue corresponding to residue 43 (V43L) as set forth in SEQ ID NO: 4.

Also disclosed herein are recombinant nucleic acids encoding one or more mutations at one or more residues of the alpha helix of the PB1 subunit of the influenza virus RNA polymerase corresponding to residues 36 to 50 of SEQ ID NO: 4 (TGYTMDTVNRTHQYSE SEQ ID NO: 7), wherein the one or more mutations causes an increase in the fidelity of the RNA polymerase, wherein the mutation is a substitution corresponding to residue 45, and wherein the substitution is a Arginine to another charged amino acid including, but not limited to Lysine (R45K), Histidine (R45H), Aspartic Acid (R45D), and Glutamic acid (R45E). Alternatively, the substitution can be a Arginine to Glutamine (R45Q) substitution. For example, disclosed herein are modified influenza virus comprising a Arginine to Lysine or Arginine to Aspartic Acid substitution at the PB1 residue corresponding to residue 45 of SEQ ID NO: 4.

Also disclosed herein are recombinant nucleic acids encoding one or more mutations at one or more residues of the alpha helix of the PB1 subunit of the influenza virus RNA polymerase corresponding to residues 383 to 395 of SEQ ID NO: 4 (DSTRKKIEKIRPL SEQ ID NO: 8), wherein the one or more mutations causes an increase in the fidelity of the RNA polymerase, wherein the mutation is a substitution corresponding to residue 387 or 391, and wherein the substitution is a Lysine to another charged amino acid including, but not limited to Arginine (K387R and K391R), Histidine (K387H and K391H), Aspartic Acid (K387D and K391D), and Glutamic acid (K387E).

Also disclosed herein are recombinant nucleic acids encoding one or more mutations at one or more residues of the loop of the PB1 subunit of the influenza virus RNA polymerase corresponding to residues 77 to 80 of SEQ ID NO: 4 (NEPS SEQ ID NO: 9), wherein the one or more mutations causes an increase in the fidelity of the RNA polymerase.

Also disclosed herein are recombinant nucleic acids encoding one or more mutations at one or more residues of the loop of the PB1 subunit of the influenza virus RNA polymerase corresponding to residues 228 to 240 of SEQ ID NO: 4 (TKDAERGKLKRRA SEQ ID NO: 10), wherein the one or more mutations causes an increase in the fidelity of the RNA polymerase, wherein the mutation is a substitution corresponding to residue 235 or 237, and wherein the substitution is a Lysine to another charged amino acid including, but not limited to Arginine (K235R and K237R), Histidine (K235H and K237H), Aspartic Acid (K235D and K237D), and Glutamic acid (K235E and K237E).

Also disclosed herein are recombinant nucleic acids encoding one or more mutations at one or more residues of the alpha helix of the PB1 subunit of the influenza virus RNA polymerase corresponding to residues 228 to 240 of SEQ ID NO: 4 (TKDAERGKLKRRA SEQ ID NO: 10), wherein the one or more mutations causes an increase in the fidelity of the RNA polymerase, wherein the mutation is a substitution corresponding to residue 239, and wherein the substitution is a Arginine to another charged amino acid including, but not limited to Lysine (R239K), Histidine (R239H), Aspartic Acid (R239D), and Glutamic acid (R239E). Alternatively, the substitution can be an Arginine to Glutamine (R239Q) substitution.

Also disclosed herein are recombinant nucleic acids encoding one or more mutations at one or more residues of the loop of the PB1 subunit of the influenza virus RNA polymerase corresponding to residues 306 to 311 of SEQ ID NO: 4 (NTKWNE SEQ ID NO: 11), wherein the one or more mutations causes an increase in the fidelity of the RNA polymerase, wherein the mutation is a substitution corresponding to residue 308, and wherein the substitution is a Lysine to another charged amino acid including, but not limited to Arginine (K308R), Histidine (K308H), Aspartic Acid (K308D), and Glutamic acid (K308E).

Also disclosed herein are recombinant nucleic acids encoding one or more mutations at one or more residues of the PB1 subunit of the influenza virus RNA polymerase corresponding to residues 480 or 481 of SEQ ID NO: 4, wherein the one or more mutations causes an increase in the fidelity of the RNA polymerase, wherein the mutation is a substitution corresponding to residue 480 or 481, and wherein the substitution is a Lysine to another charged amino acid including, but not limited to Arginine (K480R and K481R), Histidine (K480H and K481H), Aspartic Acid (K480D and K481D), and Glutamic acid (K480E and K481E).

Also disclosed herein are recombinant nucleic acids encoding one or more mutations at one or more residues of the alpha helix of the PA subunit of the influenza virus RNA polymerase corresponding to residues 654-674 of SEQ ID NO: 3 (QLEGFSAESRKLLLIVQALRD SEQ ID NO: 12), wherein the one or more mutations causes an increase in the fidelity of the RNA polymerase, wherein the mutation is a substitution corresponding to residue 661, and wherein the substitution is a Glutamic Acid to another charged amino acid including, but not limited to Arginine (E661R), Histidine (E661H), Aspartic Acid (E661D), and Lysine (E661K) or is a Glutamic Acid to Glutamine (E661Q) substitution.

Also disclosed herein are recombinant nucleic acids encoding one or more mutations at one or more residues of the alpha helix of the PA subunit of the influenza virus RNA polymerase corresponding to residues 654-674 of SEQ ID NO: 3 (QLEGFSAESRKLLLIVQALRD SEQ ID NO: 12), wherein the one or more mutations causes an increase in the fidelity of the RNA polymerase, wherein the mutation is a substitution corresponding to residue 663, and wherein the substitution is a Arginine to another charged amino acid including, but not limited to Lysine (R663K), Histidine (R663H), Aspartic Acid (R663D), and Glutamic acid (R663E). Alternatively, the substitution can be an Arginine to Glutamine (R663Q) substitution. For example, disclosed herein are modified influenza virus comprising a Arginine to Lysine (R663K) or Arginine to Glutamic Acid (R663E) substitution at the PA residue corresponding to residue 663 of SEQ ID NO: 3.

Also disclosed herein are recombinant nucleic acids encoding one or more mutations at one or more residues of the alpha helix of the PA subunit of the influenza virus RNA polymerase corresponding to residues 654-674 of SEQ ID NO: 3 (QLEGFSAESRKLLLIVQALRD SEQ ID NO: 12), wherein the one or more mutations causes an increase in the fidelity of the RNA polymerase, wherein the mutation is a substitution corresponding to residue 664, and wherein the substitution is a Lysine to another charged amino acid including, but not limited to Arginine (K664R), Histidine (K664H), Aspartic Acid (K664D), and Glutamic acid (K664E). For example, disclosed herein are recombinant nucleic acids encoding a Lysine to Glutamic Acid (K665E) substitution at the PA residue corresponding to residue 664 of SEQ ID NO: 3.

Also disclosed herein are recombinant nucleic acids encoding one or more mutations at one or more residues of the alpha helix of the PA subunit of the influenza virus RNA polymerase corresponding to residues 682 to 693 of SEQ ID NO: 3 (DLGGLYEAIEEC SEQ ID NO: 13), wherein the one or more mutations causes an increase in the fidelity of the RNA polymerase, wherein the mutation is a substitution corresponding to residue 691, and wherein the substitution is a Glutamic Acid to another charged amino acid including, but not limited to Arginine (E661R), Histidine (E661H), Aspartic Acid (E661D), and Lysine (E661K) or is a Glutamic Acid to Glutamine (E661Q) substitution.

The recombinant nucleic acids disclosed herein can be in any vector that can be used for the production of influenza virus in a host cell. Accordingly, in one aspect, disclosed herein are vectors comprising any recombinant nucleic acid disclosed herein. The vector can direct the in vivo or in vitro synthesis of any of the polypeptides described herein, including, but not limited to PB1 and/or PA polymerase subunits. One or more of the vectors described herein can be part of a multi-vector system used to produce an influenza A virus. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene (See generally, Sambrook et al. (2001)). The vector, for example, can be a plasmid. The vectors can contain genes conferring hygromycin resistance, ampicillin resistance, gentamicin resistance, neomycin resistance or other genes or phenotypes suitable for use as selectable markers.

As used throughout, a host cell is a cell that contains one or more of the nucleic acids disclosed herein, including any of the nucleic acids in a vector, and supports the replication and/or expression of the nucleic acids, and optionally production of one or more encoded products including a polypeptide and/or a virus. Host cells can be prokaryotic cells, such as E. coli, or eukaryotic cells, such as yeast, insect, amphibian, avian or mammalian cells, including human cells. Examples of host cells include, but are not limited to, Vera (African green monkey kidney) cells, Per.C6 cells (human embryonic retinal cells), BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), CEK cells, primary human lung cells, bronchial epithelial cells, COS cells (e.g., COS1, COS7 cells) and any other mammalian or avian cells that can be used to produce or propagate an influenza virus. The term host cell encompasses combinations or mixtures of cells including, but not limited to mixed cultures of different cell types or cell lines.

There are a variety of molecules disclosed herein that are nucleic acid based, including for example the recombinant nucleic acids that encode, for example PB1 or PA, as well as various functional nucleic acids. As used herein, nucleic acid refers to single or multiple stranded molecules which can be DNA or RNA, or any combination thereof, including modifications to those nucleic acids. For example, the nucleic acid can be a cDNA. The nucleic acid may represent a coding strand or its complement, or any combination thereof. The nucleic acid can be directly cloned into an appropriate vector, or if desired, can be modified to facilitate the subsequent cloning steps. Such modification steps are routine, an example of which is the addition of oligonucleotide linkers which contain restriction sites to the termini of the nucleic acid. General methods are set forth in in Sambrook et al. (2001) Molecular Cloning—A Laboratory Manual (3rd ed.) Vol. 1-3, Cold Spring Harbor Laboratory, Cold Spring Harbor Press, NY, (Sambrook).

The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687, 808, Englisch et al., Angewandte Chemie, International Edition, 1991, 30, 613, and Sanghvi, Y. S., Chapter 15, *Antisense Research and Applications*, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. 2' sugar modifications also include but are not limited to —O[$(CH_2)_n$ O]$_m$ $CH_3$, —O$(CH_2)_n$ OCH$_3$, —O$(CH_2)_n$ NH$_2$, —O$(CH_2)_n$ $CH_3$, —O$(CH_2)_n$—ONH$_2$, and —O$(CH_2)_n$ON [$(CH_2)_n$ $CH_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included.

It is understood that nucleotide analogs need only contain a single modification, but may also contain multiple modifications within one of the moieties or between different moieties.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

It is understood and herein contemplated that the mutations to the PB1 and/or PA subunit of the influenza viral polymerase can be used to increase the immunogenicity of an influenza vaccine including but not limited to trivalent influenza vaccines, and live attenuated influenza vaccines, as well as, influenza vaccine strains that have proven to be genetically unstable including, but not limited to, influenza strains comprising the PB2 K637E, N265S, E65G, P112S, N556D, and/or Y658H substitutions.

Therefore, in one aspect, disclosed herein are methods of increasing the immunogenicity of an attenuated influenza vaccine comprising obtaining an attenuated influenza vaccine viral strain and generating a mutation in the PB1 or PA subunit of the RNA polymerase of the influenza virus, wherein the mutation increases the fidelity of the RNA polymerase; and wherein an increase in fidelity of the polymerase increases the stability of the virus strain in a subject and reduces the amount mutant viruses formed during transcription of the virus thereby increasing the abundance of a single strain and as a result increases the immune response to the immunizing strain. For example, disclosed herein are methods of increasing the immunogenicity of an attenuated influenza vaccine, wherein the mutation of the PB1 or PA subunit of the influenza RNA polymerase comprises a mutation at least one residue selected from one or more residues of the alpha helix corresponding to residues 36 to 50 or residues 383 to 395 of the PB1 subunit as set forth in SEQ ID NO: 4; at mutation at one or more residues of the loop formed by the amino acids corresponding to residues 77-80 as set forth in SEQ ID NO: 4; a mutation at one or more residues of the loop formed by the amino acids corresponding to residues 228-240 as set forth in SEQ ID NO: 4; a mutation at one or more residues of the loop formed by the amino acids corresponding to residues 306-311 as set forth in SEQ ID NO: 4; a mutation at residues 480 or 481 as set forth in SEQ ID NO: 4; a mutation one or more residues of the alpha helix corresponding to residues 654 to 674 and/or a mutation at residues corresponding to 682 to 693 of the PA subunit as set forth in SEQ ID NO: 3.

In one aspect, disclosed herein are pharmaceutical compositions comprising any of the modified influenza viruses or recombinant nucleic acids disclosed herein. For example, disclosed herein are pharmaceutical compositions comprising one or more modified influenza viruses comprising one or more mutations in the PB1 subunit of the RNA polymerase further comprising one or more mutations at one or more residues of the PA subunit of the RNA polymerase, wherein the mutations of the RNA polymerase causes an increase in fidelity of the polymerase. For example, disclosed herein are pharmaceutical compositions comprising one or more modified influenza viruses comprising one or more mutations of the PB1 subunit of the RNA polymerase including but not limited to a mutation in the alpha helix corresponding to residues 36 to 50 of SEQ ID NO: 4, the alpha helix corresponding to residues 383 to 395 of SEQ ID NO: 4, the loop corresponding to residues 77 to 80 of SEQ ID NO: 4, the loop corresponding to residues 228 to 240 of SEQ ID NO: 4, the loop corresponding to residues 306 to 311 of SEQ ID NO: 4, and/or residues corresponding to residues 480 and/or 481 as set forth in SEQ ID NO: 4 and/or comprising one or more mutations in the alpha helix corresponding to residues 654 to 674 of SEQ ID NO: 3, and/or the alpha helix corresponding to residues 682 to 693 of SEQ ID NO: 3, wherein the mutations of the RNA polymerase causes an increase in fidelity of the polymerase. Also disclosed are pharmaceutical compositions comprising one or more modified influenza viruses comprising one or more mutations of the PB1 subunit of the RNA polymerase including but not limited to a mutation at a residue corresponding to 36, 37, 38, 39, 40, 41, 42, 43, 44, 45, 46, 47, 48, 49, 50, 77, 78, 79, 80, 228, 229, 230, 231, 232, 233, 234, 235, 236, 237, 238, 239, 240, 306, 307, 308, 309, 310, 311, 383, 384, 385, 386, 387, 388, 389, 390, 391, 392, 393, 394, 395, 480, and/or 481 of SEQ ID NO: 4 and/or comprising one or more mutations of the PA subunit of the RNA polymerase including but not limited to a mutation at a residue corresponding to 654, 655, 656, 657, 658, 659, 660, 661, 662, 663, 664, 665, 666, 667, 668, 669, 670, 671, 672, 673, 674, 682, 683, 684, 685, 686, 687, 688, 689, 690, 691, 692, and/or 693 of SEQ ID NO: 3.

Also disclosed herein are pharmaceutical compositions comprising one or more recombinant nucleic acids encoding one or more mutations of the PB1 subunit of the RNA polymerase including but not limited to a mutation in the alpha helix corresponding to residues 36 to 50 of SEQ ID NO: 4, the alpha helix corresponding to residues 383 to 395 of SEQ ID NO: 4, the loop corresponding to residues 77 to 80 of SEQ ID NO: 4, the loop corresponding to residues 228 to 240 of SEQ ID NO: 4, the loop corresponding to residues 306 to 311 of SEQ ID NO: 4, and/or residues corresponding to residues 480 and/or 481 as set forth in SEQ ID NO: 4 and/or encoding one or more mutations in the alpha helix corresponding to residues 654 to 674 of SEQ ID NO: 3, and/or the alpha helix corresponding to residues 682 to 693 of SEQ ID NO: 3, wherein the mutations of the RNA polymerase causes an increase in fidelity of the polymerase.

Also disclosed are pharmaceutical compositions comprising one or more recombinant nucleic acids encoding one or more mutations of the PB1 subunit of the RNA polymerase including but not limited to a mutation at a residue corresponding to 36, 37, 38, 39, 40, 41, 42, 43, 44, 45, 46, 47, 48, 49, 50, 77, 78, 79, 80, 228, 229, 230, 231, 232, 233, 234, 235, 236, 237, 238, 239, 240, 306, 307, 308, 309, 310, 311, 383, 384, 385, 386, 387, 388, 389, 390, 391, 392, 393, 394, 395, 480, and/or 481 of SEQ ID NO: 4 and/or encoding one or more mutations of the PA subunit of the RNA polymerase including but not limited to a mutation at a residue corresponding to 654, 655, 656, 657, 658, 659, 660, 661, 662, 663, 664, 665, 666, 667, 668, 669, 670, 671, 672, 673, 674, 682, 683, 684, 685, 686, 687, 688, 689, 690, 691, 692, and/or 693 of SEQ ID NO: 3.

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, subcutaneously, extracorporeally, topically or the like, including topical intranasal administration or administration by inhalant or nebulization, or installation via bronchoscopy. As used herein, "topical intranasal administration" or "intranasally" means delivery of the compositions into the nose and nasal passages through one or both of the nares and can comprise delivery by a spraying mechanism or droplet mechanism, or through aerosolization of the nucleic acid or vector. Optionally, the composition is administered by oral inhalation, nasal inhalation or intranasal mucosal administration. That is, administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

The compositions, including modified influenza viruses and recombinant nucleic acids disclosed herein can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be orally, parenterally (e.g., intravenously), by intramuscular injection, by intraperitoneal injection, transdermally, subcutaneuously, extracorporeally, topically (including ophthalmically, vaginally, rectally, intranasally), or the like, including topical intranasal administration or administration by inhalant or nebulization, or installation via bronchoscopy. As used herein, "topical intranasal administration" or "intranasally" means delivery of the compositions into the nose and nasal passages through one or both of the nares and can comprise delivery by a spraying mechanism or droplet mechanism, or through aerosolization of the nucleic acid or vector. Optionally, the composition is administered by oral inhalation, nasal inhalation or intranasal mucosal administration. That is, administration of the compositions by inhalant can be through the nose or mouth via delivery by a spraying or droplet mechanism. Delivery can also be directly to any area of the respiratory system (e.g., lungs) via intubation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The disclosed pharmaceutical compositions, modified influenza viruses and recombinant nucleic acids can be used as therapeutic or prophylactic vaccines to elicit a protective or therapeutic immune response against influenza virus. In one aspect, disclosed herein are methods of immunizing a subject against influenza virus comprising administering to the subject any of the pharmaceutical compositions, recombinant nucleic acids, or modified influenza viruses disclosed herein. Also disclosed are methods of inducing an immune response against influenza virus in a subject comprising administering to the subject any of the modified influenza viruses, recombinant nucleic acids, or pharmaceutical compositions disclosed herein.

It is understood and herein contemplated that the elicitation of a protective or therapeutic immune response can inhibit an influenza virus infection in a subject. Thus, in one aspect, disclosed herein are methods of inhibiting an influenza virus infection in a subject comprising administering to the subject any of the modified influenza viruses, recombinant nucleic acids, or pharmaceutical compositions disclosed herein.

As used herein the terms treatment, treat, or treating refers to a method of reducing one or more of the effects of the infection or one or more symptoms of the infection by eliciting an immune response in the subject. Thus in the disclosed method, treatment can refer to a 10%, 20%, 30%, 40%, 50%, 60%, 70%, 80%, 90%, or 100% reduction in the severity of an established infection or a symptom of the infection. For example, a method for treating an infection is considered to be a treatment if there is a 10% reduction in one or more symptoms of the infection in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection or disease or symptoms of the infection or disease.

As used herein, the terms prevent, preventing, and prevention of an infection, refers to an action, for example, administration of a therapeutic agent (e.g., a composition disclosed herein), that occurs before or at about the same time a subject begins to show one or more symptoms of the infection, which inhibits or delays onset or exacerbation or delays recurrence of one or more symptoms of the infection. As used herein, references to decreasing, reducing, or inhibiting include a change of 10%>, 20%>, 30%>, 40%>, 50%>, 60%>, 70%), 80%), 90%) or greater relative to a control level. For example, the disclosed methods are considered to be a prevention if there is about a 10%> reduction in onset, exacerbation or recurrence of infection, or symptoms of infection in a subject exposed to an infection when compared to control subjects exposed to an infection that did not receive a composition for decreasing infection. Thus, the reduction in onset, exacerbation or recurrence of infection can be about a 10, 20, 30, 40, 50, 60, 70, 80, 90, 100%, or any amount of reduction in between as compared to control subjects. For example, and not to be limiting, if about 10% of the subjects in a population do not become infected as compared to subjects that did not receive preventive treatment, this is considered prevention. Similarly, as used herein, "inhibit" or "inhibition" refers to any decreased change in viral growth, replication, or spread that decreases the virulence of a virus. Inhibition can commence after antigenic exposure. Inhibition can comprise a change of 10%>, 20%>, 30%>, 40%>, 50%>, 60%>, 70%>, 80%>, 90%> or greater relative to a control level. For example, the disclosed methods are considered to be a inhibition if there is about a 10%> reduction in onset, exacerbation, or recurrence of infection, replication rate of a virus, viral spread, or symptoms of infection in a subject exposed to an infection when compared to control subjects exposed to an infection that did not receive a composition for decreasing infection.

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an the modified influenza virus, vaccine comprising a modified influenza virus, recombinant PB1 and/or recombinant PA, for treating, inhibiting, or preventing an influenza infection, the efficacy of the modified influenza virus, vaccine comprising a modified influenza virus, recombinant PB1 and/or recombinant PA can be assessed in various ways well known to the skilled practitioner. For instance, one of ordinary skill in the art will understand that a composition, such as an the modified influenza virus, vaccine comprising a modified influenza virus, recombinant PB1 and/or recombinant PA, disclosed herein is efficacious in treating or inhibiting an influenza infection in a subject by observing that the composition reduces viral load of a challenge virus or actual infection or prevents a further increase in viral load. Viral loads can be measured by methods that are known in the art, for example, using polymerase chain reaction assays to detect the presence of Influenza nucleic acids or antibody assays to detect the presence of Influenza proteins in a sample (e.g., but not limited to, blood) from a subject or patient, or by measuring the level of circulating anti-Influenza antibody levels in the patient.

The compositions such as, the modified influenza virus, vaccine comprising a modified influenza virus, recombinant PB1 and/or recombinant PA, that are disclosed herein may be administered prophylactically to patients or subjects who are at risk for being exposed to Influenza virus or who have been newly exposed to Influenza virus. In subjects who have been newly exposed to Influenza virus but who have not yet displayed the presence of the virus (as measured by PCR or other assays for detecting the virus) in blood or other body fluid, efficacious treatment with a modified influenza virus, vaccine comprising a modified influenza virus, recombinant PB1 and/or recombinant PA partially or completely inhibits the appearance of the virus in the blood or other body fluid.

As used throughout, a subject can be a vertebrate, more specifically a mammal (e.g., a human, horse, cat, dog, cow, pig, sheep, goat, mouse, rabbit, rat, non-human primate, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with or at risk of developing an influenza infection. The term patient or subject includes human and veterinary subjects.

C. Methods Of Making The Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins, such as SEQ ID NO: 4, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant GA (1992) *Synthetic Peptides: A User Guide*. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) *FEBS Lett.* 307:97-101; Clark-Lewis I et al., *J. Biol. Chem.*, 269:16075 (1994); Clark-Lewis I et al., *Biochemistry*, 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

3. Process Claims for Making the Compositions

Disclosed are processes for making the compositions as well as making the intermediates leading to the compositions. For example, disclosed are nucleic acids in SEQ ID NO: 5 and/or SEQ ID NO: 6. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO: 5 and/or SEQ ID NO: 6 and a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO: 5 and/or SEQ ID NO: 6, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth SEQ ID NO: 5 and/or SEQ ID NO: 6 and a sequence controlling the expression of the nucleic acid.

Disclosed are nucleic acid molecules produced by the process comprising linking in an operative way a nucleic acid molecule comprising a sequence encoding a protein set forth in SEQ ID NO: 3 and/or SEQ ID NO: 4 and a sequence controlling an expression of the nucleic acid molecule.

Disclosed are nucleic acid molecules produced by the process comprising linking in an operative way a nucleic acid molecule comprising a sequence encoding a protein having 80% identity to a peptide set forth in SEQ ID NO: 3 and/or SEQ ID NO: 4 and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID NO: 3 and/or SEQ ID NO: 4, wherein any change from SEQ ID NO: 3 and/or SEQ ID NO: 4 are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed proteins or peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

D. Examples

1. Example 1: Rational Design of High Fidelity Mutant Viruses

Disclosed herein is the discovery of several high fidelity virus variants which are attenuated in mice. These mutants were selected using the mutagenic purine analog, ribavirin, and have a single amino acid substitution within a putative nucleotide influx channel in the viral polymerase—indicating the possibility that the nucleotide influx channel may regulate virus fidelity. Disclosed herein is a panel of 11 mutants that map to the putative nucleotide influx channel, and have characterized their replicative properties. By doing so, a number of mutations were identified which confer altered nucleotide selectivity both in vitro and in vivo—as well as viable virus mutants that mediate protection against challenge with wild-type influenza virus in mice.

Novel Influenza A Virus (IAV) polymerase mutants with altered nucleotide selectivity were identified in vitro using the crystal structure of IAV. Through the crystal structure, it was shown that viruses possessing these mutations have altered nucleotide selectivity in cell culture. Herein, the initial mutations at the nucleotide entry channel are analyzed using additional nucleoside analogs in minigenome, viral growth and polymerase activity assays. Second generation of mutations with greater impacts on fidelity are also created and tested herein.

IAV was passaged in the presence of ribavirin and selected a novel high fidelity virus. The ribavirin resistance was traced to a V34I mutation in the PB1 segment, which lies far from the active site (>100A) but close to a putative nucleotide entry channel. Based on the enzyme structure, it was hypothesize that the PB1 V43I mutation displaces an alpha helix and extrudes lysine at residue 387 and 391 into the channel which may constrict nucleotide influx (FIG. 1).

To study this channel further, additional mutations were made that fall into three categories: (i) mutations at PB1 residue 43 that are intended to constrict the channel (ii) mutations that alter the charge at the entry of the channel and (iii) PA mutations intended to constrict the channel (Table 3). First generation mutants were tested for activity in polymerase based minigenome assays and saw that 6 of them (V43I, V43L, R45D, K387D, K391D, and R663K) had greater than 1% activity compared to wt. The activity of these polymerases was examined in closer detail. Minigenome assays were performed with both a vRNA (viral transcription only) and cRNA (requiring replication of the reporter gene as well as viral transcription) based viral specific reporter gene and saw that PA R663K exhibited mild temperature sensitivity with both. (FIG. 2A).

TABLE 3

Selected Residues for mutation

| 1st Generation | PB1 V43I, V43L, R45K, R45D, K308D, K387D, K391D |
| --- | --- |
| | PA R663E, R663K, K664E |
| 2$^{nd}$ Generation | PB1 K235, K237, K239, K480, K481 |
| | PA E661, E691 |

Viruses were rescued with and without these mutations and virus multi-cycle growth kinetics were analyzed in A549 cells at 37° C. PR8 possessing K387D or K391D exhibited elevated growth at 37° C. compared to WT virus (FIG. 2B). All other first generation mutations did not significantly affect growth kinetics (measured by two-way ANOVA). However, PR8 possessing K at PA 663 was significantly temperature sensitive with reduced viral titers at 39° C. at all time points tested (FIG. 2C). The other mutations did not significantly affect the growth kinetics of PR8.

Mice were infected with these mutant viruses to determine if any possessed altered attenuation or impaired immunogenicity. All viruses indeed had improved attenuation (safety) as compared to WT PR8, while retaining levels of immunogenicity that were close to the wild-type virus (Table 4).

TABLE 4

All of the nucleotide channel viruses are safer than wt PR9 and maintain immunogenicity.

| Priming Virus | LD-50, FFU | Geometric mean (SD) HAI titer, reciprocal serum dilution: |
| --- | --- | --- |
| PR8 WT | 30 | 2050 (0) |
| PR8 PB1 V43I | 30 | 1500 (590) |
| PR8 PB1 V43L | 600 | 390 (340) |
| PR8 PB1 K387D | 100 | 680 (360) |

TABLE 4-continued

All of the nucleotide channel viruses are safer than wt PR9 and maintain immunogenicity.

| Priming Virus | LD-50, FFU | Geometric mean (SD) HAI titer, reciprocal serum dilution: |
| --- | --- | --- |
| PR8 PB1 K391D | 150 | 720 (290) |
| PR8 PA R663K | 300 | 510 (320) |
| PBS | — | <16 (0) |

C57 BL/6 mice (n = 5) were inoculated intranasally with 10, 100, and 1000 FFU of the indicated viruses in 30 μL after mild avertin anesthetization as described. Sera was collected at 12 days postinfection. Eight hemagglutinating units (HAU) of WT PR8 were incubated with 2-fold serial dilutions of the indicated sera. Weight loss and clinical signs of distress were measured daily. Mice were euthanized upon losing 30% of their initial body weight or displaying clinical signs of distress. Depicted is the mean lethal dose and the geometric mean of the hemagglutination inhibition of the mice infected with 10 FFU. Mean lethal dose (LD50) was calculated with the survival data from above using the method of Reed and Muench.

Figure 4:
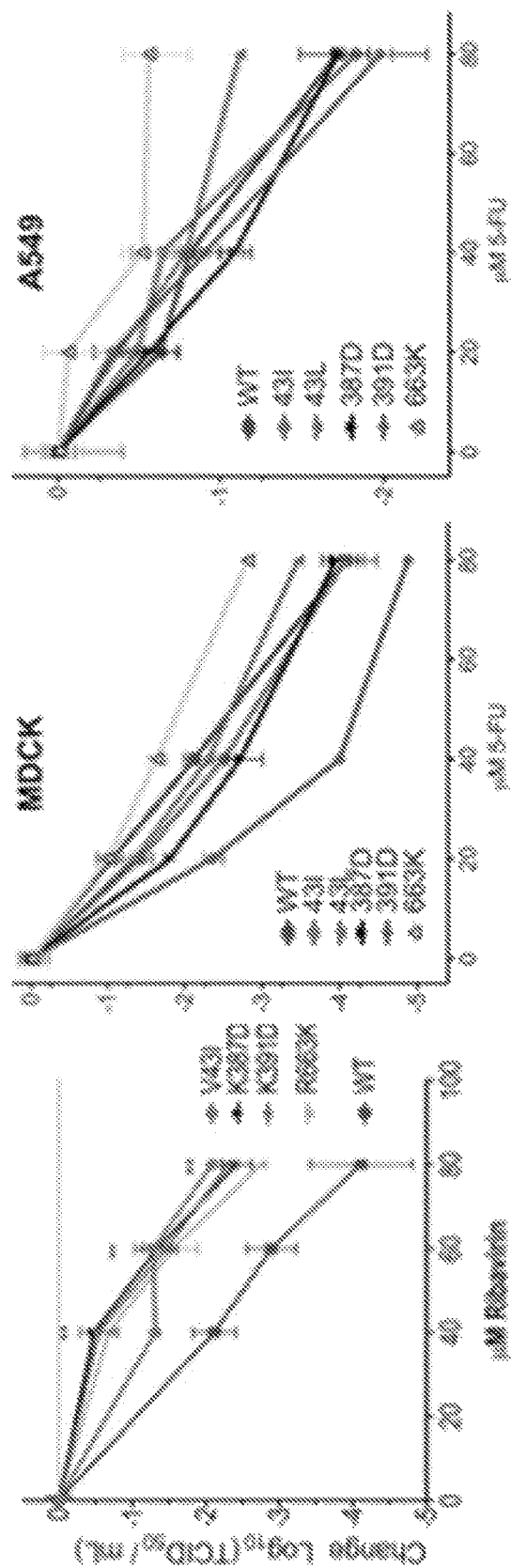

Studies were initiated with the intention of assessing the effects of the various polymerase mutants on enzyme fidelity. Mutants were tested to determine whether they conferred resistance to the drug, ribavirin, which inhibits influenza virus replication in large part by (i) depleting the cellular GTP pool (through its competition with cellular inosine monophosphate for IMP dehydrogenase) and (ii) promoting viral mutagenesis. Briefly, minigenome assays were conducted in the presence of ribavirin (at 0-75 μM). It was found that polymerase complexes containing PB1 mutations V43I, K387D, and K391D exhibited greater activity than WT in the presence of ribavirin (FIGS. 3 and 4), indicating that these mutations convey resistance to ribavirin-mediated inhibition.

The effects of the mutations on the nucleotide selectivity of the viral polymerase was also tested. To do this, minigenome assays were conducted in the presence of high levels of exogenous guanosine. Excess guanosine inhibits influenza polymerase activity, likely through the creation of unbalanced intracellular NTP pools (with increased GTP and reduced ATP). Polymerases with greater nucleotide selectivity were expected to have reduced activity under these conditions. FIG. 3 shows the polymerase complex containing the PB1 V43I mutation exhibited a greater reduction of polymerase activity in the presence of excess guanosine, compared to the wild-type polymerase. The PA R663K mutation also conferred a similar phenotype—although this mutation resulted in even greater sensitivity to inhibition by excess guanosine.

Figure 5:
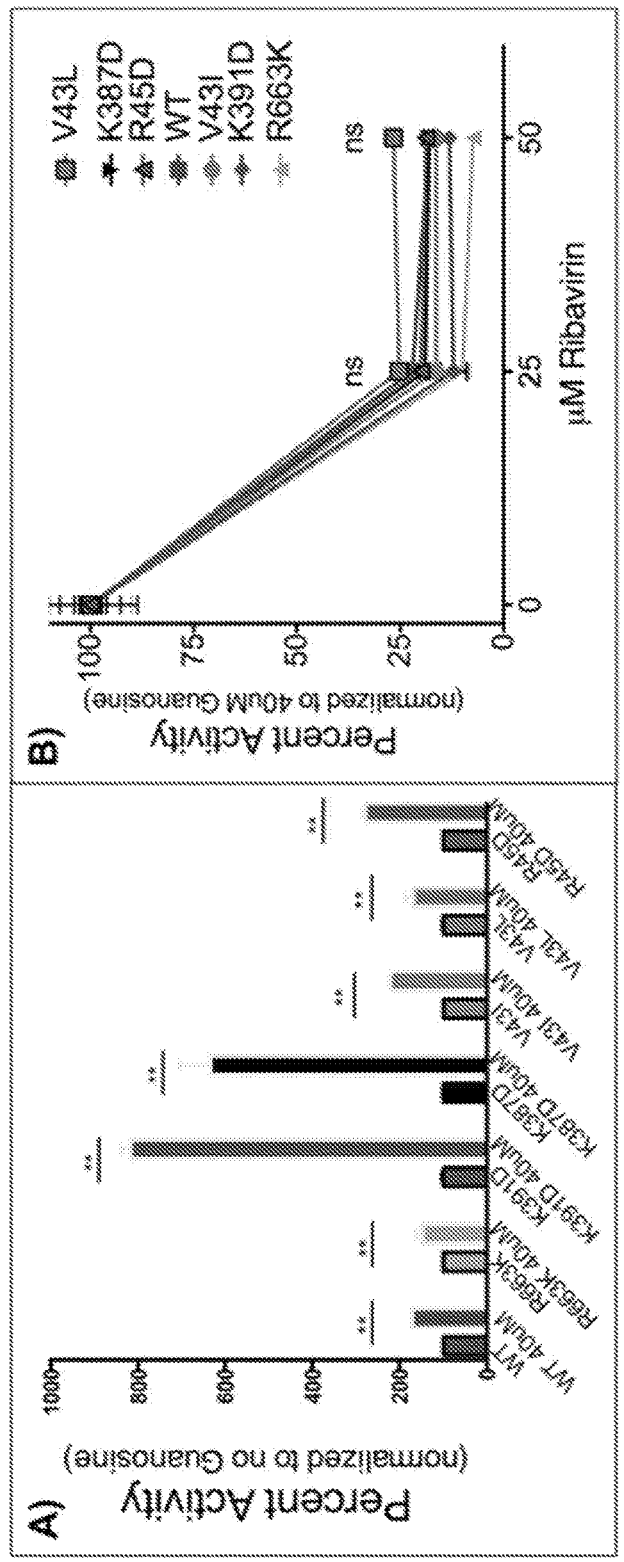

Finally, a determination was made of whether the inhibitory effects of ribavirin were due to nucleotide bias or direct incorporation into the growing mRNA. To do this, low dose guanosine (40 μM) was added to the cells and varied the concentration of ribavirin. PB1 mutations K387D, K391D had greatly increased activity in the presence of low dose guanosine (40 μM) (FIG. 5A). However, when the minigenome assays were performed in cells that were treated with 40 μM guanosine plus ribavirin (25 or 50 μM), all of the mutants showed the same response as the wild-type enzyme (FIG. 5B). This shows the mutations are not directly affecting nucleotide incorporation in the presence of guanosine, but rather that they are affecting the ability of the viral polymerase to utilize limited nucleotide pools.

2. Example 2: Identify the Highest Fidelity Variant of the 1$^{st}$ Generation Nucleotide Entry Channel Mutants An initial panel of polymerase mutants (FIG. 2) was created and analyzed with ribavirin and guanosine (FIG. 3). The analysis can be extended by treating cells with methotrexate, favipiravir, 5-fluorouracil and 5-azacytidine (all available from Sigma). These conditions examine both susceptibility to nucleotide bias (methotrexate) and direct competitive inhibition. Initially the effect of the mutagens on polymerase activity is examined as measured by minigenome assay (see FIG. 3 for methods). Briefly, cells are pre-treated with the various mutagens and measure the impact on reporter gene production as normalized to cell transfection and viability controls. Assays are conducted in which the base whose synthesis (or phosphorylation) is impaired by the nucleotide analog (FIG. 5) is added back. To test whether reduction in reporter gene activity is through lethal mutagenesis or reduced mRNA synthesis, RT-PCR is performed to determine the relative levels and lengths of reporter gene mRNA.

The impact of these nucleoside analogs on virus growth and viral mutation frequency was tested. Virus replication was analyzed in both Madin Darby Canine Kidney (MDCK) cells and human lung carcinoma (A549) cells. This allowed for the detection of differences at both elevated and reduced rates of replication, as altered by temperature. Briefly, cells were infected with virus at a multiplicity of infection (M.O.I.) of 0.05 and incubated with and without the indicated mutagens. Aliquots of culture supernatants were collected at 8, 16, 24, 48, and 72 h.p.i. and titrated on MDCK cells to determine viral titer by plaque assay (PFU/ml) or enumeration of NP-expressing cells by immunofluorescence (FFU/ml).

Figure 6:
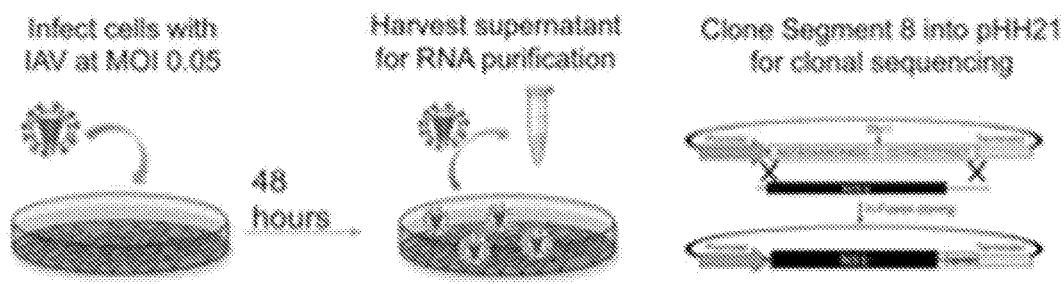

Also clonal sequencing was performed on viruses (wild-type and mutant) following two passages in MDCK cells in the absence of any mutagen, in order to calculate the relative mutational frequency of the wild-type and the high fidelity viruses (FIG. 6). Deep sequencing of virus stocks were completed by paired-end Illumina sequencing (2×125) to a ~100× coverage depth. Sequence reads were mapped to reference influenza A genomes using BWA and SNP/IN-DELs identified with Samtools+BCFtools.

Biochemical assays of the mutated viral polymerases are performed. Briefly, both wild type polymerase as well as polymerases containing the most promising fidelity mutants using baculovirus vectors are produced and purified. These purified heterotrimeric polymerases are used in primer extension assays. The rate of misincorporation with both biased (or omitted) nucleotide pools as well as in the presence of various mutagens (see above) is analyzed.

A second generation of single and combination mutants (Table 3) is designed based on the results of the first generation of mutants. Residues are mutated to both to alter the charge (K to E) at residues 235, 237, 239, 480, and 481 of PB1 as well as size (K to A and K to R). Additional residues are mutated at position 77, 78, 79, and 80 of PB1 and residues 661 and 691 of PA. The effects of these mutants is tested in minigenome and viral growth assays as described herein. Virus mutants exhibiting the greatest increase in fidelity are progressed to test the immunogenicity (and relative safety/attenuation) of these mutants by performing a lethal dose analysis in mice as well as determining serum antibody titers and susceptibility to heterologous challenge (see Table 4). Briefly, groups of 4 female 5-7-week old C57BL/6 mice are inoculated intranasally (i.n.) with the three most promising viruses. Weight loss is measured over the course of infection, through day 14 (see Vertebrate Animals section for details, including group size justification).

3. Example 3: Using High Fidelity Variants of IAV to Stabilize Attenuating and Genetically Unstable Mutations The ability of the high fidelity mutants to stabilize 6 previously identified, genetically unstable and attenuating mutations within PB2 (E65G, P112S, N265S, N556D, K627E, Y658H) is tested. All 6 of these mutations have been characterized in various temperature sensitive viruses that genotypically reverted. These mutations range in stability from K627E (lost in one passage in vivo) to N265S (stable in the current live attenuated vaccine upon dozens of passages). This panel of mutations therefore provides an ideal spectrum to characterize the high fidelity candidates. To assess viral fidelity viruses are created that contain this mutant PB2 segment in either conventional mouse adapted H1N1 (PR8), or in mutated derivatives of PR8 that contain the fidelity mutations of interest.

4. Example 4: Determination of the Ability of High Fidelity Viruses to Stabilize Otherwise Unstable Mutations Prior experiments identify novel fidelity variants of IAV, and test their ability to stabilize otherwise unfavorable mutations. To do this, advantage is taken of a cohort of mutations that were used for the rational design of influenza vaccine candidates—but which reverted upon passage in vitro and in vivo. These mutations (PB2-E65G, P112S, N265S, N556D, K627E, Y658H) (rev+) are introduced into the genetic background of A/PR/8/34 [H1N1] with and without the fidelity altering mutations; the corresponding viruses are produced using standard reverse genetics methods, as described.

Rev+ containing WT and fidelity modified viruses are serially passaged at low MOI (0.01) in both MDCK and A549 cells at the permissive temperature of 33° C. Later, the viruses are serially passaged in mice. The viruses are tittered before each passage to maintain a consistent MOI from passage to passage. Briefly, groups of 4 female 5-7-week old C57BL/6 mice are inoculated intranasally (i.n.) with rev+ WT and the 3 most promising high fidelity viruses at 0.1 $LD_{50}$. Weight loss is measured over the course of infection, and at 3 days post infection, lungs are surgically extracted and virus titers determined from homogenized lung tissue.

Virus titers for both experiments are determined by infecting triplicate wells of confluent MDCK cells with 10-fold serial dilutions of virus and NP-expressing cells are enumerated to determine virus titer in FFU/ml. Each virus passage is clarified by centrifugation, and aliquots of each passage stored at −80° C.

The test viruses are then passaged in vitro either until all PB2 mutations have been removed or for 15 passages (whichever comes first), and in vivo for 5 passages. Deep sequencing of the PB2 gene from the passaged virus stocks are performed at in vitro passages 1, 3, 5 and 15, as well as at in vivo passages 1, 3 and 5; results are compared to wild-type PR8 virus harboring the same rev+ mutations (see above). Sequencing methods are performed using any method known and accepted in the art.

Each passage is tested for phenotypic reversion through multicycle growth kinetics. The original, unpassaged virus stock is also passaged at elevated temperature (39° C.). Viruses that are able to grow at 39° C. are then plaque purified and sequenced in their entirety. Using this approach, both true reversion rate and the rate of emergence of second site suppressor mutations is monitored. Overall, fidelity mutants are identified which are capable of stabilizing unfavorable viral mutations.

E. References

Advisory Committee on Immunization Practices (ACIP) reaffirms recommendation for annual influenza vaccination 2015 [cited 2015 Jun. 11].

Aggarwal S, Bradel-Tretheway B, Takimoto T, Dewhurst S, Kim B. Biochemical characterization of enzyme fidelity of influenza A virus RNA polymerase complex. PLoS One. 2010; 5(4):e10372. Epub 2010 May 11. doi: 10.1371/journal.pone.0010372. PubMed PMID: 20454455; PMCID: PMC2861597.

Aggarwal S, Dewhurst S, Takimoto T, Kim B. Biochemical impact of the host adaptation-associated PB2 E627K mutation on the temperature-dependent RNA synthesis kinetics of influenza A virus polymerase complex. J Biol Chem. 2011; 286(40):34504-13. Epub 2011 Aug. 6. doi: 10.1074/jbc.M111.262048. PubMed PMID: 21816827; PMCID: PMC3186381.

Arezi B, Hogrefe H H. *Escherichia coli* DNA polymerase III epsilon subunit increases Moloney murine leukemia virus reverse transcriptase fidelity and accuracy of RT-PCR procedures. Anal Biochem. 2007; 360(1):84-91. Epub 2006 Nov. 17. doi: 10.1016/j.ab.2006.10.009. PubMed PMID: 17107651.

Batiuk T D, Schnizlein-Bick C, Plotkin Z, Dagher P C. Guanine nucleosides and Jurkat cell death: roles of ATP depletion and accumulation of deoxyribonucleotides. Am J Physiol Cell Physiol. 2001; 281(6):C1776-84. Epub 2001 Nov. 8. PubMed PMID: 11698235.

Belshe R B, Ambrose C S, Yi T. Safety and efficacy of live attenuated influenza vaccine in children 2-7 years of age. Vaccine. 2008; 26 Suppl 4:D10-6. Epub 2008 Jul. 10. doi: 10.1016/j.vaccine.2008.06.083. PubMed PMID: 18611422.

Bogs J, Kalthoff D, Veits J, Pavlova S, Schwemmle M, Manz B, Mettenleiter T C, Stech J. Reversion of PB2-627E to -627K during replication of an H5N1 Clade 2.2 virus in mammalian hosts depends on the origin of the nucleoprotein. J Virol. 2011; 85(20):10691-8. Epub 2011 Aug. 19. doi: 10.1128/jvi.00786-11. PubMed PMID: 21849466; PMCID: PMC3187502.

Boyer P L, Stenbak C R, Hoberman D, Linial M L, Hughes S H. In vitro fidelity of the prototype primate foamy virus (PFV) R T compared to HIV-1 R T. Virology. 2007; 367(2):253-64. Epub 2007 Jul. 17. doi: 10.1016/j.virol.2007.05.034. PubMed PMID: 17631930; PMCID: PMC2720797.

Bradel-Tretheway B G, Kelley Z, Chakraborty-Sett S, Takimoto T, Kim B, Dewhurst S. The human H5N1 influenza A virus polymerase complex is active in vitro over a broad range of temperatures, in contrast to the WSN complex, and this property can be attributed to the PB2 subunit. J Gen Virol. 2008; 89(Pt 12):2923-32. Epub 2008 Nov. 15. doi: 10.1099/vir.0.2008/006254-0. PubMed PMID: 19008377; PMCID: PMC3067610.

Burnet F M, Lind P E. Reversion to virulence in an influenza virus mutant. Aust J Exp Biol Med Sci. 1957; 35(3):225-39. Epub 1957 Jun. 1. PubMed PMID: 13471436.

Campagnola G, McDonald S, Beaucourt S, Vignuzzi M, Peersen O B. Structure-function relationships underlying the replication fidelity of viral RNA-dependent RNA polymerases. J Virol. 2015; 89(1):275-86. Epub 2014 Oct. 17. doi: 10.1128/jvi.01574-14. PubMed PMID: 25320316; PMCID: PMC4301111.

Cheung P P, Watson S J, Choy K T, Fun Sia S, Wong D D, Poon L L, Kellam P, Guan Y, Malik Peiris J S, Yen H L. Generation and characterization of influenza A viruses with altered polymerase fidelity. Nat Commun. 2014; 5:4794. Epub 2014 Sep. 4. doi: 10.1038/ncomms5794. PubMed PMID: 25183443; PMCID: PMC4155405.

Cox A, Baker S F, Nogales A, Martinez-Sobrido L, Dewhurst S. Development of a mouse-adapted live attenuated influenza virus that permits in vivo analysis of enhancements to the safety of live attenuated influenza virus vaccine. J Virol. 2015; 89(6):3421-6. Epub 2015 Jan. 2. doi: 10.1128/jvi.02636-14. PubMed PMID: 25552727; PMCID: PMC4337518.

Cox N J, Kendal A P. Genetic stability of A/Ann Arbor/6/60 cold-mutant (temperature-sensitive) live influenza virus genes: analysis by oligonucleotide mapping of recombinant vaccine strains before and after replication in volunteers. *J Infect Dis.* 1984; 149(2):194-200. Epub 1984 Feb. 1. PubMed PMID: 6699431.

Cox N J, Kitame F, Kendal A P, Maassab H F, Naeve C. Identification of sequence changes in the cold-adapted, live attenuated influenza vaccine strain, A/Ann Arbor/6/60 (H2N2). Virology. 1988; 167(2):554-67. Epub 1988 Dec. 1. PubMed PMID: 2974219.

Cramer J, Strerath M, Marx A, Restle T. Exploring the effects of active site constraints on HIV-1 reverse transcriptase DNA polymerase fidelity. J Biol Chem. 2002; 277(46):43593-8. Epub 2002 Aug. 30. doi: 10.1074/jbc.M207854200. PubMed PMID: 12200452.

Curti E, Jaeger J. Residues Arg283, Arg285, and Ile287 in the nucleotide binding pocket of bovine viral diarrhea virus NS5B RNA polymerase affect catalysis and fidelity. J Virol. 2013; 87(1):199-207. Epub 2012 Oct. 19. doi: 10.1128/jvi.06968-11. PubMed PMID: 23077294; PMCID: PMC3536392.

Donabedian A M, DeBorde D C, Cook S, Smitka C W, Maassab H F. A mutation in the P A protein gene of cold-adapted B/Ann Arbor/1/66 influenza virus associated with reversion of temperature sensitivity and attenuated virulence. Virology. 1988; 163(2):444-51. Epub 1988 Apr. 1. PubMed PMID: 3354203.

Eckert K A, Kunkel T A. Fidelity of DNA synthesis catalyzed by human DNA polymerase alpha and HIV-1 reverse transcriptase: effect of reaction pH. Nucleic Acids Res. 1993; 21(22):5212-20. Epub 1993 Nov. 11. PubMed PMID: 7504813; PMCID: PMC310639.

Fisher T S, Prasad V R. Substitutions of Phe61 located in the vicinity of template 5'-overhang influence polymerase fidelity and nucleoside analog sensitivity of HIV-1 reverse transcriptase. J Biol Chem. 2002; 277(25):22345-52. Epub 2002 Apr. 12. doi: 10.1074/jbc.M200282200. PubMed PMID: 11948182.

Garforth S J, Domaoal R A, Lwatula C, Landau M J, Meyer A J, Anderson K S, Prasad V R. K65R and K65A substitutions in HIV-1 reverse transcriptase enhance polymerase fidelity by decreasing both dNTP misinsertion and mispaired primer extension efficiencies. J Mol Biol. 2010; 401(1):33-44. Epub 2010 Jun. 12. doi: 10.1016/j.jmb.2010.06.001. PubMed PMID: 20538005; PMCID: PMC2925049.

Gnadig N F, Beaucourt S, Campagnola G, Borderia A V, Sanz-Ramos M, Gong P, Blanc H, Peersen O B, Vignuzzi M. Coxsackievirus B3 mutator strains are attenuated in vivo. Proc Natl Acad Sci USA. 2012; 109(34):E2294-303. Epub 2012 Aug. 3. doi: 10.1073/pnas.1204022109. PubMed PMID: 22853955; PMCID: PMC3427060.

Graham R L, Becker M M, Eckerle L D, Bolles M, Denison M R, Baric R S. A live, impaired-fidelity coronavirus vaccine protects in an aged, immunocompromised mouse model of lethal disease. *Nat Med.* 2012; 18(12):1820-6. Epub 2012 Nov. 13. doi: 10.1038/nm.2972. PubMed PMID: 23142821; PMCID: PMC3518599.

Grohskopf L A, Olsen S J, Sokolow L Z, Bresee J S, Cox N J, Broder K R, Karron R A, Walter E B. Prevention and control of seasonal influenza with vaccines: recommendations of the Advisory Committee on Immunization Practices (ACIP)—United States, 2014-15 influenza season. MMWR Morb Mortal Wkly Rep. 2014; 63(32):691-7. Epub 2014 Aug. 15. PubMed PMID: 25121712.

Hrabar A, Vodopij a I, Andre F E, Mitchell J R, Maassab H F, Hennessy A V, Davenport F M. A placebo-controlled dose-response study of the reactogenicity and immunogenicity of a cold-adapted recombinant A/Victoria/3/75 (H3N2) live influenza virus candidate vaccine in healthy volunteers. Dev Biol Stand. 1977; 39:53-60. Epub 1977 Jun. 1. PubMed PMID: 342317.

Hudjetz B, Gabriel G. Human-like PB2 627K influenza virus polymerase activity is regulated by importin-alpha1 and -alpha7. PLoS Pathog. 2012; 8(1):e1002488. Epub 2012 Jan. 26. doi: 10.1371/journal.ppat.1002488. PubMed PMID: 22275867; PMCID: PMC3262014.

Kaushik N, Singh K, Alluru I, Modak M J. Tyrosine 222, a member of the YXDD motif of MuLV R T, is catalytically essential and is a major component of the fidelity center. Biochemistry. 1999; 38(9):2617-27. Epub 1999 Mar. 3. doi: 10.1021/bi9824285. PubMed PMID: 10052931.

Keulen W, van Wijk A, Schuurman R, Berkhout B, Boucher C A. Increased polymerase fidelity of lamivudine-resistant HIV-1 variants does not limit their evolutionary potential. AIDS. 1999; 13(11):1343-9. Epub 1999 Aug. 17. PubMed PMID: 10449287.

Kim B, Ayran J C, Sagar S G, Adman E T, Fuller S M, Tran N H, Horrigan J. New human immunodeficiency virus, type 1 reverse transcriptase (HIV-1 R T) mutants with increased fidelity of DNA synthesis. Accuracy, template binding, and processivity. J Biol Chem. 1999; 274(39): 27666-73. Epub 1999 Sep. 17. PubMed PMID: 10488107.

Kim H W, Arrobio J O, Brandt C D, Parrott R H, Murphy B R, Richman D D, Chanock R M. Temperature-sensitive mutants of influenza A virus: response of children to the influenza A/Hong Kong/68-is-1(E) (H3N2) and influenza A/Udorn/72-is-1(E) (H3N2) candidate vaccine viruses and significance of immunity to neuraminidase antigen. Pediatr Res. 1976; 10(4):238-42. Epub 1976 Apr. 1. doi: 10.1203/00006450-197604000-00008. PubMed PMID: 1272630.

Lauring A S, Jones J O, Andino R. Rationalizing the development of live attenuated virus vaccines. *Nat Biotechnol.* 2010; 28(6):573-9. Epub 2010 Jun. 10. doi: 10.1038/nbt.1635. PubMed PMID: 20531338; PMCID: PMC2883798.

Li H, Durbin R. Fast and accurate short read alignment with Burrows-Wheeler transform. Bioinformatics. 2009; 25(14):1754-60. Epub 2009 May 20. doi: 10.1093/bioinformatics/btp324. PubMed PMID: 19451168; PMCID: PMC2705234.

Li H. A statistical framework for SNP calling, mutation discovery, association mapping and population genetical parameter estimation from sequencing data. Bioinformatics. 2011; 27(21):2987-93. Epub 2011 Sep. 10. doi: 10.1093/bioinformatics/btr509. PubMed PMID: 21903627; PMCID: PMC3198575.

Liu X, Yang X, Lee C A, Moustafa I M, Smidansky E D, Lum D, Arnold J J, Cameron C E, Boehr D D. Vaccine-derived mutation in motif D of poliovirus RNA-dependent RNA polymerase lowers nucleotide incorporation fidelity. *J Biol Chem.* 2013; 288(45):32753-65. Epub 2013 Oct. 3. doi: 10.1074/jbc.M113.484428. PubMed PMID: 24085299; PMCID: PMC3820909.

Long J S, Howard W A, Nunez A, Moncorge O, Lycett S, Banks J, Barclay W S. The effect of the PB2 mutation 627K on highly pathogenic H5N1 avian influenza virus is dependent on the virus lineage. J Virol. 2013; 87(18): 9983-96. Epub 2013 Jul. 12. doi: 10.1128/jvi.01399-13. PubMed PMID: 23843645; PMCID: PMC3753988.

Maassab H F. Adaptation and growth characteristics of influenza virus at 25 degrees c. Nature. 1967; 213(5076): 612-4. Epub 1967 Feb. 11. PubMed PMID: 6040602.

Maassab H F. Biologic and immunologic characteristics of cold-adapted influenza virus. J Immunol. 1969; 102(3): 728-32. Epub 1969 Mar. 1. PubMed PMID: 5773321.

Martinez-Sobrido L, Garcia-Sastre A. Generation of recombinant influenza virus from plasmid DNA. J Vis Exp. 2010(42). Epub 2010 Aug. 24. doi: 10.3791/2057. PubMed PMID: 20729804; PMCID: PMC3156010.

Medimmune. FluMist Quadrivalent Prescribing Information 2013-2014. 2013 [cited 2015 Jun. 10].

Meng T, Kwang J. Attenuation of human enterovirus 71 high-replication-fidelity variants in AG129 mice. J Virol. 2014; 88(10):5803-15. Epub 2014 Mar. 14. doi: 10.1128/jvi.00289-14. PubMed PMID: 24623423; PMCID: PMC4019108.

Murphy B R, Maassab H F, Wood F T, Jr., Chanock R M. Characterization of the temperature sensitive phenotype of the A/Ann Arbor/6/60 cold-adapted virus and its recombinants. Infect Immun. 1981; 32(2):960-3. Epub 1981 May 1. PubMed PMID: 7251154; PMCID: PMC351536.

Noble E, Cox A, Deval J, Kim B. Endonuclease substrate selectivity characterized with full-length P A of influenza A virus polymerase. Virology. 2012; 433(1):27-34. Epub 2012 Jul. 31. doi: 10.1016/j.virol.2012.07.008. PubMed PMID: 22841552; PMCID: PMC3647620.

Nogales A, Baker S F, Ortiz-Riano E, Dewhurst S, Topham D J, Martinez-Sobrido L. Influenza A virus attenuation by codon deoptimization of the N S gene for vaccine development. *J Virol.* 2014; 88(18):10525-40. Epub 2014 Jun. 27. doi: 10.1128/jvi.01565-14. PubMed PMID: 24965472; PMCID: PMC4178899.

Osterholm M T, Kelley N S, Sommer A, Belongia E A. Efficacy and effectiveness of influenza vaccines: a systematic review and meta-analysis. Lancet Infect Dis. 2012; 12(1):36-44. Epub 2011 Oct. 29. doi: 10.1016/s1473-3099(11)70295-x. PubMed PMID: 22032844.

Oude Essink B B, Back N K, Berkhout B. Increased polymerase fidelity of the 3T C-resistant variants of HIV-1 reverse transcriptase. Nucleic Acids Res. 1997; 25(16):3212-7. Epub 1997 Aug. 15. PubMed PMID: 9241223; PMCID: PMC146883.

Parkin N T, Chiu P, Coelingh K. Genetically engineered live attenuated influenza A virus vaccine candidates. J Virol. 1997; 71(4):2772-8. Epub 1997 Apr. 1. PubMed PMID: 9060631; PMCID: PMC191400.

Parkin N T, Chiu P, Coelingh K L. Temperature sensitive mutants of influenza A virus generated by reverse genetics and clustered charged to alanine mutagenesis. *Virus Res.* 1996; 46(1-2):31-44. Epub 1996 Dec. 1. PubMed PMID: 9029775.

Pflug A, Guilligay D, Reich S, Cusack S. Structure of influenza A polymerase bound to the viral RNA promoter. Nature. 2014; 516(7531):355-60. Epub 2014 Nov. 20. doi: 10.1038/nature14008. PubMed PMID: 25409142.

Poland G A, Fleming D M, Treanor J J, Maraskovsky E, Luke T C, Ball E M, Poland C M. New Wisdom to Defy an Old Enemy: Summary from a scientific symposium at the 4th Influenza Vaccines for the World (IVW) 2012 Congress, 11 October, Valencia, Spain. Vaccine. 2013; 31 Suppl 1:A1-20. Epub 2013 Apr. 23. doi: 10.1016/j.vaccine.2013.02.033. PubMed PMID: 23587330.

Prasad V R, Drosopoulos W C, Hamburgh M E. Perspective: research highlights at the Albert Einstein College of Medicine Center for AIDS research. Approaches to control drug resistance in HIV: the role of increased polymerase fidelity. AIDS Res Hum Retroviruses. 1996; 12(11):959-63. Epub 1996 Jul. 20. PubMed PMID: 8827210.

Prevention and control of influenza with vaccines: interim recommendations of the Advisory Committee on Immunization Practices (ACIP), 2013. MMWR Morb Mortal Wkly Rep. 2013; 62(18):356. Epub 2013 May 10. PubMed PMID: 23657110.

Recommendations for prevention and control of influenza in children, 2013-2014. Pediatrics. 2013; 132(4):e1089-104. Epub 2013 Sep. 4. doi: 10.1542/peds.2013-2377. PubMed PMID: 23999962.

Recommendations for prevention and control of influenza in children, 2014-2015. *Pediatrics*. 2014; 134(5):e1503-19. Epub 2014 Sep. 24. doi: 10.1542/peds.2014-2413. PubMed PMID: 25246619.

Rezende L F, Prasad V R. Nucleoside-analog resistance mutations in HIV-1 reverse transcriptase and their influence on polymerase fidelity and viral mutation rates. Int J Biochem Cell Biol. 2004; 36(9):1716-34. Epub 2004 Jun. 9. doi: 10.1016/j.biocel.2004.02.025. PubMed PMID: 15183340.

Schickli J H, Flandorfer A, Nakaya T, Martinez-Sobrido L, Garcia-Sastre A, Palese P. Plasmid-only rescue of influenza A virus vaccine candidates. Philos Trans R Soc Lond B Biol Sci. 2001; 356(1416):1965-73. Epub 2002 Jan. 10. doi: 10.1098/rstb.2001.0979. PubMed PMID: 11779399; PMCID: PMC1088576.

Singh K, Kaushik N, Jin J, Madhusudanan M, Modak M J. Role of Q190 of MuLV R T in ddNTP resistance and fidelity of DNA synthesis: a molecular model of interactions with substrates. Protein Eng. 2000; 13(9):635-43. Epub 2000 Oct. 31. PubMed PMID: 11054458.

Snyder M H, Betts R F, DeBorde D, Tierney E L, Clements M L, Herrington D, Sears S D, Dolin R, Maassab H F, Murphy B R. Four viral genes independently contribute to attenuation of live influenza A/Ann Arbor/6/60 (H2N2) cold-adapted reassortant virus vaccines. J Virol. 1988; 62(2):488-95. Epub 1988 Feb. 1. PubMed PMID: 3336068; PMCID: PMC250559.

Steel J, Lowen A C, Mubareka S, Palese P. Transmission of influenza virus in a mammalian host is increased by PB2 amino acids 627K or 627E/701N. PLoS Pathog. 2009; 5(1):e1000252. Epub 2009/01/03. doi: 10.1371/journal.ppat.1000252. PubMed PMID: 19119420; PMCID: PMC2603332.

Treanor J J, Kotloff K, Betts R F, Belshe R, Newman F, Iacuzio D, Wittes J, Bryant M. Evaluation of trivalent, live, cold-adapted (CAIV-T) and inactivated (TIV) influenza vaccines in prevention of virus infection and illness following challenge of adults with wild-type influenza A (H1N1), A (H3N2), and B viruses. Vaccine. 1999; 18(9-10):899-906. Epub 1999 Dec. 2. PubMed PMID: 10580204.

Tricco A C, Chit A, Soobiah C, Hallett D, Meier G, Chen M H, Tashkandi M, Bauch C T, Loeb M. Comparing influenza vaccine efficacy against mismatched and matched strains: a systematic review and meta-analysis. BMC Med. 2013; 11:153. Epub 2013 Jun. 27. doi: 10.1186/1741-7015-11-153. PubMed PMID: 23800265; PMCID: PMC3706345.

Tsfasman T M, Markushin S G, Akopova, I I, Ghendon Y Z. Molecular mechanisms of reversion to the ts+ (non-temperature-sensitive) phenotype of influenza A cold-adapted (ca) virus strains. J Gen Virol. 2007; 88(Pt 10):2724-9. Epub 2007 Sep. 18. doi: 10.1099/vir.0.83014-0. PubMed PMID: 17872525.

Vesikari T. Emerging data on the safety and efficacy of influenza vaccines in children. Pediatr Infect Dis J. 2008; 27(11 Suppl):S159-61. Epub 2008 Nov. 26. doi: 10.1097/INF.0b013e31818a545d. PubMed PMID: 18955892.

Vignuzzi M, Wendt E, Andino R. Engineering attenuated virus vaccines by controlling replication fidelity. Nat Med. 2008; 14(2):154-61. Epub 2008 Feb. 5. doi: 10.1038/nm1726. PubMed PMID: 18246077.

Weber M, Sediri H, Felgenhauer U, Binzen I, Banfer S, Jacob R, Brunotte L, Garcia-Sastre A, Schmid-Burgk J L, Schmidt T, Hornung V, Kochs G, Schwemmle M, Klenk H D, Weber F. Influenza virus adaptation PB2-627K modulates nucleocapsid inhibition by the pathogen sensor RIG-I. Cell Host Microbe. 2015; 17(3):309-19. Epub 2015 Feb. 24. doi: 10.1016/j.chom.2015.01.005. PubMed PMID: 25704008; PMCID: PMC4359673.

Weeks S A, Lee C A, Zhao Y, Smidansky E D, August A, Arnold J J, Cameron C E. A Polymerase mechanism-based strategy for viral attenuation and vaccine development. J Biol Chem. 2012; 287(38):31618-22. Epub 2012 Aug. 3. doi: 10.1074/jbc.C112.401471. PubMed PMID: 22854962; PMCID: PMC3442494.

Weiss K K, Bambara R A, Kim B. Mechanistic role of residue Gln151 in error prone DNA synthesis by human immunodeficiency virus type 1 (HIV-1) reverse transcriptase (RT). Pre-steady state kinetic study of the Q151N HIV-1 RT mutant with increased fidelity. J Biol Chem. 2002; 277(25):22662-9. Epub 2002 Apr. 3. doi: 10.1074/jbc.M200202200. PubMed PMID: 11927582.

Yang X, Smidansky E D, Maksimchuk K R, Lum D, Welch J L, Arnold J J, Cameron C E, Boehr D D. Motif D of viral RNA-dependent RNA polymerases determines efficiency and fidelity of nucleotide addition. Structure. 2012; 20(9):1519-27. Epub 2012 Jul. 24. doi: 10.1016/j.str.2012.06.012. PubMed PMID: 22819218; PMCID: PMC3438331.

F. Sequences

SEQ ID NO: 1 Amino Acid Sequence of PA from Influenza A virus strain A/little yellow-shouldered bat/Guatemala/060/2010(H17N10)(GenBank Accession NO. CY103891.1)

```
MENFVRTNFNPMILERAEKTMKEYGENPQNEGNKFAAISTHMEVCFMYSDFHFIDLEGNTIVKE
NDDDNAMLKHRFEIIEGQERNIAWTIVNSICNMTENSKPRFLPDLYDYKINKFIEIGVIRRKVE
DYYYEKASKLKGENVYIHIFSFDGEEMATDDEYILDEESRARIKTRLFVLRQELATAGLWDSFR
QSEKGEETLEEEFSYPPTFQRLANQSLPPSFKDYHQFKAYVSSFKANGNIEAKLGAMSEKVNAQ
IESFDPRTIRELELPEGKFCTQRSKFLLMDAMKLSVLNPAHEGEGIPMKDAKACLDTFWGWKKA
TIIKKHEKGVNTNYLMIWEQLLESIKEMEGKFLNLKKTNHLKWGLGEGQAPEKMDFEDCKEVPD
LFQYKSEPPEKRKLASWIQSEFNKASELTNSNWIEFDELGNDVAPIEHIASRRRNFFTAEVSQC
RASEYIMKAVYINTALLNSSCTAMEEYQVIPIITKCRDTSGQRRTNLYGFIIKGRSHLRNDTDV
VNFISLEFSLTDPRNEIHKWEKYCVLEIGDMEIRTSISTIMKPVYLYVRTNGTSKIKMKWGMEM
RRCLLQSLQQVESMIEAESAVKEKDMTEPFFRNRENDWPIGESPQGIEKGTIGKVCRVLLAKSV
```

| F. Sequences |
|---|

FNSIYASAQLEGFSAESRKLLLLIQAFRDNLDPGTFDLKGLYEAIEECIINDPWVLLNASWFNS
FLKAVQLSM

SEQ ID NO: 2 Amino Acid Sequence of PB1 from Influenza A virus strain
bat/Guatemala/060/2010(H17N10)(GenBank Accession NO. CY103890.1)
MDVNPMLIFLKVPVQNAISTTFPYTGDPPYSHGTGTGYTMDTVIRTHDYSSRGIWKTNSETGAQ
QLNPIDGPLPEDNEPSGYAQTDCVLELIEGLDRSHPGLFETACQETIDAIQQTRVDKLTQGRQT
YDWTLNRNQPAATALANTIEVFRKNGYKLNESGRLIDFLKDVLLSFENDSMEVTTHFQKKKRIR
DNHSKKMITQRTIGKKRVKLTKKNYLIRALTLNTMTKDAERGKLKRRAIATPGMQIRGFVYFVE
LLARNICERLEQSGLPVGGNEKKAKLANVIKKMMAKSTDEELSYTITGDNTKWNENQNPRIFLA
MVLRITAGQPEWFRDLLAVAPIMFSNKVARLGRGYMFESKSMHLRTQISAENLSDINLRYFNED
TKKKIEKIRHLMVEGTASLSPGMMMGMFNMLSTVLGVSVLNLGQREILKRTYWWDGLQSSDDFA
LIINGHFKEDIQQGVNHFYRTCKLVGINMSQKKSYINKTGTFEFTSFFYRYGFVANFSMELPSF
GVAGNNESADMSIGTTVIKTNMINNDLGPATAQMAIQLFIKDYRYTYRCHRGDINLETRRIKSI
KRLWTETISKAGLLVADGGPNPYNLRNLHIPEVCLKWSLMDPDYRGRLCNPNNPFVHHMEVEST
NLAVVMPAHGPAKSLEYDAVATTHSWTPKRNRSILNTNQRGILEDERIYQKCCQVFEKFFPSST
YRRPIGMASMLDAMLSRARIDARIDLESGRISSQDFSEITNTCKAIEALKRQ SEQ ID NO: 3 Amino Acid Sequence of PA from Influenza A virus strain A/
Puerto Rico/9/1934(H1N1))(GenBank Accession No. EF190981.1)
MEDFVRQCFNPMIVELAEKTMKEYGEDLKIETNKFAAICTHLEVCFMYSDFHFINEQGESIIVE
LGDPNALLKHRFEIIEGRDRTMAWTVVNSICNTTGAEKPKFLPDLYDYKENRFIEIGVTRREVH
IYYLEKANKIKSEKTHIHIFSFTGEEMATKADYTLDEESRARIKTRLFTIRQEMASRGLWDSFR
QSERGEETIEERFEITGTMRKLADQSLPPNFSSLENFRAYVDGFEPNGYIEGKLSQMSKEVNAR
IEPFLKTTPRPLRLPNGPPCSQRSKFLLMDALKLSIEDPSHEGEGIPLYDAIKCMRTFFGWKEP
NVVKPHEKGINPNYLLSWKQVLAELQDIENEEKIPKTKNMKKTSQLKWALGENMAPEKVDFDDC
KDVGDLKQYDSDEPELRSLASWIQNEFNKACELTDSSWIELDEIGEDVAPIEHIASMRRNYFTS
EVSHCRATEYIMKGVYINTALLNASCAAMDDFQLIPMISKCRTKEGRRKTNLYGFIIKGRSHLR
NDTDVVNFVSMEFSLTDPRLEPHKWEKYCVLEIGDMLIRSAIGQVSRPMFLYVRTNGTSKIKMK
WGMEMRRCLLQSLQQIESMIEAESSVKEKDMTKEFFENKSETWPIGESPKGVEESSIGKVCRTL
LAKSVFNSLYASPQLEGFSAESRKLLLIVQALRDNLEPGTFDLGGLYEAIEECLINDPWVLLNA
SWFNSFLTHALS SEQ ID NO: 4 Amino Acid Sequence of PB1 from Influenza A virus strain A/
Puerto Rico/9/1934(H1N1)(GenBank Accession No. EF190980.1)
MDVNPTLLFLKVPAQNAISTTFPYTGDPPYSHGTGTGYTMDTVNRTHQYSEKGRWTTNTETGAP
QLNPIDGPLPEDNEPSGYAQTDCVLEAMAFLEESHPGIFENSCIETMEVVQQTRVDKLTQGRQT
YDWTLNRNQPAATALANTIEVFRSNGLTANESGRLIDFLKDVMESMNKEEMGITTHFQRKRRVR
DNMTKKMITQRTMGKKKQRLNKRSYLIRALTLNTMTKDAERGKLKRRAIATPGMQIRGFVYFVE
TLARSICEKLEQSGLPVGGNEKKAKLANVVRKMMTNSQDTELSFTITGDNTKWNENQNPRMFLA
MITYMTRNQPEWFRNVLSIAPIMFSNKMARLGKGYMFESKSMKLRTQIPAEMLASIDLKYFNDS
TRKKIEKIRPLLIEGTASLSPGMMMGMFNMLSTVLGVSILNLGQKRYTKTTYWWDGLQSSDDFA
LIVNAPNHEGIQAGVDRFYRTCKLLGINMSKKKSYINRTGTFEFTSFFYRYGFVANFSMELPSF
GVSGINESADMSIGVTVIKNNMINNDLGPATAQMALQLFIKDYRYTYRCHRGDTIQTRRSFEI
KKLWEQTRSKVGLLVSDGGPNLYNIRNLHIPEVCLKWELMDDEYRGRLCNPLNPFVSHKEIESM
NNAVMMPAHGPAKNMEYDAVATTHSWIPKRNRSILNTSQRGVLEDEQMYQRCCNLFEKFFPSSS
YRRPVGISSMVEAMVSRARIDARIDFESGRIKKEEFTEIMKICSTIEELRRQK SEQ ID NO: 5 Nucleic Acid Sequence of PBA from Influenza A virus strain A/
Puerto Rico/9/1934(H1N1))(GenBank Accession No. EF190981.1)
      1    agcgaaagca ggtactgatc caaaatggaa gattttgtgc gacaatgctt caatccgatg
     61    attgtcgagc ttgcggaaaa aacaatgaaa gagtatgggg aggacctgaa aatcgaaaca
    121    aacaaatttg cagcaatatg cactcacttg gaagtatgct tcatgtattc agattttcac
    181    ttcatcaatg agcaaggcga gtcaataatc gtagaacttg gtgatccaaa tgcactttg
    241    aagcacagat tgaaataat cgagggaaga gatcgcacaa tggcctggac agtagtaaac
    301    agtatttgca cactacagg ggctgagaaa ccaaagtttc taccagattt gtatgattac
    361    aaggagaata gattcatcga aattggagta acaaggagag aagttcacat atactatctg
    421    gaaaaggcca ataaaattaa atctgagaaa acacacatcc acattttctc gttcactggg
    481    gaagaaatgg ccacaaaggc agactacact ctcgatgaag aaagcagggc taggatcaaa
    541    accagactat tcaccataag acaagaaatg gccagcagag gcctctggga ttcctttcgt
    601    cagtccgaga gaggagaaga gacaattgaa gaaggtttg aaatcacagg aacaatgcgc
    661    aagcttgccg accaaagtct cccgccgaac ttctccagcc ttgaaaattt tagagcctat
    721    gtggatggat tcgaaccgaa cggctacatt gagggcaagc tgtctcaaat gtccaaagaa
    781    gtaaatgcta gaattgaacc ttttttgaaa acaacaccac gaccacttag acttccgaat -continued F. Sequences

| | |
|---|---|
| 841 | gggcctccct gttctcagcg gtccaaattc ctgctgatgg atgccttaaa attaagcatt |
| 901 | gaggacccaa gtcatgaagg agagggaata ccgctatatg atgcaatcaa atgcatgaga |
| 961 | acattctttg gatggaagga acccaatgtt gttaaaccac acgaaaaggg aataaatcca |
| 1021 | aattatcttc tgtcatggaa gcaagtactg gcagaactgc aggacattga gaatgaggag |
| 1081 | aaaattccaa agactaaaaa tatgaagaaa acaagtcagc taaagtggga acttggtgag |
| 1141 | aacatggcac cagaaaaggt agactttgac gactgtaaag atgtaggtga tttgaagcaa |
| 1201 | tatgatagtg atgaaccaga attgaggtcg cttgcaagtt ggattcagaa tgagtttaac |
| 1261 | aaggcatgcg aactgacaga ttcaagctgg atagagctcg atgagattgg agaagatgtg |
| 1321 | gctccaattg aacacattgc aagcatgaga aggaattatt tcacatcaga ggtgtctcac |
| 1381 | tgcagagcca cagaatacat aatgaagggg gtgtacatca atactgcctt gcttaatgca |
| 1441 | tcttgtgcag caatggatga tttccaatta attccaatga taagcaagtg tagaactaag |
| 1501 | gagggaaggc gaaagaccaa cttgtatggt ttcatcataa aggaagatc ccacttaagg |
| 1561 | aatgacaccg acgtggtaaa ctttgtgagc atggagtttt ctctcactga cccaagactt |
| 1621 | gaaccacata atgggagaa gtactgtgtt cttgagatag agatatgct tataagaagt |
| 1681 | gccataggcc aggtttcaag gcccatgttc ttgtatgtga aacaaatgg aacctcaaaa |
| 1741 | attaaaatga atggggaat ggagatgagg cgttgcctcc tccagtcact tcaacaaatt |
| 1801 | gagagtatga ttgaagctga gtcctctgtc aaagagaaag acatgaccaa agagttcttt |
| 1861 | gagaacaaat cagaaacatg gcccattgga gagtccccca aggagtgga ggaaagttcc |
| 1921 | attgggaagg tctgcaggac tttattagca aagtcggtat tcaacagctt gtatgcatct |
| 1981 | ccacaactag aaggatttc agctgaatca agaaaactgc ttcttatcgt tcaggctctt |
| 2041 | agggacaacc ttgaacctgg gacctttgat cttgggggc tatatgaagc aattgaggag |
| 2101 | tgcctgatta atgatccctg ggttttgctt aatgcttctt ggttcaactc cttccttaca |
| 2161 | catgcattga gttagttgtg gcagtgctac tatttgctat ccatactgtc caaaaagta |
| 2221 | ccttgtttct act |

SEQ ID NO: 6 Nucleic Acid Sequence of PB1 from Influenza A virus strain A/
Puerto Rico/9/1934(H1N1)(GenBank Accession No. EF190980.1)

| | |
|---|---|
| 1 | agcgaaagca ggcaaaccat ttgaatggat gtcaatccga ccttactttt cttaaaagtg |
| 61 | ccagcacaaa atgctataag cacaactttc ccttatactg gagaccctcc ttacagccat |
| 121 | gggacaggaa caggatacac catggatact gtcaacagga cacatcagta ctcagaaaag |
| 181 | ggaagatgga caacaaacac cgaaactgga gcaccgcaac tcaacccgat tgatgggcca |
| 241 | ctgccagaag acaatgaacc aagtggttat gcccaaacag attgtgtatt ggaggcgatg |
| 301 | gctttccttg aggaatccca tcctggtatt tttgaaaact cgtgtattga acgatggag |
| 361 | gttgttcagc aaacacgagt agacaagctg acacaaggcc gacagaccta tgactggact |
| 421 | ctaaatagaa accaacctgc tgcaacagca ttggccaaca atagaagt gttcagatca |
| 481 | aatggcctca cggccaatga gtctggaagg ctcatagact tccttaagga tgtaatggag |
| 541 | tcaatgaaca agaagaaat ggggatcaca actcattttc agagaaagag acgggtgaga |
| 601 | gacaatatga ctaagaaaat gataacacag agaacaatgg taaaaagaa gcagagattg |
| 661 | aacaaaagga gttatctaat tagagcattg accctgaaca catgaccaa agatgctgag |
| 721 | agagggaagc taaaacggag agcaattgca ccccaggga tgcaaataag ggggtttgta |

| F. Sequences | |
|---|---|
| 781 | tactttgttg agacactggc aaggagtata tgtgagaaac ttgaacaatc agggttgcca |
| 841 | gttggaggca atgagaagaa agcaaagttg gcaaatgttg taaggaagat gatgaccaat |
| 901 | tctcaggaca ccgaactttc tttcaccatc actggagata acaccaaatg aacgaaaat |
| 961 | cagaatcctc ggatgttttt ggccatgatc acatatatga ccagaaatca gcccgaatgg |
| 1021 | ttcagaaatg ttctaagtat tgctccaata atgttctcaa acaaaatggc gagactggga |
| 1081 | aaagggtata tgtttgagag caagagtatg aaacttagaa ctcaaatacc tgcagaaatg |
| 1141 | ctagcaagca tcgatttgaa atatttcaat gattcaacaa gaagaagat tgaaaaaatc |
| 1201 | cgaccgctct aatagaggg gactgcatca ttgagccctg aatgatgat gggcatgttc |
| 1261 | aatatgttaa gcactgtatt aggcgtctcc atcctgaatc ttggacaaaa gagatacacc |
| 1321 | aagactactt actggtggga tggtcttcaa tcctctgacg attttgctct gattgtgaat |
| 1381 | gcacccaatc atgaagggat tcaagccgga gtcgacaggt tttatcgaac ctgtaagcta |
| 1441 | cttggaatca atatgagcaa gaaaaagtct tacataaaca gaacaggtac atttgaattc |
| 1501 | acaagttttt tctatcgtta tgggtttgtt gccaatttca gcatggagct tcccagtttt |
| 1561 | ggggtgtctg gatcaacga gtcagcggac atgagtattg gagttactgt catcaaaaac |
| 1621 | aatatgataa acaatgatct tggtccagca acagctcaaa tggcccttca gttgttcatc |
| 1681 | aaagattaca ggtacacgta ccgatgccat agaggtgaca cacaaataca accccgaaga |
| 1741 | tcatttgaaa taaagaaact gtgggagcaa acccgttcca agttggact gctggtctcc |
| 1801 | gacggaggcc caatttata caacattaga aatctccaca ttcctgaagt ctgcctaaaa |
| 1861 | tgggaattga tggatgagga ttaccagggg cgtttatgca acccactgaa cccatttgtc |
| 1921 | agccataaag aaattgaatc aatgaacaat gcagtgatga tgccagcaca tggtccagct |
| 1981 | aaaaacatgg agtatgatgc tgttgcaaca acacactcct ggatccccaa aagaaatcga |
| 2041 | tccatcttga atacaagtca agaggagta cttgaggatg aacaaatgta ccaaggtgc |
| 2101 | tgcaatttat ttgaaaaatt cttccccagc agttcataca gaagaccagt cgggatatcc |
| 2161 | agtatggtgg aggctatggt ttccagagcc cgaattgatg cacggattga tttcgaatct |
| 2221 | ggaaggataa agaaagaaga gttcactgag atcatgaaga tctgttccac cattgaagag |
| 2281 | ctcagacggc aaaaatagtg aatttagctt gtccttcatg aaaaaatgcc ttgtttctac |
| 2341 | t | |

SEQ ID NO: 7 Amino Acid sequence of alpha helix at residues 36-50 of PB1.
TGYTMDTVNRTHQYSE SEQ ID NO: 8 Amino Acid sequence of alpha helix at residues 383-395 of PB1.
DSTRKKIEKIRPL SEQ ID NO: 9 Amino Acid sequence of loop at residues 77-80 of PB1.
NEPS SEQ ID NO: 10 Amino Acid sequence of loop at residues 228-240 of PB1.
TKDAERGKLKRRA SEQ ID NO: 11 Amino Acid sequence of loop at residues 306-311 of PB1.
NTKWNE SEQ ID NO: 12 Amino Acid sequence of alpha helix at residues 654-674 of PA.
QLEGFSAESRKLLLIVQALRD SEQ ID NO: 13 Amino Acid sequence of alpha helix at residues 682-693 of PA.
DLGGLYEAIEEC

What is claimed is:

1. A modified influenza A virus comprising one or more mutations in the influenza RNA polymerase, wherein the one or more mutations causes an increased fidelity of the polymerase, wherein the mutation comprises a Lysine to Aspartic acid substitution at a residue corresponding to residue 387 or 391 of the PB1 subunit of the influenza RNA polymerase as set forth in SEQ ID NO: 4.

2. The modified influenza A virus of claim 1, wherein the influenza RNA polymerase further comprises a mutation at one or more residues of an alpha helix of the PA subunit of the influenza RNA polymerase.

3. The modified influenza A virus of claim 2, wherein the influenza RNA polymerase comprises a mutation at one or more residues of the alpha helix corresponding to residues 661 or 663 of the PA subunit of the influenza RNA polymerase as set forth in SEQ ID NO: 3; wherein the mutation at residue 661 does not comprise Arginine to Glutamic acid substitution.

4. The modified influenza A virus of claim 3, wherein the mutation comprises an Arginine to Lysine substitution at a residue corresponding to residue 663 of the PA subunit of the influenza RNA polymerase as set forth in SEQ ID NO: 3.

5. A method of immunizing a subject against influenza virus, inducing an immune response against influenza virus in a subject, or inhibiting an influenza virus infection in a subject comprising administering to the subject the modified influenza virus of claim 1.

6. A recombinant nucleic acid encoding an influenza RNA polymerase with increased transcriptional fidelity wherein the RNA polymerase comprises at least one mutation in the PB1 subunit of the RNA polymerase, wherein the at least one mutation comprises a lysine to aspartic acid substitution at a residue corresponding to residue 387 or 391 of the PB1 subunit of the influenza RNA polymerase as set forth in SEQ ID NO: 4.

7. A method of increasing the immunogenicity of an attenuated influenza vaccine comprising obtaining an attenuated influenza vaccine viral strain and generating a mutation in the PB1 subunit of the RNA polymerase of the influenza virus; wherein the mutation comprises a lysine to aspartic acid substitution at a residue corresponding to residue 387 or 391 of the PB1 subunit of the influenza RNA polymerase as set forth in SEQ ID NO: 4; and wherein the mutation increases the fidelity of the RNA polymerase; and wherein an increase in fidelity of the polymerase increases the stability of the virus strain in a subject and reduces the amount mutant viruses formed during transcription of the virus thereby increasing the abundance of a single strain and as a result increases the immune response to the immunizing strain.

* * * * *